US006420524B1

(12) United States Patent
Craig

(10) Patent No.: US 6,420,524 B1
(45) Date of Patent: Jul. 16, 2002

(54) GAIN OF FUNCTION MUTATIONS IN ATP-DEPENDENT TRANSPOSITION PROTEINS

(75) Inventor: Nancy L. Craig, Baltimore, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/027,169

(22) Filed: Feb. 20, 1998

Related U.S. Application Data

(60) Provisional application No. 60/037,955, filed on Feb. 20, 1997.

(51) Int. Cl.$^7$ .................................................. C07K 1/00
(52) U.S. Cl. ...................................... 530/350; 536/23.2
(58) Field of Search .......................... 530/350; 536/23.1, 536/23.2; 435/91.1, 6, 320.1, 440, 471, 473

(56) References Cited

U.S. PATENT DOCUMENTS

| 5,677,170 A | 10/1997 | Devine et al. ............ 435/320.1 |
| 5,728,551 A | 3/1998 | Devine et al. ................. 435/6 |

OTHER PUBLICATIONS

Craig (Jul. 1997) "Target Site Selection In Transposition", *Annu. Rev. Biochem.* 66:437–474.

Craig (Nov. 1995) "Transposon Tn7", *Curr. Top. Microbiol. Immunol.* 204:27–48.

Davies, et al. (1995) "Insertion Site Specificity Of The Transposon Tn3", *Nucleic Acids Research* 23 (3):507–514.

Devine, et al. (1994) "Efficient Integration Of Artificial Transposons Into Plasmid Targets In Vitro: A Useful Tool for DNA Mapping, Sequencing And Genetic Analysis", *Nucleic Acids Research* 22 (18):3765–3772.

Pryciak, et al. (1992) "Nucleosomes, DNA–Binding Proteins, And DNA Sequence Modulate Retroviral Integration Target Site Selection", *Cell* 69 (5):769–780.

Pryciak, et al. (1992) "Retroviral Integration Into Minichromosomes In Vitro", *The EMBO Journal* 11 (1):291–303.

Pryciak, et al. (1992) "Simian Virus 40 Minichromosomes As Targets For Retroviral Integration In Vito", *Proc. Nat'l. Acad. Sci. USA* 89 (19):9237–9241.

Singh, et al. (Feb. 18, 1997) "High–Resolution Functional Mapping Of A Cloned Gene By Genetic Footprinting", *Proc. Nat'l. Acad. Sci. USA.* 94 (4):1304–1309.

Stellwagen, et al. (Aug. 1997) "Avoiding Self: Two Tn7–Encoded Proteins Mediate Target Immunity In Tn7 Transposition", *The EMBO Journal* 16 (22):6823–6834.

Surette et al. (1991) "Stimulation Of The Mu DNA Strand Cleavage And Intramolecular Strand Transfer Reactions By The Mu B Potein Is Independent Of Stable Binding Of The Mu B Protein To DNA", *The Journal of Biological Chemistry* 266 (26):17306–17313.

Stellwagen et al. (Mar. 1997) "Gain Of Function Mutations In TnsC, An ATP–Dependent Transposition Protein That Activates The Bacterial Transposon Tn7", *Genetics* 145 (3):573–585.

Bender et al. (1992) "IS10 Transposase Mutations That Specifically Alter Target Site Recognition", *The EMBO Journal* 11 (2):741–750.

*Primary Examiner*—Remy Yucel
(74) *Attorney, Agent, or Firm*—Alston & Bird LLP

(57) ABSTRACT

The invention is specifically directed to efficient, random, simple insertion of a transposon or derivative transposable element into DNA in vivo or in vitro. The invention is particularly directed to mutations in ATP-utilizing regulatory transposition proteins that permit insertion with less target-site specificity than wild-type. The invention encompasses gain-of-function mutations in TnsC, an ATP-utilizing regulatory transposition protein that activates the bacterial transposon Tn7. Such mutations enable the insertion of a Tn7 transposon or derivative transposable element in a non-specific manner into a given DNA segment. Insertion can be effected in plasmid and cosmid libraries, cDNA libraries, PCR products, bacterial artificial chromosomes, yeast artificial chromosomes, mammalian artificial chromosomes, genomic DNAs, and the like. Such insertion is useful in DNA sequencing methods, for genetic analysis by insertional mutagenesis, and alteration of gene expression by insertion of a given genetic sequence.

14 Claims, 27 Drawing Sheets

Class I TnsC mutants

Class II TnsC mutants

Positions of TnsC$^{A225V}$ Insertions

FIG. 9B

```
TTTAGAGCAATTCGGTGTTAGTTTCAGCAAGCAAACATTAACCATAGCTA
ATGATTTATAGCCATATTAACCATTGGGGTACCGAGCTCGAATTCCATGG
TCTGTTTCCTGTGTGAAATTGTTATCCGCTCACAATTCCACACATTATAC
GAGCCGGATGATTAATTGTCAACAGCTCATTTCAGAATATTTGCCAGAAC
CGTTATGATGTCGGCGCAAAAAACATTATCCAGAACGGGAGTGCGCCTTG
AGCGACACGAATTATGCAGTGATTTACGACCTGCACAGCCATACCACAGC
TTCCGATGGCTGCCTGACGCCAGAAGCATTGGTGCACCGTGCAGTCGATG
ATAAGCTGTCAAACCAGATCAATTCGCGCTAACTCACATTAATTGCGTTG
CGCTCACTGCCCGCTTTCCAGTCGGGAAACCTGTCGTGCCAGCTGCATTA
ATGAATCGGCCAACGCGCGGGGAGAGGCGGTTTGCGTATTGGGCGCCAGG
GTGGTTTTTCTTTTCACCAGTGAGACGGGCAACAGCTGATTGCCCTTCAC
CGCCTGGCCCTGAGAGAGTTGCAGCAAGCGGTCCACGCTGGTTTGCCCCA
GCAGGCGAAAATCCTGTTTGATGGTGGTTGACGGCGGGATATAACATGAG
CTGTCTTCGGTATCGTCGTATCCCACTACCGAGATATCCGCACCAACGCG
CAGCCCGGACTCGGTAATGGCGCGCATTGCGCCCAGCGCCATCTGATCGT
TGGCAACCAGCATCGCAGTGGGAACGATGCCCTCATTCAGCATTTGCATG
GTTTGTTGAAAACCGGACATGGCACTCCAGTCGCCTTCCCGTTCCGCTAT
CGGCTGAATTTGATTGCGAGTGAGATATTTATGCCAGCCAGCCAGACGCA
GACGCGCCGAGACAGAACTTAATGGGCCCGCTAACAGCGCGATTTGCTGG
TGACCCAATGCGACCAGATGCTCCACGCCCAGTCGCGTACCGTCTTCATG
GGAGAAAATAATACTGTTGATGGGTGTCTGGTCAGAGACATCAAGAAATA
ACGCCGGAACATTAGTGCAGGCAGCTTCCACAGCAATGGCATCCTGGTCA
TCCAGCGGATAGTTAATGATCAGCCCACTGACGCGTTGCGCGAGAAGATT
GTGCACCGCCGCTTTACAGGCTTCGACGCCGCTTCGTTCTACCATCGACA
CCACCACGCTGGCACCCAGTTGATCGGCGCGAGATTTAATCGCCGCGACA
ATTTGCGACGGCGCGTGCAGGGCCAGACTGGAGGTGGCAACGCCAATCAG
CAACGACTGTTTGCCCGCCAGTTGTTGTGCCACGCGGTTGGGAATGTAAT
TCAGCTCCGCCATCGCCGCTTCCACTTTTTCCCGCGTTTTCGCAGAAACG
TGGCTGGCCTGGTTCACCACGCGGGAAACGGTCTGATAAGAGACACCGGC
ATACTCTGCGACATCGTATAACGTTACTGGTTTCACATTCACCACCCTGA
ATTGACTCTCTTCCGGGCGCTATCATGCCATACCGCGAAAGGTTTTGCAC
CATTCGATGGTGTCAACGTAAATGCATGCCGCTTCGCCTTCGCGCGCGAA
TTGATCTGCTGCCTCGCGCGTTTCGGTGATGACGGTGAAAACCTCTGACA
CATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGC
GCAGCCATGACCCAGTCACGTAGCGATAGCGGAGTGTATACTGGCTTAAC
TATGCGGCATCAGAGCAGATTGTACTGAGAGTGCACCATATGCGGTGTGA
AATACCGCACAGATGCGTAAGGAGAAAATACCGCATCAGGCGCTCTTCCG
CTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGA
TAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTA
```

FIG. 9B CONT-1

```
AGACACGACTTATCGCCACTGGCAGCAGCCACTGGTAACAGGATTAGCAG
AGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCA
GTTACCTTCGGAAAAGAGTTGGTAGCTCTTGATCCGGCAAACAAACCAC
CGCTGGTAGCGGTGGTTTTTTTGTTTGCAAGCAGCAGATTACGCGCAGAA
AAAAGGATCTCAAGAAGATCCTTTGATCTTTTCTACGGGGTCTGACGCT
CAGTGGAACGAAAACTCACGTTAAGGGATTTTGGTCATGAGATTATCAAA
AAGGATCTTCACCTAGATCCTTTTAAATTAAAAATGAAGTTTTAAATCAA
TCTAAAGTATATATGAGTAAACTTGGTCTGACAGTTACCAATGCTTAATC
AGTGAGGCACCTATCTCAGCGATCTGTCTATTTCGTTCATCCATAGTTGC
CTGACTCCCCGTCGTGTAGATAACTACGATACGGGAGGGCTTACCATCTG
GCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCC
TGCAACTTTATCCGCCTCCATCCAGTCTATTAATTGTTGCCGGGAAGCTA
GAGTAAGTAGTTCGCCAGTTAATAGTTTGCGCAACGTTGTTGCCATTGCT
GTAGGCATCGTGGTGTCACGCTCGTCGTTTGGTATGGCTTCATTCAGCTC
CGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCC
GCAGTGTTATCACTCATGGTTATGGCAGCACTGCATAATTCTCTTACTGT
CATGCCATCCGTAAGATGCTTTTCTGTGACTGGTGAGTACTCAACCAAGT
CATTCTGAGAATAGTGTATGCGGCGACCGAGTTGCTCTTGCCCGGCGTCA
ACACGGGATAATACCGCGCCACATAGCAGAACTTTAAAAGTGCTCATCAT
TGGAAAACGTTCTTCGGGGCGAAAACTCTCAAGGATCTTACCGCTGTTGA
GATCCAGTTCGATGTAACCCACTCGTGCACCCAACTGATCTTCAGCATCT
TTTACTTTCACCAGCGTTTCTGGGTGAGCAAAAACAGGAAGGCAAAATGC
CGCAAAAAAGGGAATAAGGGCGACACGGAAATGTTGAATACTCATACTCT
TCCTTTTTCAATATTATTGAAGCATTTATCAGGGTTATTGTCTCATGAGC
GGATACATATTTGAATGTATTTAGAAAAATAAACAAAAAGAGTTTGTAGA
AACGCAAAAAGGCCATCCGTCAGGATGGCCTTCTGCTTAATTTGATGCCT
GGCAGTTTATGGCGGGCGTCCTGCCCGCCACCCTCCGGGCCGTTGCTTCG
CAACGTTCAAATCCGCTCCCGGCGGATTTGTCCTACTCAGGAGAGCGTTC
ACCGACAAACAACAGATAAAACGAAAGGCCCAGTCTTTCGACTGAGCCTT
TCGTTTTATTTGATGCCTGGCAGTTCCCTACTCTCGCATGGGGAGACCCC
ACACTACCATCGGCGCTACGGCGTTTCACTTCTGAGTTCGGCATGGGGTC
AGGTGGGACCACCGCGCTACTGCCGCCAGGCAAATTCTGTTTTATCAGAC
CGCTTCTGCGTTCTGATTTAATCTGTATCAGGCTGAAAATCTTCTCTCAT
CCGCCAAAACAGCCAAGCTTGCATGCCTGCAGGTCGACTCTAGAGGATCC
CCAAGAAAGTCCGTCGGACAGCTTTAATAAACCCTGCACTTATCTGTTTA
GTGTGGGCGGACAAAATAGTTGGGAACTGGGAGGGGTGGAAATGGAGTTT
TTAAGGATTATTTAGGGAAGAGTGACAAAATAGATGGGAACTGGGTGTAG
CGTCGTAAGCTAATACGAAAATTAAAAATGACAAAATAGTTTGGAACTAG
ATTTCACTTATCTGGTTGGTCGACCTGCAGGGGGGGGGGGAAAGCCACG
TTGTGTCTCAAAATCTCTGATGTTACATTGCACAAGATAAAAATATATCA
TCATGAACAATAAAACTGTCTGCTTACATAAACAGTAATACAAGGGGTGT
TATGAGCCATATTCAACGGGAAACGTCTTGCTCGAGGCCGCGATTAAATT
CCAACATGGATGCTGATTTATATGGGTATAAATGGGCTCGCGATAATGTC
GGGCAATCAGGTGCGACAATCTATCGATTGTATGGGAAGCCCGATGCGCC
AGAGTTGTTTCTGAAACATGGCAAAGGTAGCGTTGCCAATGATGTTACAG
ATGAGATGGTCAGACTAAACTGGCTGACGGAATTTATGCCTCTTCCGACC
ATCAAGCATTTTATCCGTACTCCTGATGATGCATGGTTACTCACCACTGC
GATCCCCGGGAAAACAGCATTCCAGGTATTAGAAGAATATCCTGATTCAG
GTGAAAATATTGTTGATGCGCTGGCAGTGTTCCTGCGCCGGTTGCATTCG
ATTCCTGTTTGTAATTGTCCTTTTAACAGCGATCGCCTATTTCGTCTCGC
TCAGGCGCAATCACGAATGAATAACGGTTTGGTTGATGCGAGTGATTTTG
```

FIG. 9B CONT-2

```
ATGACGAGCGTAATGGCTGGCCTGTTGAACAAGTCTGGAAAGAAATGCAT
AAGCTTTTGCCATTCTCACCGGATTCAGTCGTCACTCATGGTGATTTCTC
ACTTGATAACCTTATTTTTGACGAGGGGAAATTAATAGGTTGTATTGATG
TTGGACGAGTCGGAATCGCAGACCGATACCAGGATCTTGCCATCCTATGG
AACTGCCTCGGTGAGTTTTCTCCTTCATTACAGAAACGGCTTTTTCAAAA
ATATGGTATTGATAATCCTGATATGAATAAATTGCAGTTTCATTTGATGC
TCGATGAGTTTTTCTAATCAGAATTGGTTAATTGGTTGTAACACTGGCAG
AGCATTACGCTGACTTGACGGGACGGCGGCTTTGTTGAATAAATCGAACT
TTTGCTGAGTTGAAGGATCAGATCACGCATCTTCCCGACAACGCAGACCG
TTCCGTGGCAAAGCAAAAGTTCAAAATCACCAACTGGTCCACCTACAACA
AAGCTCTCATCAACCGTGGCTCCCTCACTTTCTGGCTGGATGATGGGGCG
ATTCAGGCCTGGTATGAGTCAGCAACACCTTCTTCACGAGGCAGACCTCA
GCGCCCCCCCCCCCTGCAGGTCGACCCCACGCCCTCTTTAATACGACG
GGCAATTTGCACTTCAGAAAATGAAGAGTTTGCTTTAGCCATAACAAAAG
TCCAGTATGCTTTTTCACAGCATAACTGGACTGATTTCAGTTTACAACTA
TTCTGTCTAGTTTAAGACTTTATTGTCATAGTTTAGATCTATTTTGTTCA
    GTTTAAGACTTTATTGTCCGCCCACA
```

FIG. 9C pEM-delta -> List

DNA sequence 5926 b.p. CAGATCAATTCG ... AAGCTGTCAAAC circular pEM-delta
old name = mTm7.L166.R199
Thursday, January 9, 1992 10:58:46 PM
Read from ASCII/Citi2 file "pTRC 99A1.word"

```
       |   10      |   20      |   30      |   40      |   50       |   60      |   70      |   80      |   90      |   100
     1 CAGATCAATT CGCGCTAACT CACATTAATT GCGTTGCGCT CACTGCCCGC  TTTCCAGTCG GGAAACCTGT CGTGCCAGCT GCATTAATGA ATCGGCCAAC 100
   101 GCGCGGGGAG AGGCGGTTTG CGTATTGGGC GCCAGGGTGG TTTTTCTTTT  CACCAGTGAG ACGGGCAACA GCTGATTGCC CTTCACCGCC TGGCCCTGAG 200
   201 AGAGTTGCAG CAAGCGGTCC ACGCTGGTTT GCCCCAGCAG GCGAAAATCC  TGTTTGATGG TGGTTGACGG CGGGATATAA CATGAGCTGT CTTCGGTATC 300
   301 GTCGTATCCC ACTACCGAGA TATCCGCACC AACGCGCAGC CCGGACTCGG  TAATGGCGCG CATTGCCCCC AGCGCCATCT GATCGTTGGC AACCAGCATC 400
   401 GCAGTGGGAA CGATGCCCTC ATTCAGCATT TGCATGTTTT GTTGAAAACC  GGACATGGCA CTCCAGTCGC CTTCCCGTTC CGCTATCGGC TGAATTTGAT 500
   501 TGCGAGTGAG ATATTTATGC CAGCCAGCCA GACGCAGACG CGCCGAGACA  GAACTTAATG GGCCCGCTAA CAGCGCGATT TGCTGGTGAC CCAATGCGAC 600
   601 CAGATGCTCC ACGCCCAGTC GCGTACCGTC TTCATGGGAG AAAATAATAC  TGTTGATGGG TGTCTGGTCA GAGACATCAA GAAATAACGC CGGAACATTA 700
   701 GTGCAGGCAG CTTCCACAGC AATGGCATCC TGGTCATCCA GCGGATAGTT  AATGATCAGC CCACTGACGC GTTGCGCGAG AAGATTGTGC ACCGCCGCTT 800
   801 TACAGGCTTC GACGCCGCTT CGTTCTACCA TCGACACCAC CACGCTGGCA  CCCAGTTGAT CGGCGCGAGA TTTAATCGCC GCGACAATTT GCGACGGCGC 900
   901 GTGCAGGGCC AGACTGGAGG TGGCAACGCC AATCAGCAAC GACTGTTTGC  CCGCCAGTTG TTGTGCCACG CGGTTGGGAA TGTAATTCAG CTCCGCCATC 1000
  1001 GCCGCTTCCA CTTTTTCCCG CGTTTTCGCA GAAACGTGGC TGGCCTGGTT  CACCACGCGG GAAACGGTCT GATAAGAGAC ACCGGCATAC TCTGCGACAT 1100
  1101 CGTATAACGT TACTGGTTTC ACATTCACCA CCCTGAATTG ACTCTCTCCC  GGGCGCTATC ATGCCATACC GCGAAAGGTT TTGCACCATT CGATGGTGTC 1200
  1201 AACGTAAATG CATGCCGCTT CGCCTTCGCG CGCGAATTGA TCTGCTGCCT  CGCCGTTTC GGTGATGACG GTGAAAACCT CTGACACATG CAGCTCCCGG 1300
  1301 AGACGGTCAC AGCTTGTCTG TAAGCGGATG CCGGGAGCAG ACAAGCCCGT  CAGGGCGCGT CAGCGGGTGT TGGCGGGTGT CGGGGCGCAG CCATGACCCA 1400
  1401 GTCACGTAGC GATAGCGGAG TGTATACTGG CTTAACTATG CGGCATCAGA  GCAGATTGTA CTGAGAGTGC ACCATATGCG GTGTGAAATA CCGCACAGAT 1500
  1501 GCGTAAGGAG AAAATACCGC ATCAGGCGCT CTTCCGCTTC CTCGCTCACT  GACTCGCTGC GCTCGGTCGT TCGGCTGCGG CGAGCGGTAT CAGCTCACTC 1600
  1601 AAAGGCGGTA ATACGGTTAT CCACAGAATC AGGGGATAAC GCAGGAAAGA  ACATGTGAGC AAAAGGCCAG CAAAAGGCCA GGAACCGTAA AAAGGCCGCG 1700
  1701 TTGCTGGCGT TTTTCCATAG GCTCCGCCCC CCTGACGAGC ATCACAAAAA  TCGACGCTCA AGTCAGAGGT GGCGAAACCC GACAGGACTA TAAAGATACC 1800
  1801 AGGCGTTTCC CCCTGGAAGC TCCCTCGTGC GCTCTCCTGT TCCGACCCTG  CCGCTTACCG GATACCTGTC CGCCTTTCTC CCTTCGGGAA GCGTGGCGCT 1900
  1901 TTCTCATAGC TCACGCTGTA GGTATCTCAG TTCGGTGTAG GTCGTTCGCT  CCAAGCTGGG CTGTGTGCAC GAACCCCCCG TTCAGCCCGA CCGCTGCGCC 2000
  2001 TTATCCGGTA ACTATCGTCT TGAGTCCAAC CCGGTAAGAC ACGACTTATC  GCCACTGGCA GCAGCCACTG GTAACAGGAT TAGCAGAGCG AGGTATGTAG 2100
  2101 GCGGTGCTAC AGAGTTCTTG AAGTGGTGGC CTAACTACGG CTACACTAGA  AGGACAGTAT TTGGTATCTG CGCTCTGCTG AAGCCAGTTA CCTTCGGAAA 2200
  2201 AAGAGTTGGT AGCTCTTGAT CCGGCAAACA AACCACCGCT GGTAGCGGTG  GTTTTTTTGT TTGCAAGCAG CAGATTACGC GCAGAAAAAA AGGATCTCAA 2300
  2301 GAAGATCCTT TGATCTTTTC TACGGGGTCT GACGCTCAGT GGAACGAAAA  CTCACGTTAA GGGATTTTGG TCATGAGATT ATCAAAAAGG ATCTTCACCT 2400
  2401 AGATCCTTTT AAATTAAAAA TGAAGTTTTA AATCAATCTA AAGTATATAT  GAGTAAACTT GGTCTGACAG TTACCAATGC TTAATCAGTG AGGCACCTAT 2500
  2501 CTCAGCGATC TGTCTATTTC GTTCATCCAT AGTTGCCTGA CTCCCCGTCG  TGTAGATAAC TACGATACGG GAGGGCTTAC CATCGGTGCC CAGTGCTGCA 2600
  2601 ATGATACCGC GAGACCCACG CTCACCGGCT CCAGATTTAT CAGCAATAAA  CCAGCCAGCC GGAAGGGCCG AGCGCAGAAG TGGTCCTGCA ACTTTATCCG 2700
  2701 CCTCCATCCA GTCTATTAAT TGTTGCCGGG AAGCTAGAGT AAGTAGTTCG  CCAGTTAATA GTTTGCGCAA CGTTGTTGCC ATTGCTGTAG GCATCGTGGT 2800
  2801 GTCACGCTCG TCGTTTGGTA TGGCTTCATT CAGCTCCGGT TCCCAACGAT  CAAGGCGAGT TACATGATCC CCCATGTTGT GCAAAAAAGC GGTTAGCTCC 2900
  2901 TTCGGTCCTC CGATCGTTGT CAGAAGTAAG TTGGCCGCAG TGTTATCACT  CATGGTTATG GCAGCACTGC ATAATTCTCT TACTGTCATG CCATCCGTAA 3000
  3001 GATGCTTTTC TGTGACTGGT GAGTACTCAA CCAAGTCATT CTGAGAATAG  TGTATGCGGC GACCGAGTTG CTCTTGCCCG GCGTCAACAC GGGATAATAC 3100
  3101 CGCGCCACAT AGCAGAACTT TAAAAGTGCT CATCATTGGA AAACGTTCTT  CGGGGCGAAA ACTCTCAAGG ATCTTACCGC TGTTGAGATC CAGTTCGATG 3200
  3201 TAACCCACTC GTGCACCCAA CTGATCTTCA GCATCTTTTA CTTTCACCAG  CGTTTCTGGG TGAGCAAAAA CAGGAAGGCA AAATGCCGCA AAAAAGGGAA 3300
  3301 TAAGGGCGAC ACGGAAATGT TGAATACTCA TACTCTTCCT TTTTCAATAT  TATTGAAGCA TTTATCAGGG TTATTGTCTC ATGAGCGGAT ACATATTTGA 3400
  3401 ATGTATTTAG AAAAATAAAC AAAAAGAGTT TGTAGAAACG CAAAAAGGCC  ATCCGTCAGG ATGGCCTTCT GCTTAATTTG ATGCCTGGCA GTTTATGCG 3500
  3501 GCCGTCCTGC CCGCCACCCT CCGGGCCGTT GCTTCGCAAC GTTCAAATCC  GCTCCCGGCG GATTTGTCCT ACTCAGGAGA GCGTTCACCG ACAAACAACA 3600
  3601 GATAAAACGA AAGGCCCAGT CTTTCGACTG AGCCTTTCGT TTTATTTGAT  GCCTGGCAGT TCCCTACTCT CGCATGGGGA GACCCCACAC TACCATCGGC 3700
  3701 GCTACGCGCT TTCACTTCTG AGTTCGGCAT GGGGTCAGGT GGGACCACCG  CGCTACTGCC GCCAGGCAAA TTCTGTTTTA TCAGACCGCT TCTGCGTTCT 3800
  3801 GATTTAATCT GTATCAGGCT GAAAATCTTC TCTCATCCGC CAAAACAGCC  AAGCTTGCAT GCCTGCAGGT CGACTCTAGA GGATCCCCAA GAAAGTCCGT 3900
  3901 CGGACAGCTT TAATAACCCC TGCACTTATC TGTTTAGTGT GGGAGCACAA  AATATTGGAG AACTGGGAGG GGTGGAAATA GAGTTTTTAA GGATTATTTA 4000
  4001 GGGAAGAGTG ACAAAAATAGA TGGGAACTGG GTGTAGCGTC GTAAGCTAAT  ACGAAAATTA AAAATGACAA AATAGTTTGG AACTAGATTT CACTTATCTG 4100
  4101 GTTGGTCGAC CTGCAGGGGG GGGGGGGAAA GCCACGTGGT GTCTCAAAAT  CTCTGATGTT ACATTGCACA AGATAAAAAT ATATCATCAT GAACAATAAA 4200
  4201 ACTGTCTGCT TACATAAACA GTAATACAAG GGGTGTTATG AGCCATATTC  AACGGGAAAC GTCTTGCTCG AGGCCGCGAT TAAATTCCAA CATGGATGCT 4300
  4301 GATTTATATG GGTATAAATG GGCTCGCGAT AATGTCGGGC AATCAGGTGC  GACAATCTAT CGATTGTATG GGAAGCCCGA TGCGCCAGAG TTGTTTCTGA 4400
  4401 AACATGGCAA AGGTAGCGTT GCCAATGATG TTACAGATGA GATGGTCAGA  CTAAACTGGC TGACGGAATT TATGCCTCTT CCGACCATCA AGCATTTTAT 4500
  4501 CCGTACTCCT GATGATGCAT GGTTACTCAC CACTGCGATC CCCGGGAAAA  CAGCATTCCA GGTATTAGAA GAATATCCTG ATTCAGGTGA AAATATTGTT 4600
  4601 GATGCGCTGG CAGTGTTCCT GCGCCGGTTG CATTCGATTC CTGTTTGTAA  TTGTCCTTTT AACAGCGATC GCGTATTTCG TCTCGCTCAG GCGCAATCAC 4700
  4701 GAATGAATAA CGGTTTGGTT GATGCGAGTG ATTTTGATGA CGAGCGTAAT  GGCTGGCCTG TTGAACAAGT CTGGAAAGAA ATGCATAAGC TTTTGCCATT 4800
  4801 CTCACCGGAT TCAGTCGTCA CTCATGGTGA TTTCTCACTT GATAACCTTA  TTTTTGACGA GGGGAAATTA ATAGGTTGTA TTGATGTTGG ACGAGTCGGA 4900
  4901 ATCGCAGACC GATACCAGGA TCTTGCCATC CTATGGAACT GCCTCGGTGA  GTTTTCTCCT TCATTACAGA AACGGCTTTT TCAAAAATAT GGTATTGATA 5000
  5001 ATCCTGATAT GAATAAATTG CAGTTTCATT TGATGCTCGA TGAGTTTTTC  TAATCAGAAT TGGTTAATTG GTTGTAACAC TGGCAGAGCA TTACGCTGAC 5100
  5101 TTGACGGGAC GGCGGCTTTG TTGAATAAAT CGAACTTTTG GATCAGATC ACGCATCTTC CCGACAACGC AGACCGTTCC GTGGCAAAGC 5200
  5201 AAAAGTTCAA AATCACCAAC TGGTCCACCT ACAACAAAGC TCTCATCAAC  CGTGGCTCCC TCACTTTCTG GCTGGATGAT GGGGCGATTC AGGCCTGGTA 5300
  5301 TGAGTCAGCA ACACCTTCTT CACGAGGCAG ACCTCAGCGC CCCCCCCCCC  CTGCAGGTCG ACCCCACCCC CCTCTTTAAT ACGACGGGCA ATTTGCACTT 5400
  5401 CAGAAAATGA AGAGTTTGCT TTAGCCATAA CAAAAGTCCA GTATGCTTTT  TCACAGCATA ACTGGACTGA TTTCAGTTTA CAACTATTCT GTCTAGTTTA 5500
  5501 AGACTTTATT GTCATAGTTT AGATCTATTT TGTTCAGTTT AAGACTTTAT  TGTCCGCACA CATTTAGAC AATTCGGTGT TAGTTTCAGC AAGCAAACAT 5600
  5601 TAACCATAGC TAATGATTTA TAGCCATATT AACCATTGGG GTACCGAGCT  CGAATTCCAT GGTCTGTTTC CTGTGTGAAA TTGTTATCCG CTCACAATTC 5700
  5701 CACACATTAT ACGAGCCGGA TGATTAATTG TCAACAGCTC ATTTCAGAAT  ATTTGCCAGA ACCGTTATGA TGTCGGCGCA AAAACATTA TCCAGAACGG 5800
  5801 GAGTGCGCCT TGAGCGACAC GAATTATGCA GTGATTTACG ACCTGCACAG  CCATACCACA GCTTCCGATG GCTGCCTGAC GCCAGAAGCA TTGGTGCACC 5900
  5901 GTGCAGTCGA TGATAAGCTG TCAAAC                                                                                  5926
       |   10      |   20      |   30      |   40      |   50       |   60      |   70      |   80      |   90      |   100
```

FIG. 10A

```
GAATTCCGGATGAGCATTCATCAGGCGGGCAAGAATGTGAATAAAGGCCG
GATAAAACTTGTGCTTATTTTTCTTTACGGTCTTTAAAAAGGCCGTAATA
TCCAGCTGAACGGTCTGGTTATAGGTACATTGAGCAACTGACTGAAATGC
CTCAAAATGTTCTTTACGATGCCATTGGATATATCAACGGTGGTATATC
CACTGATTTTTTTCTCCATTTTAGCTTCCTTAGCTCCTGAAAATCTCGAT
AACTCAAAAAATACGCCCGGTAGTGATCTTATTTCATTATGGTGAAAGTT
GGAACCTCTTACGTGCCGATCAACGTCTCATTTTCGCCAAAAGTTGGCCC
AGGGCTTCCCGGTATCAACAGGGACACCAGGATTTATTTATTCTGCGAAG
TGATCTTCCGTCACAGGTATTTATTCGGCGCAAAGTGCGTCGGGTGATGC
TGCCAACTTACTGATTTAGTGTATGATGGTGTTTTGAGGTGCTCCAGTG
GCTTCTGTTTCTATCAGCTGTCCCTCCTGTTCAGCTACTGACGGGGTGGT
GCGTAACGGCAAAAGCACCGCCGGACATCAGCGCTAGCGGAGTGTATACT
GGCTTACTATGTTGGCACTGATGAGGGTGTCAGTGAAGTGCTTCATGTGG
CAGGAGAAAAAAGGCTGCACCGGTGCGTCAGCAGAATATGTGATACAGGA
TATATTCCGCTTCCTCGCTCACTGACTCGCTACGCTCGGTCGTTCGACTG
CGGCGAGCGGAAATGGCTTACGAACGGGGCGGAGATTTCCTGGAAGATGC
CAGGAAGATACTTAACAGGGAAGTGAGAGGGCCGCGGCAAAGCCGTTTTT
CCATAGGCTCCGCCCCCTGACAAGCATCACGAAATCTGACGCTCAAATC
AGTGGTGGCGAAACCCGACAGGACTATAAAGATACCAGGCGTTTCCCCTG
GCGGCTCCCTCGTGCGCTCTCCTGTTCCTGCCTTTCGGTTTACCGGTGTC
ATTCCGCTGTTATGGCCGCGTTTGTCTCATTCCACGCCTGACACTCAGTT
CCGGGTAGGCAGTTCGCTCCAAGCTGGACTGTATGCACGAACCCCCCGTT
CAGTCCGACCGCTGCGCCTTATCCGGTAACTATCGTCTTGAGTCCAACCC
GGAAAGACATGCAAAAGCACCACTGGCAGCAGCCACTGGTAATTGATTTA
GAGGAGTTAGTCTTGAAGTCATGCGCCGGTTAAGGCTAAACTGAAAGGAC
AAGTTTTGGTGACTGCGCTCCTCCAAGCCAGTTACCTCGGTTCAAAGAGT
TGGTAGCTCAGAGAACCTTCGAAAAACCGCCCTGCAAGGCGGTTTTTCG
TTTTCAGAGCAAGAGATTACGCGCAGACCAAAACGATCTCAAGAAGATCA
TCTTATTAATCAGATAAAATATTTCTAGATTTCAGTGCAATTTATCTCTT
CAAATGTAGCACCTGAAGTCAGCCCCATACGATATAAGTTGTAATTCTCA
TGTTTGACAGCTTATCATCGGATGGATCTGAAATTGTAAACGTTAATATT
TTGTTAAATTCGCGTTAAATTTTTGTTAAATCAGCTCATTTTTTAACCAA
TAGGCCGAAATCGGCAAAATCCCTTATAAATCAAAAGAATAGACCGAGAT
AGGGTTGAGTGTTGTTCCAGTTTGGAACAAGAGTCCACTATTAAAGAACG
TGGACTCCAACGTCAAAGGGCGAAAAACCGTCTATCAGGGCGATGGCCCA
CTACGTGAACCATCACCCTAATCAAGTTTTTTGGGGTCGAGGTGCCGTAA
AGCACTAAATCGGAACCCTAAAGGGAGCCCCCGATTTAGAGCTTGACGGG
GAAAGCCGGCGAACGTGGCGAGAAAGGAAGGGAAGAAAGCGAAAGGAGCG
GGCGCTAGGGCGCTGGCAAGTGTAGCGGTCACGCTGCGCGTAACCACCAC
ACCCGCCGCGCTTAATGCGCCGCTACAGGGCGCGTCAGATCCCATCGATA
AGCTTTAATGCGGTAGTTTATCACAGTTAAATTGCTAACGCAGTCAGGCA
CCGTGTATGAAATCTAACAATGCGCTCATCGTCATCCTCGGCACCGTCAC
CCTGGATGCTGTAGGCATAGGCTTGGTTATGCCGGTACTGCCGGGCCTCT
TGCGGGATATCGTCCATTCCGACAGCATCGCCAGTCACTATGGCGTGCTG
CTAGCGCTATATGCGTTGATGCAATTTCTATGCGCACCCGTTCTCGGAGC
ACTGTCCGACCGCTTTGGCCGCCGCCCAGTCCTGCTCGCTTCGCTACTTG
GAGCCACTATCGACTACGCGATCATGGCGACCACACCCGTCCTGTGGATC
CGCTGGCGAAAGGGGGATGTGCTGCAAGGCGATTAAGTTGGGTAACGCCA
GGGTTTTCCCAGTCACGACGTTGTAAAACGACGGCCAGTGAATTGCGGCC
GCCCTGCAAGGAAGGGAATGTCGCCAACAGCGAAGAGAGTTGGGCAACGG
ATGTGCTGGTGGAGGTGATCGCCTCCTGATGATGAGCCGCTCCCGATGTG
```

FIG. 10A (CONT)-1

```
GTGTCGGGAGCGGTATTTTCTATAAAACTTACCGCTTATTTGAGATATTC
ATCGAAAATGTCGAGTAATTCTTGATGTATACACGGCCATTCCTGACCTA
AATTGACGGTACACAAGCCAATATCGAAGCCATTAATTTTATAACGATGT
TTCACTGCGGTATCTACGTGGGGATATATTAATAACCCCCCTATGTTTTC
GCCATTTTCAGGCTTTAACGACCATAAGTAATTCATCAGTTGATAAAGAT
TTTGCGAATGAAATTTTTCTGTTCCCATTCGTCGTGAAAAAATGCTCTTA
TAGTATTTGGCGTCAACGATAAGTATTTTTTCTGATGAGCGAATGGTGAT
GTCAGTTTCCATTCGAGGTAACAAATTAAGTGACTGATCCGATATACTCG
ATGCATCCATTTTAAATAAGAGCGGGTTGTGTTTGCAGACGTTAATTCA
CGACGGCAAAATTCATAAAGAAACTTTTGATAAAGTAATGACATCTCTTT
TTCGTTTCTTTCAAAATCATAGAAACGGTAGTGTCCTTTGTTTTGACCTG
GAATAGAATTATTGACGATGAATTTGCAGACACTGATAACGAATTTATAA
TAACGCGTATTTTTCCGCCATTCAGATAGCTGAAATGCTGCGGAGTTAA
ATGAAGAGTGCTAATGCCCGGTAATTTTCTATAAAGTGAACGAGCTTCAT
CTCTGATAGTTGAATTTAACTTTTCATGCTTAATTAATATGGCTAATGTG
CTTTTTATAATTCGGTTAGCCAGCGTGTCTTCATTAAGCATATCAAAAGT
ACTGACGGTTTTCCCATGATTAAGATGGAAGCCGCGTATTGTTTTAGCAA
ACTCTATTCGCCCTTTGATGCCAGGAATGATCTCGGTGTTAGGATTGTAA
TCAAGCTCAAGCCCTCGGCGTGAAAGCTGTAAAACCCCTTTATTTAATAC
ATACCCCAGGATATCAAGAAGATTGTTACCGGGTATGGCTTCAAGGTTTG
CCTGCTTAATTTCCTGTAAATAACCCCATGCATAGGTAAGCATGTAATAG
ATATTACGGACAGGTATCACGGCTGTTCCACTATGAGTCCCCTAATAAT
TTGTTGGTCCATTTCTGTTGTTTATAGGGGTCATCAAAGAAATATTCTTC
GAGTAAAGGGGCGATATCCGTCATCACAATTTCATTAAGCCATTGCGTAT
CCGGAGAGGTGCCATCTTCCAACCCACAGCAGAAGTAACTATGCCCAATG
CGGAATCcTTTCCCAAGGATAGTGGCCTCTTTGCTGATTTCCTGGTTCAA
CTCGTTCATTTTTTGGCATAAAGACTCAACAAATGAAGGTTCTGCTTTTT
TATTCAGTAAAAAATTCCGGAACTGTGGTGTATCAAAACCTGGCTCAATA
TCTATGAAAGAAAATCGTCTGCGTAGGGCATAGTCAACAACGGCCAGAGA
GCGATCGGCAGTATTCATTAAACCGATGATATAAACATTCTCCGGGACAT
AGAATCGTTCTTCATCGTTTTCGGAGTAGGTTAGGGGAACAGACCAGTTT
TCACCTCGTTTATCATGTTCCATTAACATCATCACTTCGCCAAATACTTT
ACTGAGATTGGCACGATTGATTTCATCTATAATAAAAATATACTTTTTCT
CTGGCTGCTCTTTAGCTTGCTGACAAAAATTGTAAAATATGCCGTCTTTA
CGTCGGAAGCCGACGCCATTCGGACGATAGCCCTGTATAAAATCCTCATA
GCTATAAGATTGATGGAACTGAACCATATTGACGCGTTGCGGAGCCTTTT
CTCCTGTCAGCAAGTAAGCCAGACGGCGTGCAACAAAGGTTTTTCCAACG
CCGGCGGCCCCTGGAGGATAATATTTTTTTTGATGGTTAATCGTTTGAG
TATCGTCTCTATTGTGGTTTCAGGGATAAACAAATCATTTAACGCATCTT
CCAGACAGTATGATTCAGTTTTTGACATAGGTGGAATAACACTCTTGCCA
GAATTAAATATTAATTTATAGTCGTTGATTATGTTGTCCAGCATAGAGGC
AAATCGGGTGTAATCAATACCCTGTGAGACTTTTTGGGAACAGGCGTAAT
AGGACTGTCCGTATTTTTAGGATATACACCCGAAGTTGCCTGAAAATAC
TCTGCGATTGTTTTAGGTATGTCTGAAGAGAACTGCCATTGGGCATGTGG
TTCATTCGTGTCGCTTATACCATAAGCCAAAACCAACTCATCAAAATCTT
TATAATAGAGAATAACGGGATATATACCGTTAGAAGCTTCCTGACCTTCT
CCAAGAAATGCAAACCAGGGAATAGACGTAAAATTACCATAACCGAAACT
CAATTTTACTCGCAGGTTACGGTAAGACGTTGGATAATCTTTAGTGGATT
GCGAACGTTGTTGCTGTGCTTGCTTAATAAATTTTTCAATCCAGGGTTGA
ATAGATTCCATAAGATATGCCTTCCTCATTGCTAAGCCTCTATTATCGCT
TTCGCAACGTACTGAAACAATAGATTTTACTGCAAAATCAGACTGGTAA
ATATTTACTGAGGGGAAAGTTTCTATTGAGTCAGTGGAAGGCTCCCGGT
GGTTAACCGGGAGTAAACGCTGTTACGCGACTTTCTGTTTACCGGCAATC
ACTCCAATAAACGCCTGCACCTGCTTTTGTTTACGCGCCGACAGTTTGCA
```

FIG. 10A (CONT)-2

```
CACCTGGCGTAGCGACTGCATCAGTTCGCTCTCCTCGGCGGCGGGTGGTT
GGGCGGTGAGGACAATACAGCCTTCCATCACTTTGACATCTACCGCCGTG
CCAGTGGCAAAACCGGCGGCTTCCAGCCACTGACCTTTCAGGGTGATGGC
GGGAATACGGCTGTAATCCGGGTAGCGACTCGCATAACCGACGGTGACAT
GACGGTTATTTGCCGGGGAGACTTCTGCTTCGAACGGTTGTGCAATAGAA
TGCGTGTCAGTCATAACTGCTATTCTCCAGGAATAGTGATTGTGATTAGC
GATGCGGGTGTGTTGGCGCACATCCGCACCGCGCTAAATACCTGTATATA
TCATCAGTAAATATGGGGAAAGTCCAGCTAAAAATAGAATAAAATGGGCA
ATTTCTGGAATGATTTAAATATATTTATGTGGGTTATGATTGGCGTGAAA
TAATAAAAAGCGCACCGGAAAGGTGCGCCAGAAAATAATGTTCAGGATTT
TTTACGTGAGGCTTTTTTACCCCCGCTAGCTGCGCGTTCAGCTTTGATTT
TTTCCAGCAACGCGGCGGCGCTGTTTTCTCCGCTGATCAAATCCGGGTTT
TCGGCCCGCCACTGGGCGGTAAGTTCACCACGGAACGCTTTTGCCAGGAT
GGATTGCGTCAGGTTGTTGACGCGGGCTAAGGCGTTGTTGACCTGTTTTT
CTATGGTGTCGGCGTAGGCGAAGAGTTGCTCGACGCGGCGAACGATTTCG
GCTTGTTCTTTTACTGGAGGTAATAAAACAACTTGGGATTTGATATCTTT
TCCTGAAATACCTTTTTGACCAGAAGTTGTTTTCACGCAGTTCATCATTG
CATTTCGTGCTGAGGGGGATGAAAAAAATATTTCGATATATTCTGGTAAA
GCATCTTTGGTTAATCGAGCTCGAATAAGTTTATCAGGATATAGCAAATT
TTGATGTTGTAATTTTTTCAATAACCCACAAACACCAACAAATTCTAAAC
TTCCGTTATAGCGAGTAAATAAAAGATCTCCATCTTGTAATTTGTGGCGG
TTTAGTTCACTTTCTGAACATTCTAGAGTCGACCTGCAGGCATGCAAGCT
TGGCGTAATCATGGTCATAGCTGTTTCCTGTGTGAAATTGTTATCCGCTC
ACAATTCCACACAACATACGAGCCGGAAGCATAAAGTGTAAAGCCTGGGG
TGCCTAATGAGTGAGCTAACTCACATTAATTGCGTTGCGCTCACTGCCCG
CTTTCCAGTCGGGAAACCTGTCGTGCCAGCGGATCCTCTACGCCGGACGC
ATCGTGGCCGGCATCACCGGCGCCACAGGTGCGGTTGCTGGCGCCTATAT
CGCCGACATCACCGATGGGGAAGATCGGGCTCGCCACTTCGGGCTCATGA
GCGCTTGTTTCGGCGTGGGTATGGTGGCAGGCCCCGTGGCCGGGGGACTG
TTGGGCGCCATCTCCTTGCATGCACCATTCCTTGCGGCGGCGGTGCTCAA
CGGCCTCAACCTACTACTGGGCTGCTTCCTAATGCAGGAGTCGCATAAGG
GAGAGCGTCGACCGATGCCCTTGAGAGCCTTCAACCCAGTCAGCTCCTTC
CGGTGGGCGCGGGGCATGACTATCGTCGCCGCACTTATGACTGTCTTCTT
TATCATGCAACTCGTAGGACAGGTGCCGGCAGCGCTCTGGGTCATTTTCG
GCGAGGACCGCTTTCGCTGGAGCGCGACGATGATCGGCCTGTCGCTTGCG
GTATTCGGAATCTTGCACGCCCTCGCTCAAGCCTTCGTCACTGGTCCCGC
CACCAAACGTTTCGGCGAGAAGCAGGCCATTATCGCCGGCATGGCGGCCG
ACGCGCTGGGCTACGTCTTGCTGGCGTTCGCGACCCGAGGCTGGATGGCC
TTCCCCATTATGATTCTTCTCGCTTCCGGCGGCATCGGGATGCCCGCGTT
GCAGGCCATGCTGTCCAGGCAGGTAGATGACGACCATCAGGGACAGCTTC
AAGGATCGCTCGCGGCTCTTACCAGCCTAACTTCGATCATTGGACCGCTG
ATCGTCACGGCGATTTATGCCGCCTCGGCGAGCACATGGAACGGGTTGGC
ATGGATTGTAGGCGCCGCCCTATACCTTGTCTGCCTCCCCGCGTTGCGTC
GCGGTGCATGGAGCCGGGCCACCTCGACCTGAATGGAAGCCGGCGGCACC
TCGCTAACGGATTCACCACTCCAAGAATTGGAGCCAATCAATTCTTGCGG
AGAACTGTGAATGCGCAAACCAACCCTTGGCAGAACATATCCATCGCGTC
CGCCATCTCCAGCAGCCGCACGCGGCGCATCTCGGGCAGCGTTGGGTCCT
GGCCACGGGTGCGCATGATCGTGCTCCTGTCGTTGAGGACCCGGCTAGGC
TGGCGGGGTTGCCTTACTGGTTAGCAGAATGAATCACCGATACGCGAGCG
AACGTGAAGCGACTGCTGCTGCAAAACGTCTGCGACCTGAGCAACAACAT
GAATGGTCTTCGGTTTCCGTGTTTCGTAAAGTCTGGAAACGCGGAAGTCC
CCTACGTGCTGCTGAAGTTGCCCGCAACAGAGAGTGGAACCAACCGGTGA
TACCACGATACTATGACTGAGAGTCAACGCCATGAGCGGCCTCATTTCTT
ATTCTGAGTTACAACAGTCCGCACCGCTGCCGGTAGCTCCTTCCGGTGGG
```

FIG. 10A (CONT)-3

```
CGCGGGGCATGACTATCGTCGCCGCACTTATGACTGTCTTCTTTATCATG
CAACTCGTAGGACAGGTGCCGGCAGCGCCCAACAGTCCCCGGCCACGGG
GCCTGCCACCATACCCACGCCGAAACAAGCGCCCTGCACCATTATGTTCC
GGATCTGCATCGCAGGATGCTGCTGGCTACCCTGTGGAACACCTACATCT
GTATTAACGAAGCGCTAACCGTTTTATCAGGCTCTGGGAGGCAGAATAA
ATGATCATATCGTCAATTATTACCTCCACGGGGAGAGCCTGAGCAAACTG
GCCTCAGGCATTTGAGAAGCACACGGTCACACTGCTTCCGGTAGTCAATA
AACCGGTAAACCAGCAATAGACATAAGCGGCTATTTAACGACCCTGCCCT
GAACCGACGACCGGGTCGAATTTGCTTTCGAATTTCTGCCATTCATCCGC
TTATTATCACTTATTCAGGCGTAGCAACCAGGCGTTTAAGGGCACCAATA
ACTGCCTTAAAAAAATTACGCCCCGCCCTGCCACTCATCGCAGTACTGTT
GTAATTCATTAAGCATTCTGCCGACATGGAAGCCATCACAGACGGCATGA
TGAACCTGAATCGCCAGCGGCATCAGCACCTTGTCGCCTTGCGTATAATA
TTTGCCCATGGTGAAAACGGGGCGAAGAAGTTGTCCATATTGGCCACGT
TTAAATCAAAACTGGTGAAACTCACCCAGGGATTGGCTGAGACGAAAAAC
ATATTCTCAATAAACCCTTTAGGGAAATAGGCCAGGTTTTCACCGTAACA
CGCCACATCTTGCGAATATATGTGTAGAAACTGCCGGAAATCGTCGTGGT
ATTCACTCCAGAGCGATGAAAACGTTTCAGTTTGCTCATGGAAAACGGTG
TAACAAGGGTGAACACTATCCCATATCACCAGCTCACCGTCTTTCATTGC
CATACG
```

FIG. 10B

FIG. 13
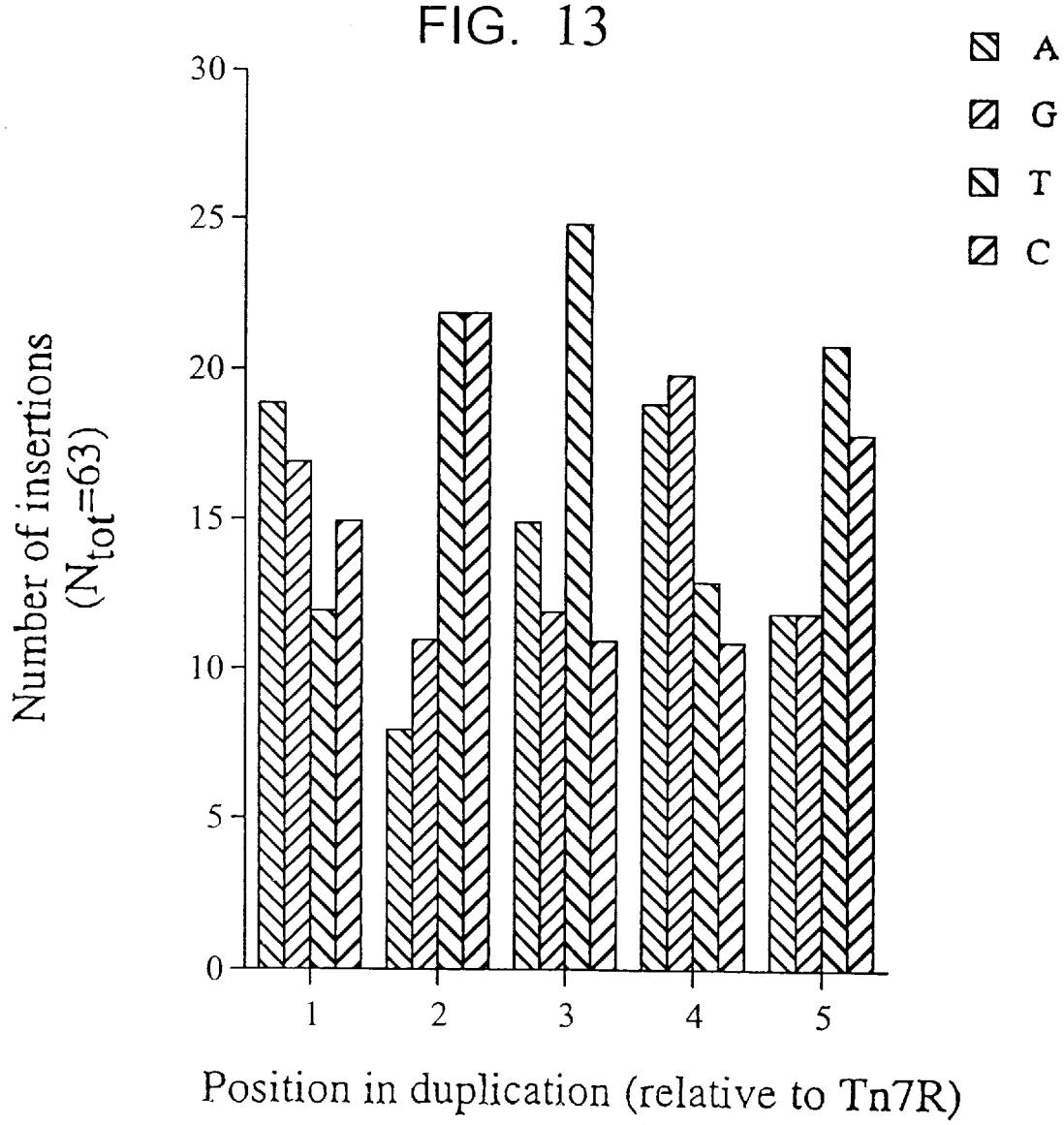

DNA Strider™ 1.2 ### Monday,April13,1998 4:15:21 PM tns gene C -> List

DNA sequence 1670 b.p. ATGAGTGCTACC ... AGCAGGTTAGCC linear

```
        |    10     |    20     |    30     |    40     |    50     |    60     |    70     |    80     |    90     |   100
   1 ATGAGTGCTA CCCGGATTCA AGCAGTTTAT CGTGATACGG GGGTAGAGGC TTATCGTGAT AATCCTTTTA TCGAGGCCTT ACCACCATTA CAAGAGTCAG  100
 101 TGAATAGTGC TGCATCACTG AAATCCTCTT TACAGCTTAC TTCCTCTGAC TTGCAAAAGT CCCGTGTTAT TTGCAGTTCA CAGAGCTCAT ACCATTGTC GTATTCCAGA  200
 201 TGACTATTTT CAGCCATTAG GTACGCATTT GCTACTAAGT GAGCGTATTT CGTTCATGAT TCGAGGTGGC TACGTAGGCA GAAATCCTAA AACAGGAGAT  300
 301 TTACAAAAGC ATTTACAAGA TGGTTGGTTG GGGAGAGACGA CGTGTTCAAA CGGGAGAGTT GGAGACATTT CGCTTTGAGG TACGCACGATC TACGGCACAA AGCTTATTGT  400
 401 TAATTGGTTG TTCTGGTAGT GCTCGCATAA TGGTTCGCTA AAAGAAATCT GCCACGTATC CTCAGTGAT TTGGATCGAG TTGGATCGAG CCTTGGGCTC TAGAGCAGGT  500
 501 GGTGTATTTG AAAATAGACT GCTCGCATAA TCATGGTATA GAAACCATGT TGGCTTTGAT GTCCAAATA GCCAATGCAC ATGCTTTAGG GTTGTTGGTT ATTGATGAAA  600
 601 CGTCGTTATG AAGCCGCTCT CGTTCGGGTG GATCTCAAGA GATGCTGAAC TTTTTGTGA CGATGGTGAA TATTATTGGC GTACCAGTGA TGTTGATTGG  700
 701 TTCAGCATTT AAGCCCTAAA GCACGAGAGA TTTTTGAGGC TGATTTGCGG TCTGCACGTA GAGGGCAGG GTTTGGAGCT ATATTCTGGA ATCCTATACA ACAAACGCAA  800
 801 TACCCCTAAA GCACGAGAGA GTGGATCAAC TTTACGGATA TCTCTCTGGG TCTGCACGTA ATTACAGCTT TTACGGATA TCTCTCGG AAGATGCGCT GTTATCGGAT GAGGTCCGTG  900
 901 CGTGGAAAGC TGAGCTAAGC CAAGGAGTGA TGGACATTGT AGTAAAACTT TTGTACTCG CTCAGCTCCG TGGCCTAGCT TTAGGCAATG AGGGTATTAC  1000
1001 ATGTGGTTA TTGGGGCAAG TGTATCAAGA TGAGTTAACC AACTTCAGCT CCATGACCC AGATATCGCA GGCATTACGC TCGGGTATCC CAGAACGCAT TGCTCGTTAT  1100
1101 CGCTGGTTTA TCGTTCCCGA GATTGATAAA CGGTTAATCC AACTTCAGCT GAAAGAGGAT AGATATCGCA GCGATACAAG AACAAACACC TCCCACTATT AAAAAAGCGT TTAGCCAGAA  1200
1201 TCTGATCTAG TCGTTCCCGA GATTGATAAA CGTCATTTAT ATCTGATGCT GAAAGAGGAT AGATATCGCA GCGATACAAG TCCCACTATT AAAAAAGCGT TTAGCCAGAA  1300
1301 AGTTAGATAC CGAAGATCAG CGTTACTGCC TCTTGTTTTG CAGTGGTTGA TGGAAGGCGA AACGGTAGTG TCAGAACTAG TCGAAACTAG AAAAGCCCTC CAAGAGTAAA  1400
1401 TCCAACGATG ACAAGACAAA AGTTACTGCC AGTCAAGCCC AGGACTGGG ATAGCTTGCC TGATACGGAT TTACGTTATA TCTATTCACA AGCGCCAACCT GAAAAAACCA  1500
1501 AAGGTTTCGG CTATAAAGGT AGTCAAGCCC AGGACTGGG ATAGCTTGCC TGATACGGAT TTACGTTATA TCTATTCACA AGCGCCAACCT GAAAAAACCA  1600
1601 TGCATGAACG GTTAAAAGGG AAAGGGGTAA TAGTGGATAT GGCGAGCTTA TTTAAACAAG CAGGTTAGCC                                              1670
        |    10     |    20     |    30     |    40     |    50     |    60     |    70     |    80     |    90     |   100
``` nucleotide sequence TnsC

FIG. 18A

DNA Strider™ 1.2    ###    Monday, April 13, 1998    4:16:55 PM

Tns protein C -> List

Protein sequence    556 a.a.    MSATRIQAVYRD ... VDMASLFKQAGZ

```
         |    10     |    20     |    30     |    40     |    50     |    60     |    70     |    80     |    90     |   100
  1 MSATRIQAVY RDTGVEAYRD NPFIEALPPL QESVNSAASL KSSLQLTSSD LQKSRVIRAH TICRIPDDYF QPLGTHLLLS ERISVMIRGG YVGRNPKTGD 100
101 LQKHLQNGYE RVQTGELETF RFEEARSTAQ SLLLIGCSGS GKTTSLHRIL ATYPQVIYHR ELNVEQVVYL KIDCSHNGSL KEICLNFFRA LDRALGSNYE 200
201 RRYGLKRHGI EIMRALMSQI ANAHALGLIV IDEIQHLSRS RSGGSQEMLN FFVTMVNIIG VPVMLIGTPK AREIFEADLR SARRGAGFGA IFWDPIQQTQ 300
301 RGKPNQEWIA FTDNLMQLQL LQRKDALLSD EVRDVWYELS QGVMDIVVKL FVLAQLRALA LGNERITAGL LRQVYQDELK PVHPMLEALR SGIPERIARY 400
401 SDLVPSIEK FLIQLQLDIA AIQEQTPEEK ALQELDTEDQ RHLYLMLKED YDSSLLIPTI KKAFSQNPTM TRQKLLPLVL QWLMEGETVV SELEKPSKSK 500
501 KVSAIKVVKP SDWDSLPDTD LRYIYSQRQP EKTMHERLKG KGVIVDMASL FKQAGZ                                              556

|    10     |    20     |    30     |    40     |    50     |    60     |    70     |    80     |    90     |   100
``` amino acid sequence TnsC

FIG. 18B

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1670 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1668

(xi) SEQUENCE DESCRIPTION: SEQ ID NO:1:

```
ATG AGT GCT ACC CGG ATT CAA GCA GTT TAT CGT GAT ACG GGG GTA GAG      48
Met Ser Ala Thr Arg Ile Gln Ala Val Tyr Arg Asp Thr Gly Val Glu
 1               5                  10                  15

GCT TAT CGT GAT AAT CCT TTT ATC GAG GCC TTA CCA CCA TTA CAA GAG      96
Ala Tyr Arg Asp Asn Pro Phe Ile Glu Ala Leu Pro Pro Leu Gln Glu
             20                  25                  30

TCA GTG AAT AGT GCT GCA TCA CTG AAA TCC TCT TTA CAG CTT ACT TCC     144
Ser Val Asn Ser Ala Ala Ser Leu Lys Ser Ser Leu Gln Leu Thr Ser
         35                  40                  45

TCT GAC TTG CAA AAG TCC CGT GTT ATC AGA GCT CAT ACC ATT TGT CGT     192
Ser Asp Leu Gln Lys Ser Arg Val Ile Arg Ala His Thr Ile Cys Arg
 50                  55                  60

ATT CCA GAT GAC TAT TTT CAG CCA TTA GGT ACG CAT TTG CTA CTA AGT     240
Ile Pro Asp Asp Tyr Phe Gln Pro Leu Gly Thr His Leu Leu Leu Ser
 65                  70                  75                  80

GAG CGT ATT TCG GTC ATG ATT CGA GGT GGC TAC GTA GGC AGA AAT CCT     288
Glu Arg Ile Ser Val Met Ile Arg Gly Gly Tyr Val Gly Arg Asn Pro
                 85                  90                  95

AAA ACA GGA GAT TTA CAA AAG CAT TTA CAA AAT GGT TAT GAG CGT GTT     336
Lys Thr Gly Asp Leu Gln Lys His Leu Gln Asn Gly Tyr Glu Arg Val
             100                 105                 110

CAA ACG GGA GAG TTG GAG ACA TTT CGC TTT GAG GAG GCA CGA TCT ACG     384
Gln Thr Gly Glu Leu Glu Thr Phe Arg Phe Glu Glu Ala Arg Ser Thr
         115                 120                 125

GCA CAA AGC TTA TTG TTA ATT GGT TGT TCT GGT AGT GGG AAG ACG ACC     432
Ala Gln Ser Leu Leu Leu Ile Gly Cys Ser Gly Ser Gly Lys Thr Thr
 130                 135                 140

TCT CTT CAT CGT ATT CTA GCC ACG TAT CCT CAG GTG ATT TAC CAT CGT     480
Ser Leu His Arg Ile Leu Ala Thr Tyr Pro Gln Val Ile Tyr His Arg
145                 150                 155                 160

GAA CTC AAT GTA GAG CAG GTG GTG TAT TTG AAA ATA GAC TGC TCG CAT     528
Glu Leu Asn Val Glu Gln Val Val Tyr Leu Lys Ile Asp Cys Ser His
                 165                 170                 175

AAT GGT TCG CTA AAA GAA ATC TGC TTG AAT TTT TTC AGA GCG TTG GAT     576
Asn Gly Ser Leu Lys Glu Ile Cys Leu Asn Phe Phe Arg Ala Leu Asp
             180                 185                 190

CGA GCC TTG GGC TCG AAC TAT GAG CGT CGT TAT GGC TTA AAA CGT CAT     624
Arg Ala Leu Gly Ser Asn Tyr Glu Arg Arg Tyr Gly Leu Lys Arg His
         195                 200                 205

GGT ATA GAA ACC ATG TTG GCT TTG ATG TCG CAA ATA GCC AAT GCA CAT     672
Gly Ile Glu Thr Met Leu Ala Leu Met Ser Gln Ile Ala Asn Ala His
 210                 215                 220
```

```
GCT TTA GGG TTG TTG GTT ATT GAT GAA ATT CAG CAT TTA AGC CGC TCT       720
Ala Leu Gly Leu Leu Val Ile Asp Glu Ile Gln His Leu Ser Arg Ser
225             230                 235                 240

CGT TCG GGT GGA TCT CAA GAG ATG CTG AAC TTT TTT GTG ACG ATG GTG       768
Arg Ser Gly Gly Ser Gln Glu Met Leu Asn Phe Phe Val Thr Met Val
                245                 250                 255

AAT ATT ATT GGC GTA CCA GTG ATG TTG ATT GGT ACC CCT AAA GCA CGA       816
Asn Ile Ile Gly Val Pro Val Met Leu Ile Gly Thr Pro Lys Ala Arg
            260                 265                 270

GAG ATT TTT GAG GCT GAT TTG CGG TCT GCA CGT AGA GGG GCA GGG TTT       864
Glu Ile Phe Glu Ala Asp Leu Arg Ser Ala Arg Arg Gly Ala Gly Phe
        275                 280                 285

GGA GCT ATA TTC TGG GAT CCT ATA CAA CAA ACG CAA CGT GGA AAG CCC       912
Gly Ala Ile Phe Trp Asp Pro Ile Gln Gln Thr Gln Arg Gly Lys Pro
    290                 295                 300

AAT CAA GAG TGG ATC GCT TTT ACG GAT AAT CTT TGG CAA TTA CAG CTT       960
Asn Gln Glu Trp Ile Ala Phe Thr Asp Asn Leu Trp Gln Leu Gln Leu
305                 310                 315                 320

TTA CAA CGC AAA GAT GCG CTG TTA TCG GAT GAG GTC CGT GAT GTG TGG      1008
Leu Gln Arg Lys Asp Ala Leu Leu Ser Asp Glu Val Arg Asp Val Trp
                325                 330                 335

TAT GAG CTA AGC CAA GGA GTG ATG GAC ATT GTA GTA AAA CTT TTT GTA      1056
Tyr Glu Leu Ser Gln Gly Val Met Asp Ile Val Val Lys Leu Phe Val
                340                 345                 350

CTC GCT CAG CTC CGT GCG CTA GCT TTA GGC AAT GAG CGT ATT ACC GCT      1104
Leu Ala Gln Leu Arg Ala Leu Ala Leu Gly Asn Glu Arg Ile Thr Ala
            355                 360                 365

GGT TTA TTG CGG CAA GTG TAT CAA GAT GAG TTA AAG CCT GTG CAC CCC      1152
Gly Leu Leu Arg Gln Val Tyr Gln Asp Glu Leu Lys Pro Val His Pro
        370                 375                 380

ATG CTA GAG GCA TTA CGC TCG GGT ATC CCA GAA CGC ATT GCT CGT TAT      1200
Met Leu Glu Ala Leu Arg Ser Gly Ile Pro Glu Arg Ile Ala Arg Tyr
385                 390                 395                 400

TCT GAT CTA GTC GTT CCC GAG ATT GAT AAA CGG TTA ATC CAA CTT CAG      1248
Ser Asp Leu Val Val Pro Glu Ile Asp Lys Arg Leu Ile Gln Leu Gln
                405                 410                 415

CTA GAT ATC GCA GCG ATA CAA GAA CAA ACA CCA GAA GAA AAA GCC CTT      1296
Leu Asp Ile Ala Ala Ile Gln Glu Gln Thr Pro Glu Glu Lys Ala Leu
                420                 425                 430

CAA GAG TTA GAT ACC GAA GAT CAG CGT CAT TTA TAT CTG ATG CTG AAA      1344
Gln Glu Leu Asp Thr Glu Asp Gln Arg His Leu Tyr Leu Met Leu Lys
            435                 440                 445

GAG GAT TAC GAT TCA AGC CTG TTA ATT CCC ACT ATT AAA AAA GCG TTT      1392
Glu Asp Tyr Asp Ser Ser Leu Leu Ile Pro Thr Ile Lys Lys Ala Phe
        450                 455                 460

AGC CAG AAT CCA ACG ATG ACA AGA CAA AAG TTA CTG CCT CTT GTT TTG      1440
Ser Gln Asn Pro Thr Met Thr Arg Gln Lys Leu Leu Pro Leu Val Leu
465                 470                 475                 480

CAG TGG TTG ATG GAA GGC GAA ACG GTA GTG TCA GAA CTA GAA AAG CCC      1488
Gln Trp Leu Met Glu Gly Glu Thr Val Val Ser Glu Leu Glu Lys Pro
                485                 490                 495

TCC AAG AGT AAA AAG GTT TCG GCT ATA AAG GTA GTC AAG CCC AGC GAC      1536
Ser Lys Ser Lys Lys Val Ser Ala Ile Lys Val Val Lys Pro Ser Asp
                500                 505                 510

TGG GAT AGC TTG CCT GAT ACG GAT TTA CGT TAT ATC TAT TCA CAA CGC      1584
Trp Asp Ser Leu Pro Asp Thr Asp Leu Arg Tyr Ile Tyr Ser Gln Arg
            515                 520                 525

CAA CCT GAA AAA ACC ATG CAT GAA CGG TTA AAA GGG AAA GGG GTA ATA      1632
Gln Pro Glu Lys Thr Met His Glu Arg Leu Lys Gly Lys Gly Val Ile
```

```
        530             535             540
GTG GAT ATG GCG AGC TTA TTT AAA CAA GCA GGT TAG CC                    1670
Val Asp Met Ala Ser Leu Phe Lys Gln Ala Gly  *
545                 550                 555
```

(2) INFORMATION FOR SEQ ID NO:2:

(i) SEQUENCE CHARACTERISTICS:
        (A) LENGTH: 555 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Ala Thr Arg Ile Gln Ala Val Tyr Arg Asp Thr Gly Val Glu
 1               5                  10                  15

Ala Tyr Arg Asp Asn Pro Phe Ile Glu Ala Leu Pro Pro Leu Gln Glu
            20                  25                  30

Ser Val Asn Ser Ala Ala Ser Leu Lys Ser Ser Leu Gln Leu Thr Ser
        35                  40                  45

Ser Asp Leu Gln Lys Ser Arg Val Ile Arg Ala His Thr Ile Cys Arg
    50                  55                  60

Ile Pro Asp Asp Tyr Phe Gln Pro Leu Gly Thr His Leu Leu Leu Ser
65                  70                  75                  80

Glu Arg Ile Ser Val Met Ile Arg Gly Gly Tyr Val Gly Arg Asn Pro
                85                  90                  95

Lys Thr Gly Asp Leu Gln Lys His Leu Gln Asn Gly Tyr Glu Arg Val
            100                 105                 110

Gln Thr Gly Glu Leu Glu Thr Phe Arg Phe Glu Glu Ala Arg Ser Thr
        115                 120                 125

Ala Gln Ser Leu Leu Leu Ile Gly Cys Ser Gly Ser Gly Lys Thr Thr
    130                 135                 140

Ser Leu His Arg Ile Leu Ala Thr Tyr Pro Gln Val Ile Tyr His Arg
145                 150                 155                 160

Glu Leu Asn Val Glu Gln Val Val Tyr Leu Lys Ile Asp Cys Ser His
                165                 170                 175

Asn Gly Ser Leu Lys Glu Ile Cys Leu Asn Phe Phe Arg Ala Leu Asp
            180                 185                 190

Arg Ala Leu Gly Ser Asn Tyr Glu Arg Arg Tyr Gly Leu Lys Arg His
        195                 200                 205

Gly Ile Glu Thr Met Leu Ala Leu Met Ser Gln Ile Ala Asn Ala His
    210                 215                 220

Ala Leu Gly Leu Leu Val Ile Asp Glu Ile Gln His Leu Ser Arg Ser
225                 230                 235                 240

Arg Ser Gly Gly Ser Gln Glu Met Leu Asn Phe Phe Val Thr Met Val
                245                 250                 255

Asn Ile Ile Gly Val Pro Val Met Leu Ile Gly Thr Pro Lys Ala Arg
            260                 265                 270

Glu Ile Phe Glu Ala Asp Leu Arg Ser Ala Arg Arg Gly Ala Gly Phe
        275                 280                 285

Gly Ala Ile Phe Trp Asp Pro Ile Gln Gln Thr Gln Arg Gly Lys Pro
    290                 295                 300

Asn Gln Glu Trp Ile Ala Phe Thr Asp Asn Leu Trp Gln Leu Gln Leu
305                 310                 315                 320

Leu Gln Arg Lys Asp Ala Leu Leu Ser Asp Glu Val Arg Asp Val Trp
```

```
                    325                 330                 335
Tyr Glu Leu Ser Gln Gly Val Met Asp Ile Val Lys Leu Phe Val
                340                 345                 350

Leu Ala Gln Leu Arg Ala Leu Ala Leu Gly Asn Glu Arg Ile Thr Ala
                355                 360                 365

Gly Leu Leu Arg Gln Val Tyr Gln Asp Glu Leu Lys Pro Val His Pro
    370                 375                 380

Met Leu Glu Ala Leu Arg Ser Gly Ile Pro Glu Arg Ile Ala Arg Tyr
385                 390                 395                 400

Ser Asp Leu Val Val Pro Glu Ile Asp Lys Arg Leu Ile Gln Leu Gln
                    405                 410                 415

Leu Asp Ile Ala Ala Ile Gln Glu Gln Thr Pro Glu Glu Lys Ala Leu
                420                 425                 430

Gln Glu Leu Asp Thr Glu Asp Gln Arg His Leu Tyr Leu Met Leu Lys
            435                 440                 445

Glu Asp Tyr Asp Ser Ser Leu Leu Ile Pro Thr Ile Lys Lys Ala Phe
            450                 455                 460

Ser Gln Asn Pro Thr Met Thr Arg Gln Lys Leu Leu Pro Leu Val Leu
465                 470                 475                 480

Gln Trp Leu Met Glu Gly Glu Thr Val Val Ser Glu Leu Glu Lys Pro
                485                 490                 495

Ser Lys Ser Lys Lys Val Ser Ala Ile Lys Val Val Lys Pro Ser Asp
                500                 505                 510

Trp Asp Ser Leu Pro Asp Thr Asp Leu Arg Tyr Ile Tyr Ser Gln Arg
            515                 520                 525

Gln Pro Glu Lys Thr Met His Glu Arg Leu Lys Gly Lys Gly Val Ile
    530                 535                 540

Val Asp Met Ala Ser Leu Phe Lys Gln Ala Gly
545                 550                 555

(2) INFORMATION FOR SEQ ID NO:3:

(i) SEQUENCE CHARACTERISTICS:
        (A) LENGTH: 5926 base pairs
        (B) TYPE: nucleic acid
        (C) STRANDEDNESS: single
        (D) TOPOLOGY: circular (ii) MOLECULE TYPE: other nucleic acid
        (A) DESCRIPTION: /desc = "pEM delta R.adj to 1"

(xi) SEQUENCE DESCRIPTION: SEQ ID NO:3:

TTTAGAGCAA TTCGGTGTTA GTTTCAGCAA GCAAACATTA ACCATAGCTA ATGATTTATA      60

GCCATATTAA CCATTGGGGT ACCGAGCTCG AATTCCATGG TCTGTTTCCT GTGTGAAATT     120

GTTATCCGCT CACAATTCCA CACATTATAC GAGCCGGATG ATTAATTGTC AACAGCTCAT     180

TTCAGAATAT TGCCAGAACC GTTATGATG TCGGCGCAAA AAACATTATC CAGAACGGGA     240

GTGCGCCTTG AGCGACACGA ATTATGCAGT GATTTACGAC CTGCACAGCC ATACCACAGC     300

TTCCGATGGC TGCCTGACGC CAGAAGCATT GGTGCACCGT GCAGTCGATG ATAAGCTGTC     360

AAACCAGATC AATTCGCGCT AACTCACATT AATTGCGTTG CGCTCACTGC CCGCTTTCCA     420

GTCGGGAAAC CTGTCGTGCC AGCTGCATTA ATGAATCGGC CAACGCGCGG GGAGAGGCGG     480

TTTGCGTATT GGGCGCCAGG GTGGTTTTTC TTTTCACCAG TGAGACGGGC AACAGCTGAT     540

TGCCCTTCAC CGCCTGGCCC TGAGAGAGTT GCAGCAAGCG GTCCACGCTG GTTTGCCCCA     600

GCAGGCGAAA ATCCTGTTTG ATGGTGGTTG ACGGCGGGAT ATAACATGAG CTGTCTTCGG     660
```

-continued

```
TATCGTCGTA TCCCACTACC GAGATATCCG CACCAACGCG CAGCCCGGAC TCGGTAATGG    720
CGCGCATTGC GCCCAGCGCC ATCTGATCGT TGGCAACCAG CATCGCAGTG GGAACGATGC    780
CCTCATTCAG CATTTGCATG GTTTGTTGAA AACCGGACAT GGCACTCCAG TCGCCTTCCC    840
GTTCCGCTAT CGGCTGAATT TGATTGCGAG TGAGATATTT ATGCCAGCCA GCCAGACGCA    900
GACGCGCCGA GACAGAACTT AATGGGCCCG CTAACAGCGC GATTTGCTGG TGACCCAATG    960
CGACCAGATG CTCCACGCCC AGTCGCGTAC CGTCTTCATG GGAGAAAATA ATACTGTTGA   1020
TGGGTGTCTG GTCAGAGACA TCAAGAAATA ACGCCGGAAC ATTAGTGCAG GCAGCTTCCA   1080
CAGCAATGGC ATCCTGGTCA TCCAGCGGAT AGTTAATGAT CAGCCCACTG ACGCGTTGCG   1140
CGAGAAGATT GTGCACCGCC GCTTTACAGG CTTCGACGCC GCTTCGTTCT ACCATCGACA   1200
CCACCACGCT GGCACCCAGT TGATCGGCGC GAGATTTAAT CGCCGCGACA ATTTGCGACG   1260
GCGCGTGCAG GGCCAGACTG GAGGTGGCAA CGCCAATCAG CAACGACTGT TTGCCCGCCA   1320
GTTGTTGTGC CACGCGGTTG GGAATGTAAT TCAGCTCCGC CATCGCCGCT TCCACTTTTT   1380
CCCGCGTTTT CGCAGAAACG TGGCTGGCCT GGTTCACCAC GCGGGAAACG GTCTGATAAG   1440
AGACACCGGC ATACTCTGCG ACATCGTATA ACGTTACTGG TTTCACATTC ACCACCCTGA   1500
ATTGACTCTC TTCCGGGCGC TATCATGCCA TACCGCGAAA GGTTTTGCAC CATTCGATGG   1560
TGTCAACGTA AATGCATGCC GCTTCGCCTT CGCGCGCGAA TTGATCTGCT GCCTCGCGCG   1620
TTTCGGTGAT GACGGTGAAA ACCTCTGACA CATGCAGCTC CCGGAGACGG TCACAGCTTG   1680
TCTGTAAGCG GATGCCGGGA GCAGACAAGC CCGTCAGGGC GCGTCAGCGG GTGTTGGCGG   1740
GTGTCGGGGC GCAGCCATGA CCCAGTCACG TAGCGATAGC GGAGTGTATA CTGGCTTAAC   1800
TATGCGGCAT CAGAGCAGAT TGTACTGAGA GTGCACCATA TGCGGTGTGA AATACCGCAC   1860
AGATGCGTAA GGAGAAAATA CCGCATCAGG CGCTCTTCCG CTTCCTCGCT CACTGACTCG   1920
CTGCGCTCGG TCGTTCGGCT GCGGCGAGCG GTATCAGCTC ACTCAAAGGC GGTAATACGG   1980
TTATCCACAG AATCAGGGGA TAACGCAGGA AAGAACATGT GAGCAAAAGG CCAGCAAAAG   2040
GCCAGGAACC GTAAAAAGGC CGCGTTGCTG GCGTTTTTCC ATAGGCTCCG CCCCCCTGAC   2100
GAGCATCACA AAAATCGACG CTCAAGTCAG AGGTGGCGAA ACCCGACAGG ACTATAAAGA   2160
TACCAGGCGT TTCCCCCTGG AAGCTCCCTC GTGCGCTCTC CTGTTCCGAC CCTGCCGCTT   2220
ACCGGATACC TGTCCGCCTT TCTCCCTTCG GGAAGCGTGG CGCTTTCTCA TAGCTCACGC   2280
TGTAGGTATC TCAGTTCGGT GTAGGTCGTT CGCTCCAAGC TGGGCTGTGT GCACGAACCC   2340
CCCGTTCAGC CCGACCGCTG CGCCTTATCC GGTAACTATC GTCTTGAGTC CAACCCGGTA   2400
AGACACGACT TATCGCCACT GGCAGCAGCC ACTGGTAACA GGATTAGCAG AGCGAGGTAT   2460
GTAGGCGGTG CTACAGAGTT CTTGAAGTGG TGGCCTAACT ACGGCTACAC TAGAAGGACA   2520
GTATTTGGTA TCTGCGCTCT GCTGAAGCCA GTTACCTTCG GAAAAAGAGT TGGTAGCTCT   2580
TGATCCGGCA AACAAACCAC CGCTGGTAGC GGTGGTTTTT TTGTTTGCAA GCAGCAGATT   2640
ACGCGCAGAA AAAAAGGATC TCAAGAAGAT CCTTTGATCT TTTCTACGGG GTCTGACGCT   2700
CAGTGGAACG AAAACTCACG TTAAGGGATT TTGGTCATGA GATTATCAAA AAGGATCTTC   2760
ACCTAGATCC TTTTAAATTA AAAATGAAGT TTTAAATCAA TCTAAAGTAT ATATGAGTAA   2820
ACTTGGTCTG ACAGTTACCA ATGCTTAATC AGTGAGGCAC CTATCTCAGC GATCTGTCTA   2880
TTTCGTTCAT CCATAGTTGC CTGACTCCCC GTCGTGTAGA TAACTACGAT ACGGGAGGGC   2940
TTACCATCTG GCCCCAGTGC TGCAATGATA CCGCGAGACC CACGCTCACC GGCTCCAGAT   3000
```

```
TTATCAGCAA TAAACCAGCC AGCCGGAAGG GCCGAGCGCA GAAGTGGTCC TGCAACTTTA    3060
TCCGCCTCCA TCCAGTCTAT TAATTGTTGC CGGGAAGCTA GAGTAAGTAG TTCGCCAGTT    3120
AATAGTTTGC GCAACGTTGT TGCCATTGCT GTAGGCATCG TGGTGTCACG CTCGTCGTTT    3180
GGTATGGCTT CATTCAGCTC CGGTTCCCAA CGATCAAGGC GAGTTACATG ATCCCCCATG    3240
TTGTGCAAAA AAGCGGTTAG CTCCTTCGGT CCTCCGATCG TTGTCAGAAG TAAGTTGGCC    3300
GCAGTGTTAT CACTCATGGT TATGGCAGCA CTGCATAATT CTCTTACTGT CATGCCATCC    3360
GTAAGATGCT TTTCTGTGAC TGGTGAGTAC TCAACCAAGT CATTCTGAGA ATAGTGTATG    3420
CGGCGACCGA GTTGCTCTTG CCCGGCGTCA ACACGGGATA ATACCGCGCC ACATAGCAGA    3480
ACTTTAAAAG TGCTCATCAT TGGAAAACGT TCTTCGGGGC GAAAACTCTC AAGGATCTTA    3540
CCGCTGTTGA GATCCAGTTC GATGTAACCC ACTCGTGCAC CCAACTGATC TTCAGCATCT    3600
TTTACTTTCA CCAGCGTTTC TGGGTGAGCA AAAACAGGAA GGCAAAATGC CGCAAAAAAG    3660
GGAATAAGGG CGACACGGAA ATGTTGAATA CTCATACTCT TCCTTTTTCA ATATTATTGA    3720
AGCATTTATC AGGGTTATTG TCTCATGAGC GGATACATAT TTGAATGTAT TTAGAAAAAT    3780
AAACAAAAAG AGTTTGTAGA AACGCAAAAA GGCCATCCGT CAGGATGGCC TTCTGCTTAA    3840
TTTGATGCCT GGCAGTTTAT GGCGGGCGTC CTGCCCGCCA CCCTCCGGGC CGTTGCTTCG    3900
CAACGTTCAA ATCCGCTCCC GGCGGATTTG TCCTACTCAG GAGAGCGTTC ACCGACAAAC    3960
AACAGATAAA ACGAAAGGCC CAGTCTTTCG ACTGAGCCTT TCGTTTTATT TGATGCCTGG    4020
CAGTTCCCTA CTCTCGCATG GGGAGACCCC ACACTACCAT CGGCGCTACG GCGTTTCACT    4080
TCTGAGTTCG GCATGGGGTC AGGTGGGACC ACCGCGCTAC TGCCGCCAGG CAAATTCTGT    4140
TTTATCAGAC CGCTTCTGCG TTCTGATTTA ATCTGTATCA GGCTGAAAAT CTTCTCTCAT    4200
CCGCCAAAAC AGCCAAGCTT GCATGCCTGC AGGTCGACTC TAGAGGATCC CCAAGAAAGT    4260
CCGTCGGACA GCTTTAATAA ACCCTGCACT TATCTGTTTA GTGTGGGCGG ACAAAATAGT    4320
TGGGAACTGG GAGGGGTGGA AATGGAGTTT TTAAGGATTA TTTAGGGAAG AGTGACAAAA    4380
TAGATGGGAA CTGGGTGTAG CGTCGTAAGC TAATACGAAA ATTAAAAATG ACAAAATAGT    4440
TTGGAACTAG ATTTCACTTA TCTGGTTGGT CGACCTGCAG GGGGGGGGGG GAAAGCCACG    4500
TTGTGTCTCA AAATCTCTGA TGTTACATTG CACAAGATAA AAATATATCA TCATGAACAA    4560
TAAAACTGTC TGCTTACATA AACAGTAATA CAAGGGGTGT TATGAGCCAT ATTCAACGGG    4620
AAACGTCTTG CTCGAGGCCG CGATTAAATT CCAACATGGA TGCTGATTTA TATGGGTATA    4680
AATGGGCTCG CGATAATGTC GGGCAATCAG GTGCGACAAT CTATCGATTG TATGGGAAGC    4740
CCGATGCGCC AGAGTTGTTT CTGAAACATG GCAAAGGTAG CGTTGCCAAT GATGTTACAG    4800
ATGAGATGGT CAGACTAAAC TGGCTGACGG AATTTATGCC TCTTCCGACC ATCAAGCATT    4860
TTATCCGTAC TCCTGATGAT GCATGGTTAC TCACCACTGC GATCCCCGGG AAAACAGCAT    4920
TCCAGGTATT AGAAGAATAT CCTGATTCAG GTGAAAATAT TGTTGATGCG CTGGCAGTGT    4980
TCCTGCGCCG GTTGCATTCG ATTCCTGTTT GTAATTGTCC TTTTAACAGC GATCGCGTAT    5040
TTCGTCTCGC TCAGGCGCAA TCACGAATGA ATAACGGTTT GGTTGATGCG AGTGATTTTG    5100
ATGACGAGCG TAATGGCTGG CCTGTTGAAC AAGTCTGGAA AGAAATGCAT AAGCTTTTGC    5160
CATTCTCACC GGATTCAGTC GTCACTCATG GTGATTTCTC ACTTGATAAC CTTATTTTTG    5220
ACGAGGGGAA ATTAATAGGT TGTATTGATG TTGGACGAGT CGGAATCGCA GACCGATACC    5280
AGGATCTTGC CATCCTATGG AACTGCCTCG GTGAGTTTTC TCCTTCATTA CAGAAACGGC    5340
TTTTTCAAAA ATATGGTATT GATAATCCTG ATATGAATAA ATTGCAGTTT CATTTGATGC    5400
```

-continued

```
TCGATGAGTT TTTCTAATCA GAATTGGTTA ATTGGTTGTA ACACTGGCAG AGCATTACGC      5460

TGACTTGACG GGACGGCGGC TTTGTTGAAT AAATCGAACT TTTGCTGAGT TGAAGGATCA      5520

GATCACGCAT CTTCCCGACA ACGCAGACCG TTCCGTGGCA AAGCAAAAGT TCAAAATCAC      5580

CAACTGGTCC ACCTACAACA AAGCTCTCAT CAACCGTGGC TCCCTCACTT TCTGGCTGGA      5640

TGATGGGGCG ATTCAGGCCT GGTATGAGTC AGCAACACCT TCTTCACGAG GCAGACCTCA      5700

GCGCCCCCCC CCCCCTGCAG GTCGACCCCA CGCCCCTCTT TAATACGACG GGCAATTTGC      5760

ACTTCAGAAA ATGAAGAGTT TGCTTTAGCC ATAACAAAAG TCCAGTATGC TTTTTCACAG      5820

CATAACTGGA CTGATTTCAG TTTACAACTA TTCTGTCTAG TTTAAGACTT TATTGTCATA      5880

GTTTAGATCT ATTTTGTTCA GTTTAAGACT TTATTGTCCG CCCACA                    5926
```

(2) INFORMATION FOR SEQ ID NO:4:

(i) SEQUENCE CHARACTERISTICS:
        (A) LENGTH: 5926 base pairs
        (B) TYPE: nucleic acid
        (C) STRANDEDNESS: single
        (D) TOPOLOGY: circular (ii) MOLECULE TYPE: other nucleic acid
        (A) DESCRIPTION: /desc = "pEM-delta"

(xi) SEQUENCE DESCRIPTION: SEQ ID NO:4:

```
CAGATCAATT CGCGCTAACT CACATTAATT GCGTTGCGCT CACTGCCCGC TTTCCAGTCG       60

GGAAACCTGT CGTGCCAGCT GCATTAATGA ATCGGCCAAC GCGCGGGGAG AGGCGGTTTG      120

CGTATTGGGC GCCAGGGTGG TTTTTCTTTT CACCAGTGAG ACGGGCAACA GCTGATTGCC      180

CTTCACCGCC TGGCCCTGAG AGAGTTGCAG CAAGCGGTCC ACGCTGGTTT GCCCCAGCAG      240

GCGAAAATCC TGTTTGATGG TGGTTGACGG CGGGATATAA CATGAGCTGT CTTCGGTATC      300

GTCGTATCCC ACTACCGAGA TATCCGCACC AACGCGCAGC CCGGACTCGG TAATGGCGCG     360

CATTGCGCCC AGCGCCATCT GATCGTTGGC AACCAGCATC GCAGTGGGAA CGATGCCCTC      420

ATTCAGCATT TGCATGGTTT GTTGAAAACC GGACATGGCA CTCCAGTCGC CTTCCCGTTC      480

CGCTATCGGC TGAATTTGAT TGCGAGTGAG ATATTTATGC CAGCCAGCCA GACGCAGACG      540

CGCCGAGACA GAACTTAATG GGCCCGCTAA CAGCGCGATT TGCTGGTGAC CCAATGCGAC      600

CAGATGCTCC ACGCCCAGTC GCGTACCGTC TTCATGGGAG AAAATAATAC TGTTGATGGG      660

TGTCTGGTCA GAGACATCAA GAAATAACGC CGGAACATTA GTGCAGGCAG CTTCCACAGC      720

AATGGCATCC TGGTCATCCA GCGGATAGTT AATGATCAGC CCACTGACGC GTTGCGCGAG      780

AAGATTGTGC ACCGCCGCTT TACAGGCTTC GACGCCGCTT CGTTCTACCA TCGACACCAC      840

CACGCTGGCA CCCAGTTGAT CGGCGCGAGA TTTAATCGCC GCGACAATTT GCGACGGCGC      900

GTGCAGGGCC AGACTGGAGG TGGCAACGCC AATCAGCAAC GACTGTTTGC CCGCCAGTTG      960

TTGTGCCACG CGGTTGGGAA TGTAATTCAG CTCCGCCATC GCCGCTTCCA CTTTTTCCCG     1020

CGTTTTCGCA GAAACGTGGC TGGCCTGGTT CACCACGCGG GAAACGGTCT GATAAGAGAC     1080

ACCGGCATAC TCTGCGACAT CGTATAACGT TACTGGTTTC ACATTCACCA CCCTGAATTG     1140

ACTCTCTTCC GGGCGCTATC ATGCCATACC GCGAAAGGTT TTGCACCATT CGATGGTGTC     1200

AACGTAAATG CATGCCGCTT CGCCTTCGCG CGCGAATTGA TCTGCTGCCT CGCGCGTTTC     1260

GGTGATGACG GTGAAAACCT CTGACACATG CAGCTCCCGG AGACGGTCAC AGCTTGTCTG     1320

TAAGCGGATG CCGGGAGCAG ACAAGCCCGT CAGGGCGCGT CAGCGGGTGT TGGCGGGTGT     1380
```

-continued

```
CGGGGCGCAG CCATGACCCA GTCACGTAGC GATAGCGGAG TGTATACTGG CTTAACTATG      1440

CGGCATCAGA GCAGATTGTA CTGAGAGTGC ACCATATGCG GTGTGAAATA CCGCACAGAT      1500

GCGTAAGGAG AAAATACCGC ATCAGGCGCT CTTCCGCTTC CTCGCTCACT GACTCGCTGC      1560

GCTCGGTCGT TCGGCTGCGG CGAGCGGTAT CAGCTCACTC AAAGGCGGTA ATACGGTTAT      1620

CCACAGAATC AGGGGATAAC GCAGGAAAGA ACATGTGAGC AAAAGGCCAG CAAAAGGCCA      1680

GGAACCGTAA AAAGGCCGCG TTGCTGGCGT TTTTCCATAG GCTCCGCCCC CCTGACGAGC      1740

ATCACAAAAA TCGACGCTCA AGTCAGAGGT GGCGAAACCC GACAGGACTA TAAAGATACC      1800

AGGCGTTTCC CCCTGGAAGC TCCCTCGTGC GCTCTCCTGT TCCGACCCTG CCGCTTACCG      1860

GATACCTGTC CGCCTTTCTC CCTTCGGGAA GCGTGGCGCT TTCTCATAGC TCACGCTGTA      1920

GGTATCTCAG TTCGGTGTAG GTCGTTCGCT CCAAGCTGGG CTGTGTGCAC GAACCCCCCG      1980

TTCAGCCCGA CCGCTGCGCC TTATCCGGTA ACTATCGTCT TGAGTCCAAC CCGGTAAGAC      2040

ACGACTTATC GCCACTGGCA GCAGCCACTG GTAACAGGAT TAGCAGAGCG AGGTATGTAG      2100

GCGGTGCTAC AGAGTTCTTG AAGTGGTGGC CTAACTACGG CTACACTAGA AGGACAGTAT      2160

TTGGTATCTG CGCTCTGCTG AAGCCAGTTA CCTTCGGAAA AAGAGTTGGT AGCTCTTGAT      2220

CCGGCAAACA AACCACCGCT GGTAGCGGTG GTTTTTTTGT TTGCAAGCAG CAGATTACGC      2280

GCAGAAAAAA AGGATCTCAA GAAGATCCTT TGATCTTTTC TACGGGTCT GACGCTCAGT      2340

GGAACGAAAA CTCACGTTAA GGGATTTTGG TCATGAGATT ATCAAAAAGG ATCTTCACCT      2400

AGATCCTTTT AAATTAAAAA TGAAGTTTTA AATCAATCTA AAGTATATAT GAGTAAACTT      2460

GGTCTGACAG TTACCAATGC TTAATCAGTG AGGCACCTAT CTCAGCGATC TGTCTATTTC      2520

GTTCATCCAT AGTTGCCTGA CTCCCCGTCG TGTAGATAAC TACGATACGG GAGGGCTTAC      2580

CATCTGGCCC CAGTGCTGCA ATGATACCGC GAGACCCACG CTCACCGGCT CCAGATTTAT      2640

CAGCAATAAA CCAGCCAGCC GGAAGGGCCG AGCGCAGAAG TGGTCCTGCA ACTTTATCCG      2700

CCTCCATCCA GTCTATTAAT TGTTGCCGGG AAGCTAGAGT AAGTAGTTCG CCAGTTAATA      2760

GTTTGCGCAA CGTTGTTGCC ATTGCTGTAG GCATCGTGGT GTCACGCTCG TCGTTTGGTA      2820

TGGCTTCATT CAGCTCCGGT TCCCAACGAT CAAGGCGAGT TACATGATCC CCCATGTTGT      2880

GCAAAAAAGC GGTTAGCTCC TTCGGTCCTC CGATCGTTGT CAGAAGTAAG TTGGCCGCAG      2940

TGTTATCACT CATGGTTATG GCAGCACTGC ATAATTCTCT TACTGTCATG CCATCCGTAA      3000

GATGCTTTTC TGTGACTGGT GAGTACTCAA CCAAGTCATT CTGAGAATAG TGTATGCGGC      3060

GACCGAGTTG CTCTTGCCCG GCGTCAACAC GGGATAATAC CGCGCCACAT AGCAGAACTT      3120

TAAAAGTGCT CATCATTGGA AAACGTTCTT CGGGGCGAAA ACTCTCAAGG ATCTTACCGC      3180

TGTTGAGATC CAGTTCGATG TAACCCACTC GTGCACCCAA CTGATCTTCA GCATCTTTTA      3240

CTTTCACCAG CGTTTCTGGG TGAGCAAAAA CAGGAAGGCA AAATGCCGCA AAAAAGGGAA      3300

TAAGGGCGAC ACGGAAATGT TGAATACTCA TACTCTTCCT TTTTCAATAT TATTGAAGCA      3360

TTTATCAGGG TTATTGTCTC ATGAGCGGAT ACATATTTGA ATGTATTTAG AAAAATAAAC      3420

AAAAAGAGTT TGTAGAAACG CAAAAAGGCC ATCCGTCAGG ATGGCCTTCT GCTTAATTTG      3480

ATGCCTGGCA GTTTATGGCG GGCGTCCTGC CCGCCACCCT CCGGGCCGTT GCTTCGCAAC      3540

GTTCAAATCC GCTCCCGGCG GATTTGTCCT ACTCAGGAGA GCGTTCACCG ACAAACAACA      3600

GATAAAACGA AAGGCCCAGT CTTTCGACTG AGCCTTTCGT TTTATTTGAT GCCTGGCAGT      3660

TCCCTACTCT CGCATGGGGA GACCCACAC TACCATCGGC GCTACGGCGT TCACTTCTG      3720

AGTTCGGCAT GGGGTCAGGT GGGACCACCG CGCTACTGCC GCCAGGCAAA TTCTGTTTTA      3780
```

```
TCAGACCGCT TCTGCGTTCT GATTTAATCT GTATCAGGCT GAAAATCTTC TCTCATCCGC    3840

CAAAACAGCC AAGCTTGCAT GCCTGCAGGT CGACTCTAGA GGATCCCCAA GAAAGTCCGT    3900

CGGACAGCTT TAATAAACCC TGCACTTATC TGTTTAGTGT GGGCGGACAA AATAGTTGGG    3960

AACTGGGAGG GGTGGAAATG GAGTTTTTAA GGATTATTTA GGAAGAGTG ACAAAATAGA     4020

TGGGAACTGG GTGTAGCGTC GTAAGCTAAT ACGAAAATTA AAAATGACAA AATAGTTTGG    4080

AACTAGATTT CACTTATCTG GTTGGTCGAC CTGCAGGGGG GGGGGGGAAA GCCACGTTGT    4140

GTCTCAAAAT CTCTGATGTT ACATTGCACA AGATAAAAAT ATATCATCAT GAACAATAAA    4200

ACTGTCTGCT TACATAAACA GTAATACAAG GGGTGTTATG AGCCATATTC AACGGGAAAC    4260

GTCTTGCTCG AGGCCGCGAT TAAATTCCAA CATGGATGCT GATTTATATG GGTATAAATG    4320

GGCTCGCGAT AATGTCGGGC AATCAGGTGC GACAATCTAT CGATTGTATG GGAAGCCCGA    4380

TGCGCCAGAG TTGTTTCTGA AACATGGCAA AGGTAGCGTT GCCAATGATG TTACAGATGA    4440

GATGGTCAGA CTAAACTGGC TGACGGAATT TATGCCTCTT CCGACCATCA AGCATTTTAT    4500

CCGTACTCCT GATGATGCAT GGTTACTCAC CACTGCGATC CCCGGGAAAA CAGCATTCCA    4560

GGTATTAGAA GAATATCCTG ATTCAGGTGA AAATATTGTT GATGCGCTGG CAGTGTTCCT    4620

GCGCCGGTTG CATTCGATTC CTGTTTGTAA TTGTCCTTTT AACAGCGATC GCGTATTTCG    4680

TCTCGCTCAG GCGCAATCAC GAATGAATAA CGGTTTGGTT GATGCGAGTG ATTTTGATGA    4740

CGAGCGTAAT GGCTGGCCTG TTGAACAAGT CTGGAAAGAA ATGCATAAGC TTTTGCCATT    4800

CTCACCGGAT TCAGTCGTCA CTCATGGTGA TTTCTCACTT GATAACCTTA TTTTTGACGA    4860

GGGGAAATTA ATAGGTTGTA TTGATGTTGG ACGAGTCGGA ATCGCAGACC GATACCAGGA    4920

TCTTGCCATC CTATGGAACT GCCTCGGTGA GTTTTCTCCT TCATTACAGA AACGGCTTTT    4980

TCAAAAATAT GGTATTGATA ATCCTGATAT GAATAAATTG CAGTTTCATT TGATGCTCGA    5040

TGAGTTTTTC TAATCAGAAT TGGTTAATTG GTTGTAACAC TGGCAGAGCA TTACGCTGAC    5100

TTGACGGGAC GGCGGCTTTG TTGAATAAAT CGAACTTTTG CTGAGTTGAA GGATCAGATC    5160

ACGCATCTTC CCGACAACGC AGACCGTTCC GTGGCAAAGC AAAAGTTCAA AATCACCAAC    5220

TGGTCCACCT ACAACAAAGC TCTCATCAAC CGTGGCTCCC TCACTTTCTG GCTGGATGAT    5280

GGGGCGATTC AGGCCTGGTA TGAGTCAGCA ACACCTTCTT CACGAGGCAG ACCTCAGCGC    5340

CCCCCCCCCC CTGCAGGTCG ACCCCACGCC CCTCTTTAAT ACGACGGGCA ATTTGCACTT    5400

CAGAAAATGA AGAGTTTGCT TTAGCCATAA CAAAAGTCCA GTATGCTTTT TCACAGCATA    5460

ACTGGACTGA TTTCAGTTTA CAACTATTCT GTCTAGTTTA AGACTTTATT GTCATAGTTT    5520

AGATCTATTT TGTTCAGTTT AAGACTTTAT TGTCCGCCCA CATTTAGAGC AATTCGGTGT    5580

TAGTTTCAGC AAGCAAACAT TAACCATAGC TAATGATTTA TAGCCATATT AACCATTGGG    5640

GTACCGAGCT CGAATTCCAT GGTCTGTTTC CTGTGTGAAA TTGTTATCCG CTCACAATTC    5700

CACACATTAT ACGAGCCGGA TGATTAATTG TCAACAGCTC ATTTCAGAAT ATTTGCCAGA    5760

ACCGTTATGA TGTCGGCGCA AAAAACATTA TCCAGAACGG GAGTGCGCCT TGAGCGACAC    5820

GAATTATGCA GTGATTTACG ACCTGCACAG CCATACCACA GCTTCCGATG GCTGCCTGAC    5880

GCCAGAAGCA TTGGTGCACC GTGCAGTCGA TGATAAGCTG TCAAAC                  5926
```

(2) INFORMATION FOR SEQ ID NO:5:

(i) SEQUENCE CHARACTERISTICS:
        (A) LENGTH: 8906 base pairs
        (B) TYPE: nucleic acid (C) STRANDEDNESS: single
(D) TOPOLOGY: circular (ii) MOLECULE TYPE: other nucleic acid
    (A) DESCRIPTION: /desc = "pER183 (target plasmid)"

(xi) SEQUENCE DESCRIPTION: SEQ ID NO:5:

| | | | | | |
|---|---|---|---|---|---|
| GAATTCCGGA | TGAGCATTCA | TCAGGCGGGC | AAGAATGTGA | ATAAAGGCCG | GATAAAACTT | 60 |
| GTGCTTATTT | TTCTTTACGG | TCTTTAAAAA | GGCCGTAATA | TCCAGCTGAA | CGGTCTGGTT | 120 |
| ATAGGTACAT | TGAGCAACTG | ACTGAAATGC | CTCAAAATGT | TCTTTACGAT | GCCATTGGGA | 180 |
| TATATCAACG | GTGGTATATC | CAGTGATTTT | TTTCTCCATT | TTAGCTTCCT | TAGCTCCTGA | 240 |
| AAATCTCGAT | AACTCAAAAA | ATACGCCCGG | TAGTGATCTT | ATTTCATTAT | GGTGAAAGTT | 300 |
| GGAACCTCTT | ACGTGCCGAT | CAACGTCTCA | TTTTCGCCAA | AAGTTGGCCC | AGGGCTTCCC | 360 |
| GGTATCAACA | GGGACACCAG | GATTTATTTA | TTCTGCGAAG | TGATCTTCCG | TCACAGGTAT | 420 |
| TTATTCGGCG | CAAAGTGCGT | CGGGTGATGC | TGCCAACTTA | CTGATTTAGT | GTATGATGGT | 480 |
| GTTTTTGAGG | TGCTCCAGTG | GCTTCTGTTT | CTATCAGCTG | TCCCTCCTGT | TCAGCTACTG | 540 |
| ACGGGGTGGT | GCGTAACGGC | AAAAGCACCG | CCGGACATCA | GCGCTAGCGG | AGTGTATACT | 600 |
| GGCTTACTAT | GTTGGCACTG | ATGAGGGTGT | CAGTGAAGTG | CTTCATGTGG | CAGGAGAAAA | 660 |
| AAGGCTGCAC | CGGTGCGTCA | GCAGAATATG | TGATACAGGA | TATATTCCGC | TTCCTCGCTC | 720 |
| ACTGACTCGC | TACGCTCGGT | CGTTCGACTG | CGGCGAGCGG | AAATGGCTTA | CGAACGGGGC | 780 |
| GGAGATTTCC | TGGAAGATGC | CAGGAAGATA | CTTAACAGGG | AAGTGAGAGG | GCCGCGGCAA | 840 |
| AGCCGTTTTT | CCATAGGCTC | CGCCCCCCTG | ACAAGCATCA | CGAAATCTGA | CGCTCAAATC | 900 |
| AGTGGTGGCG | AAACCCGACA | GGACTATAAA | GATACCAGGC | GTTTCCCCTG | GCGGCTCCCT | 960 |
| CGTGCGCTCT | CCTGTTCCTG | CCTTTCGGTT | TACCGGTGTC | ATTCCGCTGT | TATGGCCGCG | 1020 |
| TTTGTCTCAT | TCCACGCCTG | ACACTCAGTT | CCGGGTAGGC | AGTTCGCTCC | AAGCTGGACT | 1080 |
| GTATGCACGA | ACCCCCCGTT | CAGTCCGACC | GCTGCGCCTT | ATCCGGTAAC | TATCGTCTTG | 1140 |
| AGTCCAACCC | GGAAAGACAT | GCAAAAGCAC | CACTGGCAGC | AGCCACTGGT | AATTGATTTA | 1200 |
| GAGGAGTTAG | TCTTGAAGTC | ATGCGCCGGT | TAAGGCTAAA | CTGAAAGGAC | AAGTTTTGGT | 1260 |
| GACTGCGCTC | CTCCAAGCCA | GTTACCTCGG | TTCAAAGAGT | TGGTAGCTCA | GAGAACCTTC | 1320 |
| GAAAAACCGC | CCTGCAAGGC | GGTTTTTTCG | TTTTCAGAGC | AAGAGATTAC | GCGCAGACCA | 1380 |
| AAACGATCTC | AAGAAGATCA | TCTTATTAAT | CAGATAAAAT | ATTTCTAGAT | TTCAGTGCAA | 1440 |
| TTTATCTCTT | CAAATGTAGC | ACCTGAAGTC | AGCCCCATAC | GATATAAGTT | GTAATTCTCA | 1500 |
| TGTTTGACAG | CTTATCATCG | GATGGATCTG | AAATTGTAAA | CGTTAATATT | TTGTTAAATT | 1560 |
| CGCGTTAAAT | TTTTGTTAAA | TCAGCTCATT | TTTTAACCAA | TAGGCCGAAA | TCGGCAAAAT | 1620 |
| CCCTTATAAA | TCAAAAGAAT | AGACCGAGAT | AGGGTTGAGT | GTTGTTCCAG | TTTGAACAA | 1680 |
| GAGTCCACTA | TTAAAGAACG | TGGACTCCAA | CGTCAAAGGG | CGAAAAACCG | TCTATCAGGG | 1740 |
| CGATGGCCCA | CTACGTGAAC | CATCACCCTA | ATCAAGTTTT | TTGGGGTCGA | GGTGCCGTAA | 1800 |
| AGCACTAAAT | CGGAACCCTA | AAGGGAGCCC | CCGATTTAGA | GCTTGACGGG | GAAAGCCGGC | 1860 |
| GAACGTGGCG | AGAAAGGAAG | GGAAGAAAGC | GAAAGGAGCG | GGCGCTAGGG | CGCTGGCAAG | 1920 |
| TGTAGCGGTC | ACGCTGCGCG | TAACCACCAC | ACCCGCCGCG | CTTAATGCGC | CGCTACAGGG | 1980 |
| CGCGTCAGAT | CCCATCGATA | AGCTTTAATG | CGGTAGTTTA | TCACAGTTAA | ATTGCTAACG | 2040 |
| CAGTCAGGCA | CCGTGTATGA | AATCTAACAA | TGCGCTCATC | GTCATCCTCG | GCACCGTCAC | 2100 |
| CCTGGATGCT | GTAGGCATAG | GCTTGGTTAT | GCCGGTACTG | CCGGGCCTCT | TGCGGGATAT | 2160 |

```
CGTCCATTCC GACAGCATCG CCAGTCACTA TGGCGTGCTG CTAGCGCTAT ATGCGTTGAT    2220

GCAATTTCTA TGCGCACCCG TTCTCGGAGC ACTGTCCGAC CGCTTTGGCC GCCGCCCAGT    2280

CCTGCTCGCT TCGCTACTTG GAGCCACTAT CGACTACGCG ATCATGGCGA CCACACCCGT    2340

CCTGTGGATC CGCTGGCGAA AGGGGGATGT GCTGCAAGGC GATTAAGTTG GGTAACGCCA    2400

GGGTTTTCCC AGTCACGACG TTGTAAAACG ACGGCCAGTG AATTGCGGCC GCCCTGCAAG    2460

GAAGGGAATG TCGCCAACAG CGAAGAGAGT TGGGCAACGG ATGTGCTGGT GGAGGTGATC    2520

GCCTCCTGAT GATGAGCCGC TCCCGATGTG GTGTCGGGAG CGGTATTTTC TATAAAACTT    2580

ACCGCTTATT TGAGATATTC ATCGAAAATG TCGAGTAATT CTTGATGTAT ACACGGCCAT    2640

TCCTGACCTA AATTGACGGT ACACAAGCCA ATATCGAAGC CATTAATTTT ATAACGATGT    2700

TTCACTGCGG TATCTACGTG GGGATATATT AATAACCCCC CTATGTTTTC GCCATTTTCA    2760

GGCTTTAACG ACCATAAGTA ATTCATCAGT TGATAAAGAT TTTGCGAATG AAATTTTTCT    2820

GTTCCCATTC GTCGTGAAAA AATGCTCTTA TAGTATTTGG CGTCAACGAT AAGTATTTTT    2880

TCTGATGAGC GAATGGTGAT GTCAGTTTCC ATTCGAGGTA ACAAATTAAG TGACTGATCC    2940

GATATACTCG ATGCATCCCA TTTTAAATAA GAGCGGGTTG TGTTTGCAGA CGTTAATTCA    3000

CGACGGCAAA ATTCATAAAG AAACTTTTGA TAAAGTAATG ACATCTCTTT TTCGTTTCTT    3060

TCAAAATCAT AGAAACGGTA GTGTCCTTTG TTTTGACCTG GAATAGAATT ATTGACGATG    3120

AATTTGCAGA CACTGATAAC GAATTTATAA TAACGCGTAT TTTTTCCGCC ATTCAGATAG    3180

CTGAAATGCT GCGGAGTTAA ATGAAGAGTG CTAATGCCCG GTAATTTTCT ATAAAGTGAA    3240

CGAGCTTCAT CTCTGATAGT TGAATTTAAC TTTTCATGCT TAATTAATAT GGCTAATGTG    3300

CTTTTTATAA TTCGGTTAGC CAGCGTGTCT TCATTAAGCA TATCAAAAGT ACTGACGGTT    3360

TTCCCATGAT TAAGATGGAA GCCGCGTATT GTTTTAGCAA ACTCTATTCG CCCTTTGATG    3420

CCAGGAATGA TCTCGGTGTT AGGATTGTAA TCAAGCTCAA GCCCTCGGCG TGAAAGCTGT    3480

AAAACCCCTT TATTTAATAC ATACCCCAGG ATATCAAGAA GATTGTTACC GGGTATGGCT    3540

TCAAGGTTTG CCTGCTTAAT TTCCTGTAAA TAACCCCATG CATAGGTAAG CATGTAATAG    3600

ATATTACGGA CAGGTATCAC GGGCTGTTCC ACTATGAGTC CCCTAATAAT TTGTTGGTCC    3660

ATTTCTGTTG TTTATAGGGG TCATCAAAGA AATATTCTTC GAGTAAAGGG GCGATATCCG    3720

TCATCACAAT TTCATTAAGC CATTGCGTAT CCGGAGAGGT GCCATCTTCC AACCCACAGC    3780

AGAAGTAACT ATGCCCAATG CGGAATCCTT TCCCAAGGAT AGTGGCCTCT TTGCTGATTT    3840

CCTGGTTCAA CTCGTTCATT TTTTGGCATA AAGACTCAAC AAATGAAGGT TCTGCTTTTT    3900

TATTCAGTAA AAAATTCCGG AACTGTGGTG TATCAAAACC TGGCTCAATA TCTATGAAAG    3960

AAAATCGTCT GCGTAGGGCA TAGTCAACAA CGGCCAGAGA GCGATCGGCA GTATTCATTA    4020

AACCGATGAT ATAAACATTC TCCGGGACAT AGAATCGTTC TTCATCGTTT TCGGAGTAGG    4080

TTAGGGGAAC AGACCAGTTT TCACCTCGTT TATCATGTTC CATTAACATC ATCACTTCGC    4140

CAAATACTTT ACTGAGATTG GCACGATTGA TTTCATCTAT AATAAAAATA TACTTTTTCT    4200

CTGGCTGCTC TTTAGCTTGC TGACAAAAAT TGTAAAATAT GCCGTCTTTA CGTCGGAAGC    4260

CGACGCCATT CGGACGATAG CCCTGTATAA AATCCTCATA GCTATAAGAT TGATGGAACT    4320

GAACCATATT GACGCGTTGC GGAGCCTTTT CTCCTGTCAG CAAGTAAGCC AGACGGCGTG    4380

CAACAAAGGT TTTTCCAACG CCGGGCGGCC CCTGGAGGAT AATATTTTTT TTGATGGTTA    4440

ATCGTTTGAG TATCGTCTCT ATTGTGGTTT CAGGGATAAA CAAATCATTT AACGCATCTT    4500
```

```
CCAGACAGTA TGATTCAGTT TTTGACATAG GTGGAATAAC ACTCTTGCCA GAATTAAATA      4560

TTAATTTATA GTCGTTGATT ATGTTGTCCA GCATAGAGGC AAATCGGGTG TAATCAATAC      4620

CCTGTGAGAC TTTTTGGGAA CAGGCGTAAT AGGACTGTCC GTATTTTTA GGATATACAC       4680

CCGAAGTTGC CTGAAAATAC TCTGCGATTG TTTTAGGTAT GTCTGAAGAG AACTGCCATT      4740

GGGCATGTGG TTCATTCGTG TCGCTTATAC CATAAGCCAA AACCAACTCA TCAAAATCTT      4800

TATAATAGAG AATAACGGGA TATATACCGT TAGAAGCTTC CTGACCTTCT CCAAGAAATG      4860

CAAACCAGGG AATAGACGTA AAATTACCAT AACCGAAACT CAATTTTACT CGCAGGTTAC      4920

GGTAAGACGT TGGATAATCT TTAGTGGATT GCGAACGTTG TTGCTGTGCT TGCTTAATAA      4980

ATTTTTCAAT CCAGGGTTGA ATAGATTCCA TAAGATATGC CTTCCTCATT GCTAAGCCTC      5040

TATTATCGCT TTCGCAACGT ACTGAAACAA TAGATTTTTA CTGCAAAATC AGACTGGTAA      5100

ATATTTACTG AGGGGAAAG TTTCTATTGA GTCAGTGGAA GGCTCCCGGT GGTTAACCGG       5160

GAGTAAACGC TGTTACGCGA CTTTCTGTTT ACCGGCAATC ACTCCAATAA ACGCCTGCAC      5220

CTGCTTTTGT TTACGCGCCG ACAGTTTGCA CACCTGGCGT AGCGACTGCA TCAGTTCGCT      5280

CTCCTCGGCG GCGGGTGGTT GGGCGGTGAG GACAATACAG CCTTCCATCA CTTTGACATC      5340

TACCGCCGTG CCAGTGGCAA AACCGGCGGC TTCCAGCCAC TGACCTTTCA GGGTGATGGC      5400

GGGAATACGG CTGTAATCCG GGTAGCGACT CGCATAACCG ACGGTGACAT GACGGTTATT      5460

TGCCGGGGAG ACTTCTGCTT CGAACGGTTG TGCAATAGAA TGCGTGTCAG TCATAACTGC      5520

TATTCTCCAG GAATAGTGAT TGTGATTAGC GATGCGGGTG TGTTGGCGCA CATCCGCACC      5580

GCGCTAAATA CCTGTATATA TCATCAGTAA ATATGGGGAA AGTCCAGCTA AAAATAGAAT      5640

AAAATGGGCA ATTTCTGGAA TGATTTAAAT ATATTTATGT GGGTTATGAT TGGCGTGAAA      5700

TAATAAAAAG CGCACCGGAA AGGTGCGCCA GAAAATAATG TTCAGGATTT TTTACGTGAG      5760

GCTTTTTTAC CCCCGCTAGC TGCGCGTTCA GCTTTGATTT TTTCCAGCAA CGCGGCGGCG      5820

CTGTTTTCTC CGCTGATCAA ATCCGGGTTT TCGGCCCGCC ACTGGGCGGT AAGTTCACCA      5880

CGGAACGCTT TGCCAGGAT GGATTGCGTC AGGTTGTTGA CGCGGGCTAA GGCGTTGTTG       5940

ACCTGTTTTT CTATGGTGTC GGCGTAGGCG AAGAGTTGCT CGACGCGGCG AACGATTTCG      6000

GCTTGTTCTT TTACTGGAGG TAATAAAACA ACTTGGGATT TGATATCTTT TCCTGAAATA     6060

CCTTTTTGAC CAGAAGTTGT TTTCACGCAG TTCATCATTG CATTTCGTGC TGAGGGGGAT     6120

GAAAAAATA TTTCGATATA TTCTGGTAAA GCATCTTTGG TTAATCGAGC TCGAATAAGT       6180

TTATCAGGAT ATAGCAAATT TTGATGTTGT AATTTTTTCA ATAACCCACA AACACCAACA     6240

AATTCTAAAC TTCCGTTATA GCGAGTAAAT AAAAGATCTC CATCTTGTAA TTTGTGGCGG     6300

TTTAGTTCAC TTTCTGAACA TTCTAGAGTC GACCTGCAGG CATGCAAGCT TGGCGTAATC     6360

ATGGTCATAG CTGTTTCCTG TGTGAAATTG TTATCCGCTC ACAATTCCAC ACAACATACG     6420

AGCCGGAAGC ATAAAGTGTA AAGCCTGGGG TGCCTAATGA GTGAGCTAAC TCACATTAAT     6480

TGCGTTGCGC TCACTGCCCG CTTTCCAGTC GGGAAACCTG TCGTGCCAGC GGATCCTCTA     6540

CGCCGGACGC ATCGTGGCCG GCATCACCGG CGCCACAGGT GCGGTTGCTG GCGCCTATAT     6600

CGCCGACATC ACCGATGGGG AAGATCGGGC TCGCCACTTC GGGCTCATGA GCGCTTGTTT     6660

CGGCGTGGGT ATGGTGGCAG GCCCCGTGGC CGGGGGACTG TTGGGCGCCA TCTCCTTGCA     6720

TGCACCATTC CTTGCGGCGG CGGTGCTCAA CGGCCTCAAC CTACTACTGG GCTGCTTCCT     6780

AATGCAGGAG TCGCATAAGG GAGAGCGTCG ACCGATGCCC TTGAGAGCCT TCAACCCAGT     6840

CAGCTCCTTC CGGTGGGCGC GGGGCATGAC TATCGTCGCC GCACTTATGA CTGTCTTCTT     6900
```

-continued

```
TATCATGCAA CTCGTAGGAC AGGTGCCGGC AGCGCTCTGG GTCATTTTCG GCGAGGACCG      6960

CTTTCGCTGG AGCGCGACGA TGATCGGCCT GTCGCTTGCG GTATTCGGAA TCTTGCACGC      7020

CCTCGCTCAA GCCTTCGTCA CTGGTCCCGC CACCAAACGT TTCGGCGAGA AGCAGGCCAT      7080

TATCGCCGGC ATGGCGGCCG ACGCGCTGGG CTACGTCTTG CTGGCGTTCG CGACGCGAGG      7140

CTGGATGGCC TTCCCCATTA TGATTCTTCT CGCTTCCGGC GGCATCGGGA TGCCCGCGTT      7200

GCAGGCCATG CTGTCCAGGC AGGTAGATGA CGACCATCAG GGACAGCTTC AAGGATCGCT      7260

CGCGGCTCTT ACCAGCCTAA CTTCGATCAT TGGACCGCTG ATCGTCACGG CGATTTATGC      7320

CGCCTCGGCG AGCACATGGA ACGGGTTGGC ATGGATTGTA GGCGCCGCCC TATACCTTGT      7380

CTGCCTCCCC GCGTTGCGTC GCGGTGCATG GAGCCGGGCC ACCTCGACCT GAATGGAAGC      7440

CGGCGGCACC TCGCTAACGG ATTCACCACT CCAAGAATTG GAGCCAATCA ATTCTTGCGG      7500

AGAACTGTGA ATGCGCAAAC CAACCCTTGG CAGAACATAT CCATCGCGTC CGCCATCTCC      7560

AGCAGCCGCA CGCGGCGCAT CTCGGGCAGC GTTGGGTCCT GGCCACGGGT GCGCATGATC      7620

GTGCTCCTGT CGTTGAGGAC CCGGCTAGGC TGGCGGGGTT GCCTTACTGG TTAGCAGAAT      7680

GAATCACCGA TACGCGAGCG AACGTGAAGC GACTGCTGCT GCAAAACGTC TGCGACCTGA      7740

GCAACAACAT GAATGGTCTT CGGTTTCCGT GTTTCGTAAA GTCTGGAAAC GCGGAAGTCC      7800

CCTACGTGCT GCTGAAGTTG CCCGCAACAG AGAGTGGAAC CAACCGGTGA TACCACGATA      7860

CTATGACTGA GAGTCAACGC CATGAGCGGC CTCATTTCTT ATTCTGAGTT ACAACAGTCC      7920

GCACCGCTGC CGGTAGCTCC TTCCGGTGGG CGCGGGCAT GACTATCGTC GCCGCACTTA      7980

TGACTGTCTT CTTTATCATG CAACTCGTAG GACAGGTGCC GGCAGCGCCC AACAGTCCCC      8040

CGGCCACGGG GCCTGCCACC ATACCCACGC CGAAACAAGC GCCCTGCACC ATTATGTTCC      8100

GGATCTGCAT CGCAGGATGC TGCTGGCTAC CCTGTGGAAC ACCTACATCT GTATTAACGA      8160

AGCGCTAACC GTTTTTATCA GGCTCTGGGA GGCAGAATAA ATGATCATAT CGTCAATTAT      8220

TACCTCCACG GGGAGAGCCT GAGCAAACTG GCCTCAGGCA TTTGAGAAGC ACACGGTCAC      8280

ACTGCTTCCG GTAGTCAATA AACCGGTAAA CCAGCAATAG ACATAAGCGG CTATTTAACG      8340

ACCCTGCCCT GAACCGACGA CCGGGTCGAA TTTGCTTTCG AATTTCTGCC ATTCATCCGC      8400

TTATTATCAC TTATTCAGGC GTAGCAACCA GGCGTTTAAG GGCACCAATA ACTGCCTTAA      8460

AAAAATTACG CCCCGCCCTG CCACTCATCG CAGTACTGTT GTAATTCATT AAGCATTCTG      8520

CCGACATGGA AGCCATCACA GACGGCATGA TGAACCTGAA TCGCCAGCGG CATCAGCACC      8580

TTGTCGCCTT GCGTATAATA TTTGCCCATG GTGAAAACGG GGGCGAAGAA GTTGTCCATA      8640

TTGGCCACGT TTAAATCAAA ACTGGTGAAA CTCACCCAGG GATTGGCTGA GACGAAAAAC      8700

ATATTCTCAA TAAACCCTTT AGGGAAATAG GCCAGGTTTT CACCGTAACA CGCCACATCT      8760

TGCGAATATA TGTGTAGAAA CTGCCGGAAA TCGTCGTGGT ATTCACTCCA GAGCGATGAA      8820

AACGTTTCAG TTTGCTCATG GAAAACGGTG TAACAAGGGT GAACACTATC CCATATCACC      8880

AGCTCACCGT CTTTCATTGC CATACG                                          8906
```

(2) INFORMATION FOR SEQ ID NO:6:

(i) SEQUENCE CHARACTERISTICS:
        (A) LENGTH: 3190 base pairs
        (B) TYPE: nucleic acid
        (C) STRANDEDNESS: single
        (D) TOPOLOGY: circular (ii) MOLECULE TYPE: other nucleic acid (A) DESCRIPTION: /desc = "pRM2 (target plasmid)"

(xi) SEQUENCE DESCRIPTION: SEQ ID NO:6:

| | | | | | |
|---|---|---|---|---|---|
| GCGCCCAATA | CGCAAACCGC | CTCTCCCCGC | GCGTTGGCCG | ATTCATTAAT | GCAGCTGGCA | 60 |
| CGACAGGTTT | CCCGACTGGA | AAGCGGGCAG | TGAGCGCAAC | GCAATTAATG | TGAGTTAGCT | 120 |
| CACTCATTAG | GCACCCCAGG | CTTTACACTT | TATGCTTCCG | GCTCGTATGT | TGTGTGGAAT | 180 |
| TGTGAGCGGA | TAACAATTTC | ACACAGGAAA | CAGCTATGAC | CATGATTACG | AATTCGAGCT | 240 |
| CGGTACCCGG | GGATCCTCTA | GAGTCGAGAT | GCCGCATGTG | GAAGAGGTGA | TTGCACCGAT | 300 |
| CTTCTACACC | GTTCCGCTGC | AGCTGCTGGC | TTACCATGTC | GCGCTGATCA | AAGGCACCGA | 360 |
| CGTTGACCAG | CCGCGTAACC | TGGCAAAATC | GGTTACGGTT | GAGTAATAAA | TGGATGCCCT | 420 |
| GCGTAAGCGG | GGCATTTTTC | TTCCTGTTAT | GTTTTTAATC | AAACATCCTG | CCAACTCCAT | 480 |
| GTGACAAACC | GTCATCTTCG | GCTACTTTTT | CTCTGTCACA | GAATGAAAAT | TTTCTGTCAT | 540 |
| CTCTTCGTTA | TTAATGTTTG | TAATTGACTG | AATATCAACG | CTTATTTAAA | TCAGACTGAA | 600 |
| GACTTATCTC | TCTCTGTCAT | AAAACTGTCA | TATTCCTTAC | ATATAACTGT | CACCTGTTTG | 660 |
| TCCTATTTTG | CTTGTCGTAG | CCAACAAACA | ATGCTTTATG | AATCCTCCCA | GGAGACATTA | 720 |
| TGAAAGTTAT | GCGTACCACC | GTCGCAACTG | TTGTCGCCGC | GACCTTATCG | ACCTGCAGGC | 780 |
| ATGCAAGCTT | GGCACTGGCC | GTCGTTTTAC | AACGTCGTGA | CTGGGAAAAC | CCTGGCGTTA | 840 |
| CCCAACTTAA | TCGCCTTGCA | GCACATCCCC | CTTTCGCCAG | CTGGCGTAAT | AGCGAAGAGG | 900 |
| CCCGCACCGA | TCGCCCTTCC | CAACAGTTGC | GCAGCCTGAA | TGGCGAATGG | CGCCTGATGC | 960 |
| GGTATTTTCT | CCTTACGCAT | CTGTGCGGTA | TTTCACACCG | CATATGGTGC | ACTCTCAGTA | 1020 |
| CAATCTGCTC | TGATGCCGCA | TAGTTAAGCC | AGCCCCGACA | CCCGCCAACA | CCCGCTGACG | 1080 |
| CGCCCTGACG | GGCTTGTCTG | CTCCCGGCAT | CCGCTTACAG | ACAAGCTGTG | ACCGTCTCCG | 1140 |
| GGAGCTGCAT | GTGTCAGAGG | TTTTCACCGT | CATCACCGAA | ACGCGCGAGA | CGAAAGGGCC | 1200 |
| TCGTGATACG | CCTATTTTTA | TAGGTTAATG | TCATGATAAT | AATGGTTTCT | TAGACGTCAG | 1260 |
| GTGGCACTTT | TCGGGGAAAT | GTGCGCGGAA | CCCCTATTTG | TTTATTTTTC | TAAATACATT | 1320 |
| CAAATATGTA | TCCGCTCATG | AGACAATAAC | CCTGATAAAT | GCTTCAATAA | TATTGAAAAA | 1380 |
| GGAAGAGTAT | GAGTATTCAA | CATTTCCGTG | TCGCCCTTAT | TCCCTTTTTT | GCGGCATTTT | 1440 |
| GCCTTCCTGT | TTTTGCTCAC | CCAGAAACGC | TGGTGAAAGT | AAAAGATGCT | GAAGATCAGT | 1500 |
| TGGGTGCACG | AGTGGGTTAC | ATCGAACTGG | ATCTCAACAG | CGGTAAGATC | CTTGAGAGTT | 1560 |
| TTCGCCCCGA | AGAACGTTTT | CCAATGATGA | GCACTTTTAA | AGTTCTGCTA | TGTGGCGCGG | 1620 |
| TATTATCCCG | TATTGACGCC | GGGCAAGAGC | AACTCGGTCG | CCGCATACAC | TATTCTCAGA | 1680 |
| ATGACTTGGT | TGAGTACTCA | CCAGTCACAG | AAAAGCATCT | TACGGATGGC | ATGACAGTAA | 1740 |
| GAGAATTATG | CAGTGCTGCC | ATAACCATGA | GTGATAACAC | TGCGGCCAAC | TTACTTCTGA | 1800 |
| CAACGATCGG | AGGACCGAAG | GAGCTAACCG | CTTTTTTGCA | CAACATGGGG | GATCATGTAA | 1860 |
| CTCGCCTTGA | TCGTTGGGAA | CCGGAGCTGA | ATGAAGCCAT | ACCAAACGAC | GAGCGTGACA | 1920 |
| CCACGATGCC | TGTAGCAATG | GCAACAACGT | TGCGCAAACT | ATTAACTGGC | GAACTACTTA | 1980 |
| CTCTAGCTTC | CCGGCAACAA | TTAATAGACT | GGATGGAGGC | GGATAAAGTT | GCAGGACCAC | 2040 |
| TTCTGCGCTC | GGCCCTTCCG | GCTGGCTGGT | TTATTGCTGA | TAAATCTGGA | GCCGGTGAGC | 2100 |
| GTGGGTCTCG | CGGTATCATT | GCAGCACTGG | GGCCAGATGG | TAAGCCCTCC | CGTATCGTAG | 2160 |
| TTATCTACAC | GACGGGGAGT | CAGGCAACTA | TGGATGAACG | AAATAGACAG | ATCGCTGAGA | 2220 |
| TAGGTGCCTC | ACTGATTAAG | CATTGGTAAC | TGTCAGACCA | AGTTTACTCA | TATATACTTT | 2280 |

```
AGATTGATTT AAAACTTCAT TTTTAATTTA AAAGGATCTA GGTGAAGATC CTTTTTGATA    2340

ATCTCATGAC CAAAATCCCT TAACGTGAGT TTTCGTTCCA CTGAGCGTCA GACCCCGTAG    2400

AAAAGATCAA AGGATCTTCT TGAGATCCTT TTTTTCTGCG CGTAATCTGC TGCTTGCAAA    2460

CAAAAAAACC ACCGCTACCA GCGGTGGTTT GTTTGCCGGA TCAAGAGCTA CCAACTCTTT    2520

TTCCGAAGGT AACTGGCTTC AGCAGAGCGC AGATACCAAA TACTGTCCTT CTAGTGTAGC    2580

CGTAGTTAGG CCACCACTTC AAGAACTCTG TAGCACCGCC TACATACCTC GCTCTGCTAA    2640

TCCTGTTACC AGTGGCTGCT GCCAGTGGCG ATAAGTCGTG TCTTACCGGG TTGGACTCAA    2700

GACGATAGTT ACCGGATAAG GCGCAGCGGT CGGGCTGAAC GGGGGGTTCG TGCACACAGC    2760

CCAGCTTGGA GCGAACGACC TACACCGAAC TGAGATACCT ACAGCGTGAG CTATGAGAAA    2820

GCGCCACGCT TCCCGAAGGG AGAAAGGCGG ACAGGTATCC GGTAAGCGGC AGGGTCGGAA    2880

CAGGAGAGCG CACGAGGGAG CTTCCAGGGG GAAACGCCTG GTATCTTTAT AGTCCTGTCG    2940

GGTTTCGCCA CCTCTGACTT GAGCGTCGAT TTTTGTGATG CTCGTCAGGG GGGCGGAGCC    3000

TATGGAAAAA CGCCAGCAAC GCGGCCTTTT TACGGTTCCT GGCCTTTTGC TGGCCTTTTG    3060

CTCACATGTT CTTTCCTGCG TTATCCCCTG ATTCTGTGGA TAACCGTATT ACCGCCTTTG    3120

AGTGAGCTGA TACCGCTCGC CGCAGCCGAA CGACCGAGCG CAGCGAGTCA GTGAGCGAGG    3180

AAGCGGAAGA                                                         3190

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC95)
            used to analyze products of transposition."

(xi) SEQUENCE DESCRIPTION: SEQ ID NO:7:

ATAATCCTTA AAAACTCCAT TTCCACCCCT                                     30

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC209)
            used to analyze products of transposition"

(xi) SEQUENCE DESCRIPTION: SEQ ID NO:8:

GTGATTGCAC CGATCTTCTA CACCGTTCC                                      29

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC429)
            used to analyze products of transposition"
```

(xi) SEQUENCE DESCRIPTION: SEQ ID NO:9:

TTTCACCGTC ATCACCGAAA CGCGCGAGAC                                   30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC430)
            used to analyze products of transposition"

(xi) SEQUENCE DESCRIPTION: SEQ ID NO:10:

AATGACTTGG TTGAGTACTC ACCAGTCACA                                   30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC431)
            used to analyze the products of transpostion"

(xi) SEQUENCE DESCRIPTION: SEQ ID NO:11:

ATGAACGAAA TAGACAGATC GCTGAGATAG                                   30

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC432)
            used to analyze products of transposition"

(xi) SEQUENCE DESCRIPTION: SEQ ID NO:12:

CAAGACGATA GTTACCGGAT AAGGCGCAGC                                   30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide (NLC94)
            used for sequence determination"

(xi) SEQUENCE DESCRIPTION: SEQ ID NO:13:

AAAGTCCAGT ATGCTTTTTC ACAGCATAAC                                   30

(2) INFORMATION FOR SEQ ID NO:14:

(i) SEQUENCE CHARACTERISTICS:
        (A) LENGTH: 5 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:14:

Asn Tyr Asn Arg Asn
1               5

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Asn Tyr Thr Arg Asn
1               5
```

GAIN OF FUNCTION MUTATIONS IN ATP-DEPENDENT TRANSPOSITION PROTEINS

This application is a non-provisional application claiming priority to provisional patent application No. 60/037,955 filed on Feb. 20, 1997.

BACKGROUND OF THE INVENTION

1. Field of the Invention

The invention is specifically directed to efficient, random, simple insertion of a transposon or derivative transposable element into DNA in vivo or in vitro. The invention is particularly directed to mutations in ATP-utilizing regulatory transposition proteins that permit insertion with less target-site specificity than wild-type. The invention encompasses gain-of-function mutations in TnsC, an ATP-utilizing regulatory transposition protein that activates the bacterial transposon Tn7. Such mutations enable the insertion of a Tn7 transposon or derivative transposable element in a non-specific manner into a given DNA segment. Insertion can be effected in plasmid and cosmid libraries, cDNA libraries, PCR products, bacterial artificial chromosomes, yeast artificial chromosomes, mammalian artificial chromosomes, genomic DNAs, and the like. Such insertion is useful in DNA sequencing methods, for genetic analysis by insertional mutagenesis, and alteration of gene expression by insertion of a given genetic sequence.

2. Description of the Background Art

Transposable elements are discrete segments of DNA capable of mobilizing nonhomologously from one genetic location to another, that typically carry sequence information important for two main functions that confer the ability to mobilize. They encode the proteins necessary to carry out the catalytic activity associated with transposition, and contain the cis-acting sequences, located at the transposon termini, that act as substrates for these proteins. The same proteins can participate in the selection of the target site for insertion.

The selection of a new insertion site is usually not a random process; instead, many transposons show characteristic preferences for certain types of target sites. One broad characteristic that differentiates the wide variety of transposable elements known is the nature of the target site selectivity (1). A component of this selectivity can be the target sequence itself. The bacterial transposon Tn10 preferentially selects a relatively highly conserved 9 bp motif as the predominant site for transposon insertion and less often selects other more distantly related sites in vivo (2). The Tc1 and Tc3 mariner elements of *C. elegans* insert preferentially at a TA dinucleotide such that each end of the element is flanked by a TA duplication (3) (4) (5). A lower specificity consensus sequence, N-Y-G/C-R-N has been determined from populations of both in vivo and in vitro insertions for the bacteriophage Mu (7). In contrast to these elements, the bacterial transposon Tn5 exhibits markedly lower insertion site specificity, although some isolated "hotspots" have been detected (8).

Another selection mechanism relies on structural features or presence of cellular protein complexes at the target sites. The yeast transposon Ty3 preferentially inserts into the promoters of genes transcribed by RNA polymerase III, responding to signals from cellular proteins TFIIIB and TFIIIC (9).

Understanding how these factors modulate transposase activity to impose target site preferences will lend insight into the spread of transposons and viruses, and may suggest ways to manipulate those target preferences. The bacterial transposon Tn7 is distinctive in that it uses several element-encoded accessory proteins to evaluate potential target DNAs for positive and negative features, and to select a target site (1). Tn7 encodes five genes whose protein products mediate its transposition (10) (11).

Two of the proteins, TnsA and TnsB, constitute the transposase activity, collaborating to execute the catalytic steps of strand breakage and joining (12). The activity of this transposase is modulated by the remaining proteins, TnsC, TnsD, and TnsE, and also by the nature of the target DNA.

TnsC, TnsD, and TnsE interact with the target DNA to modulate the activity of the transposase via two distinct pathways. TnsABC+TnsD directs transposition to attTn7, a discrete site on the *E. coli* chromosome, at a high frequency, and to other loosely related "pseudo att" sites at low frequency (13). The alternative combination TnsABC+E directs transposition to many unrelated non-attTn7 sites in the chromosome at low frequency (13) (10) (11) and preferentially to conjugating plasmids (14). Thus, attTn7 and conjugable plasmids contain positive signals that recruit the transposon to these target DNAs. The alternative target site selection mechanisms enable Tn7 to inspect a variety of potential target sites in the cell and select those most likely to ensure its survival.

The Tn7 transposition machinery can also recognize and avoid targets that are unfavorable for insertion. Tn7 transposition occurs only once into a given target molecule; repeated transposition events into the same target are specifically inhibited (15) (16). Therefore, a pre-existing copy of Tn7 in a potential target DNA generates a negative signal which renders that target "immune" to further insertion. The negative target signal affects both TnsD- and TnsE-activated transposition reactions and is dominant to any positive signals present on a potential target molecule (16). Several other transposons, such as Mu and members of the Tn3 family, also display this form of negative target regulation (17) (18) (19) (7).

Target selection could be an early or late event in the course of a transposition reaction. For example, a transposon could constitutively excise from its donor position, and the excised transposon could then be captured at different frequencies by different types of target molecules. Tn10 appears to follow this course of events in vitro, excising from its donor position before any interactions with target DNA occur (20) (21). Alternatively, the process of transposon excision could itself be dependent on the identification of a favorable target site. Tn7 transposition shows an early dependence on target DNA signals in vitro: neither transposition intermediates nor insertion products are seen in the absence of an attTn7 target (22). Thus, the nature of the target DNA appears to regulate the initiation of Tn7 transposition in vitro.

An important question is how positive and negative target signals are communicated to the Tn7 transposase. Reconstitution of the TnsABC+TnsD reaction in vitro has provided a useful tool for detailed dissection of Tn7 transposition (22) (23). This reaction has been instrumental in delineating the role of each of the individual proteins play in target site selection. Dissection of the TnsABC+D reaction in vitro has implicated TnsC as a pivotal connector between the TnsAB transposase and the target DNA. TnsC is an ATP-dependent DNA-binding protein with no known sequence specificity (24). However, TnsC can respond to signals from attTn7 via an interaction with the site-specific DNA-binding protein TnsD. In a standard in vitro transposition reaction TnsD is required for transposition to the attTn7 site on a target DNA molecule. This site-specific insertion process is tightly regulated by TnsC, but does not occur in the absence of TnsD. Additional evidence for a TnsC-TnsD interaction comes from DNA protection and band shift analysis with attTn7 DNA (23). Direct interaction between TnsC and the TnsAB transposase has also recently been observed (25) (26).

Therefore, TnsC may serve as a "connector" or "matchmaker" between the transposase and the TnsD+attTn7 target complex (23) (27). This connection is not constitutive, but instead appears to be regulated by the ATP state of TnsC. Only the ATP-bound form of TnsC is competent to interact with target DNAs and activate the TnsA+B transposase; the ADP-bound form of TnsC has neither of these activities and cannot participate in Tn7 transposition (24) (23). TnsC hydrolyzes ATP at a modest rate (25), and therefore can switch from an active to an inactive state. The modulation of the ATP state of TnsC may be a central mechanism for regulating Tn7 transposition.

The possibility that TnsC regulates the connection between the TnsA+B transposase and the target site prompted the inventor to predict that TnsC mutants can be isolated that would constitutively activate Tn7 transposition.

TnsC therefore became an excellent candidate for mutagenesis, to search for a gain of function protein capable of circumventing the requirement for targeting proteins. The inventor therefore identified gain-of-function TnsC mutants which can activate the TnsA+B transposase in the absence of TnsD or TnsE. They have characterized the ability of these mutants to promote insertions into various targets, and to respond to regulatory signals on those targets.

One class of TnsC mutants activates transposition in a way that is still sensitive to target signals, whereas a second class of TnsC mutants activates transposition in a way that appears to bypass target signals. As had been observed in vitro, the critical communication between the transposon and the target DNA appears to be an early event in the Tn 7 reaction pathway in vivo, preceding the double-strand breaks at the transposon ends that initiate transposition.

A particular mutant isolated from the random mutagenesis is $TnsC^{A225V}$, a mutant capable of an impressive activation of Tn7 transposition in the absence of TnsD (25). The single amino acid substitution made to generate $TnsC^{A225V}$ has altered the protein such that it no longer requires an interaction with the target-associated TnsD, enabling it to activate transposition to a variety of target molecules very efficiently (25) (26). The inventor concluded that $TnsC^{A225V}$ could promote transposition to target DNAs with low specificity based on results where transposition driven by the $TnsABC^{A225V}$ machinery was directed to either F plasmids containing an attTn7 site, F plasmids lacking an attTn7 site, or the *E. coli* chromosome with no apparent preference.

DNA Sequencing

Sequencing DNA fragments cloned into vectors requires provision of priming sites at distributed locations within the fragment of interest, if the fragment is larger than the sequence run length (amount of sequence that can be determined from a single sequencing reaction). At present there are three commonly used methods of providing these priming sites:

A) Design of a new primer from sequence determined in a previous run from vector-encoded primer or other previously determined primer (prime and run, primer walking)

B) Random fragmentation and recloning of smaller pieces, followed by determination of the sequence of the smaller pieces from vector-encoded (universal) priming sites, followed by sequence assembly by overlap of sequence (random shotgun sequencing).

C) Deletion of variable amounts of the fragment of interest from an end adjacent to the vector, to bring undetermined fragment sequence close enough to the vector-encoded (universal) primer to allow sequence determination.

All of these methods have disadvantages.

Method A is time-consuming and expensive because of the delay involved in design of new primers and their cost. Moreover, if the fragment contains DNA repeats longer than the sequence run, it may be impossible to design a unique new primer; sequence runs made with primers within the repeat sequence will display two or more sequences that cannot be disentangled.

Method B requires recloning; random fragmentation is difficult to achieve because fragments that are efficiently clonable (restriction enzyme digestion) do not have ends randomly distributed (Adams, M. D., Fields, C. and Ventor, J. C. editors Automated DNA Sequencing and Analysis Academic Press 1994; Chapter 6, Bodenteich, K. et al.), and fragmentation methods that provide randomly distributed ends (shearing, sonication) do not provide DNA ends that are efficiently clonable (with 5' phosphate and 3' OH moieties). Sequence assembly of is also difficult or impossible when two or more repetitive sequences longer than the sequence run are present in the starting fragment.

Method C depends on providing randomly distributed end points for enzymatically determined deletions. There are many methods for making such deletions (especially those involving exonuclease digestions, typically Exonuclease III), none of which provide entirely random endpoints and which depend on the presence of unique suitable restriction enzyme sites at one or both ends of the cloned fragment. However, because the deletion series in principle allows construction of a map (of nested remaining fragment lengths in deletion derivatives) that is independent of the sequence itself, this method can allow repetitive sequence longer than the sequence run to be located within the fragment at appropriate locations.

A method for introduction of universal priming sites at randomly distributed locations within a fragment of interest is therefore a useful advance in sequencing technology.

Transposition and the sequencing problem.

Previous efforts have been made to provide distributed priming sites by means of transposable elements. These methods have fallen short of this goal in three ways: first, the transposable elements have not provided a sufficiently random distribution of priming sites; second, the transposition method (carrying out transposition in vivo, followed by recovery of the targeted DNA and repurification) has been time-consuming and laborious; third, the Systems have been prone to produce undesired products. These undesired products include but are not limited to: a) cointegrates (replicon fusions) between the donor of the transposon and the target plasmid; b) insertions in which the two ends of the transposon act at different positions (leading to deletion of the intervening target); c) insertions of multiple copies of the transposon into the target, so that priming from one end of the transposon yields two superimposed sequences. The method has been laborious in two ways: the majority of insertions have been into chromosomal DNA of the host, and even for those insertions into the plasmid the recovery method has entailed loss of independence of insertions. in vitro methods of insertion have suffered from both the non-random location of insertion sites and the undesired products, and also from poor efficiency, so that it has been impractical to obtain large numbers of insertions into the target of interest without excessive labor.

Increasing interest in large scale sequencing projects and a concomitant search for highly efficient in vitro mutagenesis methods has promoted the adaptation of several in vitro transposon systems as tools to study genomes. An in vivo reaction for the bacterial transposon Tn3 has been used to efficiently sequence plasmid inserts of variable lengths; however, only approximately 37% of the nucleotides were found to be capable of serving as sites for insertion (Davies, 1995 #419). A similar, more random system has been developed for yeast retrotransposon Ty1, employing synthetic transposons with U3 ends as substrates and Ty1 virus-like particles supplying transposition functions (28) to sequence plasmids with yeast and human DNA inserts. A disadvantage to this method is the requirement for the cumbersome preparation of VLPs. In vitro transposition with an MLV integrase system has been utilized as a tool to dissect some of the mysteries of chromatin packaging (29) (30) (31) and as a tool for functional genetic footprinting (32). However, the MLV insertions do not appear to be completely random. An object of the invention therefore is to provide a transposon and transposition reaction with more random target site specificity. Therefore, the inventor examined the target site selectivity of the $TnsC^{A225V}$ machinery in vitro and explored the viability of this reaction as an effective tool for random insertional mutagenesis.

SUMMARY OF THE INVENTION

Accordingly, a general object of the invention is to provide a transposable system that achieves efficient, simple, non-specific or random insertion into any given DNA segment.

A further object of the invention is to provide a transposable system that achieves efficient random insertional mutagenesis via simple insertion.

Therefore, a specific object of the invention is to provide a transposable system that achieves efficient target site specificity that is reduced from wild-type and preferably random, via simple insertion.

A more particular object of the invention is to provide a transposon containing a mutation in a transposon-derived protein that allows efficient, simple insertion and target site selectivity that is reduced from the wild-type, and preferably random.

A more particular object of the invention is to provide a transposable system with a mutation in a transposon-derived ATP-utilizing regulatory protein. The mutation allows the efficient, simple, non-specific or random insertion of the transposable element into a DNA segment or at least provides reduced target site specificity from the wild-type.

A preferred object of the invention is to provide a Tn7 transposable system that achieves simple, efficient, non-specific or random insertion into a given DNA segment, or at least reduced target site specificity compared to the wild-type Tn7.

A preferred object of the invention is to provide a mutation in the Tn7 transposon that confers efficient, simple, non-specific insertion into a given DNA segment, or at least reduced target site specificity compared to the wild-type Tn 7.

A preferred object of the invention is to provide a Tn7 transposable system with a mutation in the TnsC protein encoded in the Tn7 transposon, which mutation allows efficient, simple insertion with reduced target site specificity compared to the wild-type, and preferably allows non-specific insertion into a DNA segment.

Objects of the invention include methods for using the above compositions.

Accordingly, a general object of the invention is to provide a method for efficient, simple, random insertion of a transposable element into a given DNA segment.

A further object of the invention is to provide a method for efficient, simple, random insertional mutagenesis by a transposable element.

A specific object of the invention is to provide a method for efficient, simple, random transposition of a transposable element into a DNA segment, or in which the specificity of transposition is reduced compared to wild-type.

A more particular object of the invention is to provide a method for efficient, simple, random transposition of a transposable element into a DNA segment in which the specificity of transposition is reduced compared to the wild-type by using a transposable system containing a mutation that confers efficient, simple insertion with reduced target site specificity compared to the wild-type, and preferably random insertion.

A more particular object of the invention is to provide a method for efficient, simple, random transposition of a transposable element into a DNA segment or in which the specificity of transposition is reduced compared to wild-type, by using a transposable system with a mutation in an ATP-utilizing regulatory protein, the mutation allowing the efficient, simple, non-specific insertion of the transposable element into a DNA segment or at least providing for reduced target site specificity compared to the wild-type.

A preferred object of the invention is to provide a method for efficient, simple transposition of a transposable element into a DNA segment in which the specificity of transposition is reduced compared to wild-type, or is preferably random, by providing a Tn7 transposable system that is capable of non-specific insertion into a DNA segment, or at least reduced target site specificity compared to the wild-type Tn 7.

A further object of the invention is to provide a method for efficient, simple transposition of a transposable element transposon into a DNA segment in which specificity of transposition is reduced compared to wild-type or is preferably random by providing a Tn7 mutation that confers the efficiency, ability to make a simple insertion, and the randomness or reduced specificity.

A further object of the invention is to provide a method for efficient, simple, random transposition of a transposable element into a DNA segment, or in which the specificity of transposition is reduced compared to the wild-type, by providing a mutation in the TnsC protein encoded in the Tn 7 transposon, the mutation allowing a reduction in target site specificity compared to the wild-type and preferably allowing non-specific or random insertion of the Tn7 transposable element into a DNA segment.

A further object of the invention is to provide a method for DNA sequencing using a transposable system to introduce priming sites at randomly-distributed locations within a fragment of interest where the fragment is larger than the sequence run length.

A preferred object of the invention is to provide a method for DNA sequencing using a transposable system with a mutation that allows efficient and simple insertion and target site selectivity that is reduced from the wild-type and preferably random.

A preferred object of the invention is to provide a mutation in an ATP-utilizing regulatory protein. The mutation allows the efficient, simple, non-specific insertion of the transposon into a DNA segment or at least provides reduced target site specificity over wild-type.

A highly preferred object of the invention is to provide a method for DNA sequencing using a Tn7 transposable system that allows efficient, simple, non-specific insertion into a DNA segment or at least reduced target site specificity compared to the wild-type Tn7.

A highly preferred object of the invention is to provide a method for DNA sequencing using a Tn7 transposable system with a mutation in the TnsC protein, the mutation allowing efficient, simple insertion and a reduction in target site specificity compared to the wild-type and preferably allowing non-specific or random insertion of the Tn7 transposable element into the DNA segment.

A further object of the invention is to provide methods as described above that can be applied to any given DNA segment. These include, but are not limited to, plasmids, cellular genomes, including prokaryotic and eukaryotic, bacterial artificial chromosomes, yeast artificial chromosomes, and mammalian artificial chromosomes, and subsegments of any of these.

An object of the invention is to provide these methods in vitro or in vivo.

A further object of the invention is to provide kits for carrying out the above-described methods using the above-described transposons or parts thereof.

The inventor has accordingly developed a transposable system and methods that improve on in vitro and in vivo transmission methods previously described in that the methods are efficient for transposition, provide relatively random insertion, and almost all products recovered are simple insertions at a single site which thus provide useful information.

In a general embodiment of the invention, the invention is directed to a transposable system that achieves simple, efficient, random insertion into a given DNA segment.

In a further embodiment of the invention, the invention is directed to a transposable system that is capable of efficient random insertional mutagenesis, preferably by means of a simple insertion.

In a specific embodiment of the invention, the invention is directed to a transposable system with target site specificity that is reduced from the wild-type and preferably random, which allows simple and efficient insertion.

In a further specific embodiment of the invention, the invention is directed to a transposable system containing a mutation that allows target site specificity that is reduced from the wild-type and is preferably random.

In a preferred embodiment of the invention, the invention is directed to a transposable system with a mutation in an ATP-utilizing regulatory protein, the mutation allowing the efficient, simple, non-specific insertion of the transposon into a DNA segment or at least providing reduced target site specificity from the wild-type.

In a highly preferred embodiment of the invention, the invention is directed to a Tn7 transposable system that achieves efficient, simple, non-specific insertion into a given DNA segment, or at least reduced target site specificity compared to the wild-type Tn7.

In a highly preferred embodiment of the invention, the invention is directed to a mutation in a Tn7 transposon that confers the capability of efficient, simple, non-specific insertion into a DNA segment, or at least reduced target site specificity compared to the wild-type Tn7.

In a highly preferred embodiment of the invention, the invention is directed to a mutation in the TnsC protein encoded in the Tn7 transposon, the mutation allowing simple, efficient insertion and a reduction in target site specificity compared to the wild-type and preferably allowing non-specific or random insertion of the Tn7 transposition into a DNA segment.

In a specific disclosed embodiment of the invention, the invention is directed to a Tn7 mutant designated TnsC$^{A225V}$, which is a mutant having an alanine to valine substitution at amino acid number 225 in the TnsC gene.

The invention also embodies methods for using all of the above compositions. Methods are directed to transposition or insertion of the transposable elements described above.

Accordingly, in one embodiment, the invention provides generally for efficient, simple, random insertion of a transposon into a given DNA segment, or at least insertion with reduced specificity compared to the wild-type.

In a further embodiment of the invention, the invention is directed to methods for insertional mutagenesis using a transposable system that is capable of efficient, simple, random insertion or at least insertion with reduced specificity compared to wild-type.

In a further embodiment of the invention, the invention is directed to methods for insertion of a transposable element into a DNA segment in which target site specificity is reduced from wild-type and is preferably random, where insertion is efficient and simple.

In a further embodiment of the invention, the invention is directed to methods for insertion of a transposable element into a DNA segment, by providing a transposable element containing a mutation that allows efficient and simple insertion and target site specificity that is reduced from the wild-type and is preferably random.

In a preferred embodiment of the invention, the invention is directed to methods for inserting a transposable element into a DNA segment by providing a transposable system with a mutation in an ATP-utilizing regulatory protein, the mutation allowing simple, efficient, and non-specific insertion of the transposon into a DNA segment, or at least providing reduced target site specificity from the wild-type.

In a highly preferred embodiment of the invention, the invention is directed to methods for inserting a transposable element into a DNA segment by providing a Tn7 transposable system allowing efficient, simple, non-specific insertion into a given DNA segment or at least reduced target site specificity compared to the wild-type Tn7.

In a highly preferred embodiment of the invention, the invention is directed to a Tn7 transposable system with a mutation that allows simple, efficient, and non-specific insertion of a transposable element into a DNA segment or at least provides reduced target site specificity from the wild-type Tn7.

In a highly preferred embodiment of the invention, the invention is directed to methods for inserting a transposable element into a DNA segment by providing a Tn7 transposable system with a mutation in the TnsC protein, the mutation allowing efficient and simple insertion and a reduction in target site specificity compared to the wild-type and preferably allowing non-specific or random insertion of the Tn7 transposition into a DNA segment.

In a specific disclosed embodiment of the invention, the invention is directed to methods for inserting a transposable element into a DNA segment, by providing the Tn7 mutant TnsC$^{A225V}$.

The invention also provides kits for performing the above-described methods and the methods further described herein. In a preferred embodiment, a kit is supplied whose components comprise a mutant ATP-utilizing regulatory protein derived from a transposon, the mutation allowing efficient, simple, non-specific insertion of the transposon into a given DNA segment. The kit also provides a transposable element which can be found as part of a larger DNA segment; for example, a donor plasmid. The kit can further comprise a buffer compatible with insertion of the transposable element. The kit can further comprise a control target sequence, such as a control target plasmid, for determining that all of the ingredients are functioning properly. For DNA sequencing, the kit can further comprise sequencing extension primers with homology to one or more sites in the transposable element. Primers can have homology to sequences outside the transposable element (i.e. in a target vehicle).

In the kits, the mutant protein may be added as a purified protein product, may be encoded in the transposable element and produced therefrom, or encoded on vectors separate from the transposable segment, to be produced in vivo.

It is to be understood that the invention encompasses transposable systems with varying degrees of reduction of target site specificity from the wild-type which are useful for the purposes of the invention described herein.

BRIEF DESCRIPTION OF THE FIGURES

FIGS. 9A–C. Structure of Tn$\underline{7}$ donor plasmids. A. A plasmid contains a miniTn$\underline{7}$ element in which the essential cis-acting sequences at the element termini flank a selectable marker. The translocation of the element can be readily followed by hybridization to a miniTn specific probe. Many different kinds of information could be inside the ends as a selectable (or identifable marker, for example, an antibiotic resistance gene. If the products of transformation are to be recovered in vivo, it is convenient to remove unreacted donor DNA by digestion with a restriction enzyme that is selective for the donor backbone; alternatively a conditional replicon can be used. B. Sequence of Donor plasmid pEM delta R.adj to 1 (SEQ ID NO:3). Plasmid carries a 1625 bp mini-Tn$\underline{7}$ element: 199 bp of Tn$\underline{7}$R and 166 bp of Tn7L flank a Kan gene with SalI sites at the junctions. The backbone is pTRC99 (Pharmacia); mini-Tn$\underline{7}$ plus flanking host DNA was cloned into the SmaI site. C. A commonly used derivative is pEM-Δ, (SEQ ID NO:4) a pBR plasmid containing a kanamycin mTn$\underline{7}$ element.

FIGS. 10A–B. Tn$\underline{7}$ target plasmids. A. Sequence of Target plasmid pER 183 (SEQ ID NO:5). This 8.9 kb pACYC184 derivative carries chloramphenicol resistance, a p15A origin of replication, and inserts carrying mcrB, mcrC, hsdS, and a segment of phage f1. A large target was used to detect preference of moderate complexity (up to four bp preferences should be detectable). In addition, different segments of the plasmid vary in G+C content from 35% to 68%, so that any preference the transposition system might display for a particular G+C content might be revealed. B. The major targets used in this work are pRM2 (SEQ ID NO:6), a 3190 bp pBR derivative containing at attTn$\underline{7}$ segment and pER183 (SEQ ID NO:5), a pACYC derivative containing several E. coli genes.

FIG. 13. The base composition of the 5bp sequences duplicated by the process of Tn7 insertion for the 63 sites examined. On the abcissa, sequence positions are numbered relative to the right end of Tn7 (Tn7R) such that position 1 is immediately adjacent, position 5 is 5bp away (see diagram below the graph). On the ordinate is the number of instances of a particular base at that position. All bases are well represented at all sites.

FIGS. 18. 18A. nucleotide sequence of TnsC (SEQ ID NO:1). 18B. Amino acid sequence of TnsC (SEQ ID NOS:1 and 2).

DETAILED DESCRIPTION OF THE PREFERRED EMBODIMENTS

Figure 1:
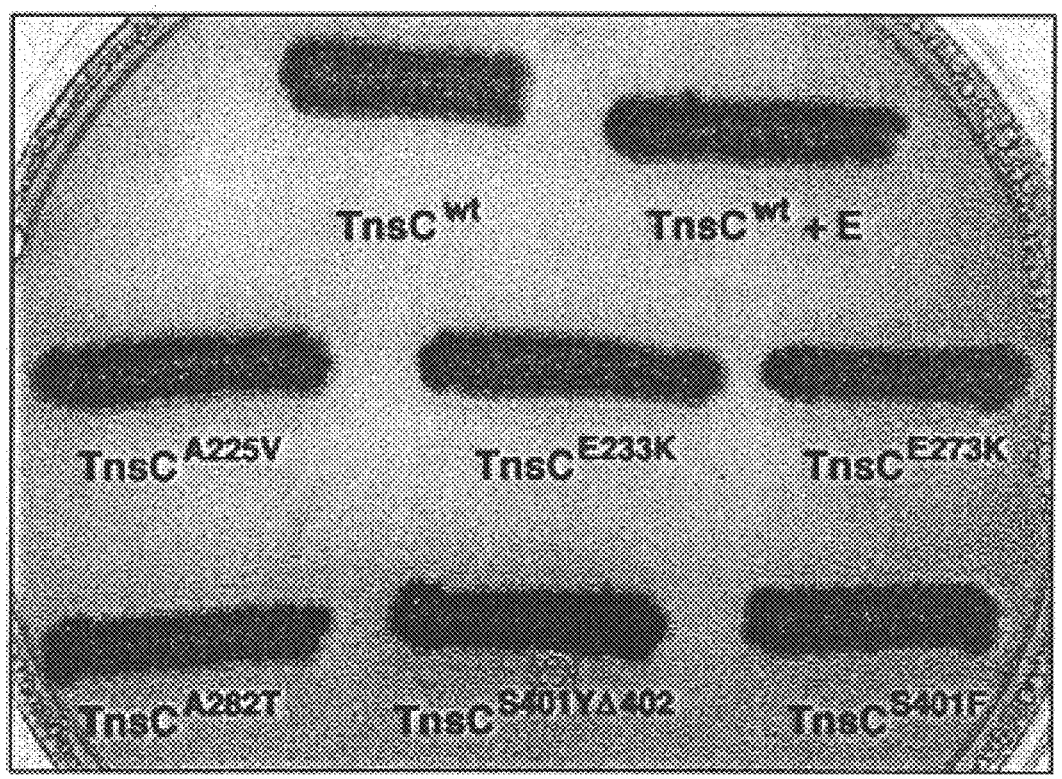
FIG. 1. Papillation phenotypes of the TnsC gain-of-function mutants. Cells were patched on MacConkey lactose plates and photographed after three days' incubation at 30° C. TnsA+B was present in each strain; the TnsC species present is indicated below each patch.

In the art, the term "transposon" encompasses a segment flanked by particular cis-acting sites that are required for mobilization to occur, together with the genes that specify the proteins that act on those cis-acting sites to mobilize the segment defined by them, whether or not the protein-encoding genes lie between the sites mentioned. For example, according to the present invention, a Tn7 transposon can correspond to the wild type transposon except that the transposon encodes a mutant TnsC. This transposon thus provides the protein products required for mobilization. However, an entire transposon is not necessary to practice the invention. Thus, the term "transposon derivative", "transposable element", or "insertable element" as used herein can also refer to DNA minimally comprising the cis-acting sites at which the trans-acting proteins act to mobilize the segment defined by the sites. It is also understood that the sites may contain intervening DNA.

The phrase "transposable system" as used herein encompasses a transposon containing a mutation in a native ATP-utilizing regulatory protein which, when expressed from the transposon, allows for the non-specific target site selectivity or reduced target site selectivity disclosed herein. The phrase also encompasses modifications in which the relevant proteins are not encoded on the transposable element but nevertheless, acts upon it to achieve the objects of the invention. Thus, the system encompasses compositions in which the mutant protein is added to a transposable element that is derived from a transposon but where the element contains less than the full complement of genes. The only limitation on this element is that it contain the cis-acting sequences upon which the mutant protein acts that allows integration of the element into a target DNA. Thus, the system comprises DNA with cis-acting sites (which may contain heterologous DNA sequences) and the transacting proteins that employ those sites to mobilize the segment defined by the sites, regardless of how they are organized in DNA. Accordingly, the proteins may be provided in separate plasmids or in purified form.

The term "transposon-derived" as used herein to refer to the mutant protein, refers to a derivative of a protein normally found on the transposon. However, this need not be the naturally occurring protein but can be the protein produced by recombinant or chemical synthetic methods known to those in the art.

The term "transposable element" encompasses both transposons and derivatives thereof. The only limitation on the derivative is that it is capable of integrating into DNA, containing cis-acting sequences that interact with transacting proteins to effect integration of the element.

The invention provides a transposable system that allows simple integration of a transposable element into a given DNA target efficiently and with a relatively low degree of specificity, preferably random specificity. By "relatively" is intended the degree of specificity compared to the wild-type.

The efficiency of integration can vary depending upon the particular use for which insertion is desired. The mutations described herein increase the efficiency of integration compared to the wild-type frequency. The invention encompasses an efficiency of one simple integration event per every 5–10 kilobases. Preferred levels of integration allow multiple simple insertions in different positions in every gene.

Integration is also effected by the degree of specificity that the mutation confers or allows. Thus, specificity relates to the relationship of a target DNA sequence and the transposable system.

A preferred degree of specificity results in an average insertion in every gene. A practical lower limit would be, on average, one insertion per twenty genes.

For sequencing, greater than or equal to 90% of the insertions screened are at different locations (i.e. 10 insertions hit at least 9 different sites) so that almost every template examined gives new information. This is true in DNAs of a variety of different base compositions since possible target DNAs may vary between 20% and 80% G+C. Another way to describe the possible randomness of the system is to say that of 63 insertions, 62 insertion sites were found (around 98% of insertions are at different locations).

For mutagenesis, non-commercial systems have been widely used that yield as little as 10% of insertions at different sites (i.e. 9 of 10 insertions are at the same site). The present invention improves on this level of randomness.

Furthermore, the types of insertions that are relevant to the discussion of frequency are simple insertions.

The invention provides a transposable system with a mutation that provides for efficient, simple insertion and reduced or random target site specificity.

The term "simple insertion" refers to a single copy integration event of the element introduced into the target by double-strand breakage and rejoining.

Although simple insertions (only one copy of the integrant) are preferred, there may be certain embodiments in which more than one copy does not interfere with the purpose of the application, for example some applications of in vitro mutagenesis, or is actually desirable (for example, for multiple copies of a heterologous DNA sequence are to be inserted). Accordingly, the invention is not limited to the case in which the transposable system provides for simple insertion only.

In a preferred embodiment of the invention the mutation is in a transposon-derived ATP-utilizing regulatory protein. One can recognize such a protein by its similarity to the TnsC protein of Tn7, that is by its sequence homology, its possession of a protein sequence motif element similar to an ATP binding site motif in other ATP-dependent proteins, or by reconstitution of an in vitro transposition system and demonstration of a requirement for nucleotides in that in vitro transposition system.

In a highly preferred embodiment, the mutation is in the TnsC gene (SEQ ID NO: 1) encoding the TnsC protein (SEQ ID NOS:1 and 2)of Tn7. This mutation provides a Tn7 transposon that is capable of relatively non-specific insertion into a given DNA segment.

Thus, the invention is directed to insertion of the Tn7 transposable element but is not limited to this transposable element. Accordingly, the invention can be practiced with transposable elements related to Tn7 in that transposition occurs by means of an ATP-mediated process. Thus, mutations in the ATP-utilizing proteins in such transposons is contemplated in this disclosure. Accordingly, transposons with ATP-utilizing regulatory proteins in addition to Tn7 are encompassed in the invention. Examples of such transposons are Tn5090/Tn420; the transposon-encoded transposition proteins are TniA, TniB, and TniQ. The TniB would be the ATP-utilizing protein.

Another class of transposon is encompassed by the invention in which it is possible to increase the frequency by altering the ATP-utilizing proteins examples are Tn552 and IS21.

The invention provides for the insertion of the transposable elements described herein into any DNA segment of any organism. Moreover, the invention also provides for the insertion into any synthetic DNA segment.

Insertion of the transposable element can be in vivo. In this case, the transposable element is introduced into a desired host cell, where it inserts directly into DNA in that cell. The only limitation is that the transposable element be capable of insertion in the specific host cell DNA. Thus, as long as the proteins required for transposition can be expressed in a desired cell, this cell can provide a host for insertion of the transposable element into any DNA found in that host cell.

Insertion can be for the purpose of gene inactivation. Gene inactivation is useful for genetic analysis (e.g. gene function).

Genetic analysis includes:

assessment of the phenotype of a null allele (not expressing functional protein due to interruption of the gene by the transposable segment);

assessment of the consequences of insertion of particular active DNA structures or sequences for genetic properties of chromosomes or their parts, such as but not limited to accessibility to Dnase I or to footprinting reagents, or expression or silencing of nearby transcribable genes, or for activity of genetic or epigenetic processes such as, but not limited to homologous recombination, chemical mutagenesis, oxidative DNA damages, DNA methylation, insertion of proviruses or retroposons;

assessment of protein domain structure via creation of multiple interruption points within a gene for a multidomain protein, wherein a gene product missing one or more domains of the multidomain protein might exhibit partial activity or activities, including antigenic activities or immunodominant epitopes [randomness is paramount here, many insertion positions are needed if borders are to be defined accurately];

assessment of expression pattern via creation of transcriptional fusions of a promoter in the target to a reporter (e.g. beta galactosidase or green flourescent protein or chloramphenicol transacetylase or luciferase) within the transposable segment;

assessment of expression pattern via creation of translational fusions of a portion of a gene product encoded by a target to a gene product or an antigenic peptide encoded by the transposable segment (e.g. beta galactosidase or an epitope tag or an affinity tag);

assessment of operon structure, in which interruption of transcription by insertion upstream of a gene results in altered expression of a gene without disrupting the coding sequence of that gene;

gratuitous expression of a gene, in which transcription from a promoter within the transposable segment results in expression of a gene downstream of the position of insertion of the transposable segment, with or without regulation of transcription of the promoter within the transposable segment;

gratuitous expression of a protein fusion, in which transcription from a promoter within the transposable segment results in translation of a protein beginning within the transposable segment and proceeding toward the outside of the transposon, then continuing into the gene within which the transposable segment is inserted, resulting in a fusion of the transposon-encoded protein with the target protein;

assessment of the consequences of introducing into the host cell any transcript or gene product entirely encoded within the transposable segment, especially where it is desirable to assess position-effects (the consequences not only of expression but of expression in different positions within the genome).

Insertion can also be for the purpose of introducing heterologous DNA sequences into the DNA of a host cell. The DNA in the host cell in which the insertion occurs can be the host genomic DNA or extrachromosomal elements. This includes both naturally-occurring elements and elements introduced exogenously.

Heterologous genes that can be introduced via the insertion include reporter genes. DNA sequences can also be introduced that provide physical markers in a chromosome. Insertion can also be used as a simple way to recover the host DNA that is flanking the inserted element. Genomic DNA is cut with restriction enzymes and the insertion plus the flanking DNA is then cloned.

Another utility or another application of the invention is to analyze the interaction of various non-transposition proteins with a DNA sequence, for example, DNase footprinting of repressors bound to DNA. A further use is to study the structure of genomic chromatin i.e., the state at which DNA is actually found in the cell.

A further advantage in using Tn*7* and similar transposons is that of double end or "concerted" joining. Accordingly, Tn *7* inserts in a "cut and paste" manner with both ends of the transposon being joined to the target DNA.

Insertion can also be in vitro. In vitro insertion provides an advantage over insertion in vivo. Using in vitro insertion, the transposable element can be placed in any DNA target and that target then introduced into a host cell where it can integrate or replicate. Accordingly, this greatly expands the host cell range.

Targets for insertion, accordingly, include DNA fragments, plasmids and other extrachromosomal elements capable of replication in prokaryotic and/or eukaryotic host cells. Given the array of plasmids available, potentially any cell can be used as a host for an insertion target containing a transposable element that was introduced into the target in vitro. The target can be based on a bacterial plasmid, bacteriophage, plant virus, retrovirus, DNA virus, autonomously replicating extra chromosomal DNA element, linear plasmid, mitochondrial or other organelle DNA, chromosomal DNA, and the like.

When introduced into the host cell, the target can be maintained as an autonomously replicating sequence or extrachromosomal element or can be integrated into host DNA. When integrated, integration can occur by homologous recombination or by means of specific integration sequences such as those derived from retroviruses, DNA viruses, and the like.

It may be, but is not necessarily, desirable to obtain replication of the target in the host cell. A specific application in which this is desirable is the case in which a transposable element is used as a component for introducing primer binding sites for DNA sequencing.

Accordingly, in a highly preferred embodiment of the invention, a transposable element is introduced into a target containing a DNA segment for which a sequence is desired. This target is then introduced into a host cell where it is allowed to replicate, thus producing sufficient copies to allow DNA sequencing using a primer specifically recognizing a sequence in the target.

In one embodiment of this method, the primers recognize one or both ends of the transposable element such that sequencing can proceed bidirectionally from the transposable element insertion site into the surrounding DNA. The target may be composed entirely of DNA segments for which the sequence is required or may simply contain subsequences for which a sequence is required. In this aspect the only limitation on the target is that it is able to replicate in the host cell (and therefore contains sequences that allow this to occur).

It is also highly desirable that the target have a selection marker in order to eliminate the background in host cells containing the target without the insertion of the transposon.

An alternative way to eliminate this background, however, is to provide a method for disabling a target that has not received an insertion so that it is unable to replicate in the host cell and is thus diluted out during host cell culture. Accordingly, the transposable element itself could contain an origin of replication for the host cell. Thus targets not receiving an insertion would be unable to replicate. An insertion could also result in the formation of functional replication sequences. The target could also contain a heterologous conditional origin, such as the R6K origin, that cannot replicate without the pir protein. The person of ordinary skill in these arts would be aware of the various methods for constructing targets with the (in)ability to replicate in a specific host cell.

It is also possible, however, to use the transposable elements described herein for DNA sequencing without the in vitro insertion described above. Insertion could be directly accomplished in host cell DNA and then the DNA containing the insertion removed from the host. This DNA segment could then be replicated although it does not necessarily have to be if the host has produced sufficient copies for sequencing. Accordingly, sufficient numbers of the segment with the insertion sequence could then be sequenced as above.

An example of the case in which the DNA segment receiving an in vivo insertion would not need to be further replicated in another host is, for example, a case in which the insertion occurs in a sequence capable of being amplified directly in the host cell. This could be a plasmid containing an amplifiable marker, such as the gene, the cell being grown in a selective medium containing methotrexate. The gene, the cell being grown in a selective medium containing methotrexate. The person of ordinary skill in the art would know the various methods for amplifying DNA segments using selectable markers. The selectable marker could be introduced on the transposon but would not necessarily need to be.

In a further DNA sequencing protocol, the primers that are used facilitate DNA segment amplification by the PCR reaction. For example, a primer can be used that recognizes an end of the transposable element with the second primer being found in the target DNA sequence. The primer could be based on random sequences or on known sequences deliberately placed in the target vehicle. Thus the target vehicle could contain a characterized plasmid (as an example) in which the sequences are known. In this instance, primers can be designed to hybridize to any area within the plasmid, the segment to be sequenced being between the transposon and the second primer site in the target vehicle.

In accordance with the above-described embodiment, the invention is also directed to kits for performing transposable element insertion in vitro. As described, such insertions can be used to provide priming sites for DNA sequence determination or to provide mutations suitable for genetic analysis or both.

Essential components in the kit are gene products allowing transposition that are normally encoded on the transposable element or their functional equivalents. A further component is a transposable element donor vehicle. This nucleic acid vehicle provides the transposable element to be inserted into a given specific target. The transposable element donor is preferably DNA but could encompass RNA, being operable via a cDNA copy. Preferred DNA vehicles include, but are not limited to, bacterial plasmids. Other vehicles include any DNA that can be isolated in super coiled form or placed into a super coiled configuration by the use of topoisomerases, for example, bacteriophaged DNA, autonomously replicating molecules from eukaryotes or archae, or synthetic DNA that can be ligated to form a topologically closed circle.

Optional components of the kit include one or more of the following: (1) buffer constituents, (2) control target plasmid, (3) sequencing primers. The buffer can include any buffer suitable for allowing the transposition activity to occur in vitro. A preferred embodiment is HEPES buffer. A specific disclosed embodiment is included in the exemplary material herein.

Preferred donor plasmids do not need to be destroyed before introducing transposition products into commonly used bacterial and preferably E. coli strains. These vectors do not replicate without regulatory genes not provided by the host cell which allow a functional replication origin. An example is the pir gene which is present only in specially constructed strains, having been derived from the plasmid R6K. In this way, artifactual background consisting of cells transformed with both the donor DNA and the target DNA without any transposition having occurred is eliminated. As discussed herein, there are other ways to do this such as restriction digestion of the donor DNA but not of the target or transposable segment or deletion and titration of the transposition reaction so that there are more cells than DNA molecules in the transformation step. However, these are not preferred.

The control target plasmid does not contain the transposable element and does contain transposable element integration site. The purpose is to assure that the reaction is not inhibited by a contaminant in non-kit ingredients (introduced by the kit user); i.e. it ensures that all components allow optimal insertion.

Sequencing primers include, but are not limited to primers that have homology with both ends of the transposable element and, as such, allow sequencing to proceed bidirectionally from the ends of the transposable element. However, primers could be made to any area within the transposable element or within the target vehicle itself as long as extension is allowed into the DNA segment to be sequenced. Kits designed for allowing sequencing by the PCR reaction may also include a second primer that allows the amplification of the sequence between the first and second primers.

The control target plasmid preferably contains a selectable marker for recovery of the desired DNA segment from a specific host cell. It is understood that, when using the kit, the target DNA does not carry the same selectable marker as the control target nucleic acid.

A fourth optional component of a kit is target DNA itself. Target DNA that might be desirable would include but is not limited to purified chromosomal DNA, total cDNA, cDNA fractionated according to tissue or expression state (e.g. after heat shock or after cytokine treatment other other treatment) or expression time (after any such treatment) or developmental stage, or plasmid, cosmid, BAC, YAC or phage library of any of the foregoing DNA samples, especially such target DNA from important study organisms such as *Homo sapiens, Mus domesticus, Mus spretus, Canis domesticus,* Bos, *Caenorhabditis elegans, Plasmodium falciparum, Plasmodium vivax, Onchocerca volvulus, Brugia malayi, Dirofilaria immitis,* Leishmania, *Zea maize, Arabidopsis thaliana, Glycine max, Drosophila melanogaster, Saccharomyces cerevisiae, Schizosaccharomyces pombe,* Neurospora, *Escherichia coli, Salmonella typhimurium, Bacillus subtilis, Neisseria gonorrhoeae, Staphylococcus aureus, Streptococcus pneumonia, Mycobacterium tuberculosis,* Aquifex, *Thermus aquaticus, Pyrococcus furiosus, Thermus littoralis, Methanobacterium thermoautotrophicum, Sulfolobus caldoaceticus,* and others.

Other suitable selectable markers include chloramphenicol resistance, tetracycline resistance, spectinomycin resistance, streptomycin resistance, erythromycin resistance, rifampicin resistance, bleomycin resistance, thermally adapted kanamycin resistance, gentamycin resistance, hygromycin resistance, trimethoprim resistance, dihydrofolate reductase (DHFR), GPT; the URA3, HIS4, LEU2, and TRP1 genes of S. cerevisiae.

There may be certain instances in which it is desired to introduce primer binding sites other than those naturally found in the transposable element or in the insertion vehicle. In this case, the transposable element can be used as a vehicle for introducing any desired primer or primers. An example of when the use of exogenous primers may be desirable is the case in which the transposable element ends form a secondary structure that interferes with sequencing, or cases in which there is a similarity of sequence between the two ends of the transposable element, and cases in which the only practical binding sites in the transposable element are so far internal that they undesirably curtail the amount of nucleotides that can be sequenced from that site.

The invention also generally encompasses compositions containing an ATP-dependent DNA binding protein encoded by a transposon, the protein containing a mutation conferring reduced target site specificity, preferably random target site insertion.

The protein is isolated from a biological preparation produced in vivo or in vitro. Thus, the protein is purified or substantially purified from cellular components with which it is found in vivo. When produced in vitro, the protein may also be purified or substantially purified from the other components used to produce it.

In preferred embodiments the protein is the TnsC protein (SEQ ID NOS:1 and 2).

In a specific disclosed embodiment, the protein contains a valine at amino acid number 225.

The invention is also directed to compositions containing the protein described herein and the transposable element substrate on which the protein acts to cause insertion.

Compositions can also include target DNA into which the transposable element is capable of being inserted.

The mutant proteins of the present invention include the naturally occurring proteins encoded by a transposon as well as any substantially homologous and/or functionally equivalent variants thereof. By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, (37) (38) (39) (40); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) (41) in *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the protein of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

Thus nucleotide sequences of the invention and the proteins encoded thereby include the naturally occurring forms as well as variants thereof. The variant proteins will be substantially homologous and functionally equivalent to the native protein. A variant of a native protein can be "substantially homologous" to the native protein when at least about 80%, more preferably at least about 90%, and most preferably at least about 95% of its amino acid sequence is identical to the amino acid sequence of the native protein. However, substantial homology includes high homology in the catalytic or other conserved functional regions with possible low homology outside these. By "functionally equivalent" is intended that the sequence of the variant defines a chain that produces a protein having substantially the same biological effect as the native protein of interest. Thus, for purposes of the present invention, a functionally equivalent variant will confer the phenotype of activating transposition with reduced target site specificity, preferably random. Such functionally equivalent variants that comprise substantial sequence variations are also encompassed by the invention.

The invention also encompasses compositions containing a transposable element containing DNA sequence encoding an ATP-utilizing regulatory protein, the protein containing a mutation that confers reduced target site specificity and preferably random insertion.

In preferred embodiments of the invention, the transposable element is a Tn7 transposable element.

In specific disclosed embodiments, the mutation is valine as amino acid number 225 in the TnsC protein.

The invention also encompasses compositions containing the above-described transposable element and a given DNA segment intended to be the target for insertion of the transposable element.

The invention, accordingly, is directed to DNA into which has been inserted the transposable element containing the mutation described herein that confers simple, efficient insertion with reduced target site specificity or random target site insertion. The DNA in this composition, in one embodiment, is capable of being introduced into a cell in which it can exist as an extrachromosomal element or as an integration element into cellular DNA.

The invention is also directed to DNA segments encoding the mutant proteins disclosed herein, vectors containing these segments and host cells containing the vectors. The vectors containing the DNA segments may be used to propagate (i.e. amplify) the segment in an appropriate host cell and/or to allow expression from the segment (i.e. an expression vector). The person of ordinary skill in the art would be aware of the various vectors available for propagation and expression of a cloned DNA sequence. In a preferred embodiment, a DNA segment encoding mutant TnsC protein is contained in a plasmid vector that allows expression of the protein and subsequent isolation and purification of the protein produced by the recombinant vector. Accordingly, the proteins disclosed herein can be purified following expression from the native transposon, obtained by chemical synthesis, or obtained by recombinant methods.

Relevant compositions, accordingly, include expression vectors for the mutant protein alone or in combination with expression vectors for the other proteins necessary for insertion of a transposable element. Such compositions may further comprise the transposable element to be acted upon by the proteins. Such mixtures are useful for achieving in vivo insertion, among other things.

The invention further encompasses kits containing the above-described compositions.

Tn7 can be obtained as strain ATCC 29181; a K-12 derivative carrying the resistance transfer factor R483; originally identified as carrying a transposon in Barth et al. *J. Bacteriol.* 125:800–810 (1976). The sequence of Tn7 is Genbank entry ISTN7TNS, Assession no. X17693; reported in Flores et al. *Nucleic Acids Res.* 18:901–11 (1990).

Having now generally described this invention, the same will be further described by reference to certain specific examples which are provided herein for purposes of illustration only and are not intended to be limiting unless otherwise specified.

EXAMPLES

Example 1

Materials and Methods

Media, chemicals, and enzymes: LB broth and agar were prepared as described (42). Trimethoprim selection was on Isosensitest agar (Oxoid). Lac phenotypes were evaluated on MacConkey lactose agar (Difco). Antibiotic concentrations used were 100 $\mu$g/ml carbenicillin (Cb), 30 $\mu$g/ml chloramphenicol (Cm), 7.5 $\mu$g/ml gentamycin (Gn), 50 $\mu$g/ml kanamycin (Km), 10 $\mu$g/ml nalidixic acid (Nal), 20 $\mu$g/ml tetracycline (Tet) and 100 $\mu$g/ml trimethoprim (Tp). Hydroxylamine was purchased from Sigma. DNA modifying enzymes were purchased from commercial sources and used as recommended by the manufacturer.

Bacterial strains, phages and plasmids: BR293 is *E. coli* F$^-$ $\Delta$(lac-pro) thi rpsL $\Delta$(gal-$\lambda$G)+lacZ pL cI+$_{434}$ pRS$_7$ (43) (44). BR293 is identical to NK8027 (45), and was provided by Nancy Kleckner. NLC51 is *E. coli* F$^-$ araD139 $\Delta$(argF-lac) U169 rpsL150 relA1 flbB5301 deoC1 ptsF25 rbsR Val$^R$ recA56 (46). CW51 is *E. coli* F$^-$ ara arg $\Delta$lac-proXIII recA56 Nal$^R$ Rif$^R$ (11). $\lambda$KK1 is lambda 780 hisG9424::Tn10 del16 del17::attTn7::miniTn7-Km$^R$ (47). Tns transposition proteins were provided by pCW1 5 (tnsABC), pCW23 (tnsD), pCW30 (tnsE), or pCW4 (tnsABCDE) (11). Target plasmids were derivatives of pOX-G, a conjugable derivative of the F plasmid that carries Gn$^R$ (48). pOX-attTn7 carries a (−342 to +165) attTn7 sequence (16). The immune plasmid pOX-attTn7 EP-1::miniTn 7-Cm$^R$ was made by transposing miniTn7-Cm$^R$ (47) onto pOX-attTn7 using TnsABC+E to direct the insertion into a non-attTn7 position. Construction of the immune target plasmid pOX-G::miniTn7-dhfr is described below. The transposon donor plasmid for the papillation assay was pOX-G::miniTn7lac, containing promoterless lacZY between the transposon ends (50). The high copy transposon donor for mating-out assays was pEM$\Delta$, containing miniTn 7-Km$^R$ (23).

Manipulation and characterization of DNA: Phage and plasmid isolation, transformation, and standard cloning techniques were performed as described in (40). Conjugation and P1 transduction were performed as described in (42). DNA sequencing was done on an automated ABI sequencer. Two plasmids were constructed in this work: (1) pOX-G::miniTn7-dhfr. MiniTn7-dhfr was constructed by replacing the $Km^R$ cassette in pLA1 (16) with a dhfr cassette from pSD511 (28), which had been amplified by PCR to add flanking SalI sites. The PCR fragment was ligated into the TA vector (Invitrogen), the dhfr cassette was then removed by SalI digestion and inserted into the SalI site of pLA1, replacing the $Km^R$ gene. The resulting plasmid was transformed into NLC51+pCW4+pOX-G, and grown for several days to allow transposition to occur. pOX-G plasmids which had received a miniTn7-dhfr insertion were identified by mating into CW51 and selecting for $Tp^R$.

Mutagenesis of tnsC: The TnsABC plasmid pCW15 was exposed to 1M hydroxylamine hydrochloride in 0.45 M NaOH (final pH approximately 7.0) at 37° C. for 20 hours (ROSE et al. 1990). The DNA was recovered by multiple ethanol precipitations, and PvuII-SphI fragments containing mutagenized tnsC were subcloned into untreated pCW15, replacing the wild-type TnsC (SEQ ID NO:1). These plasmids were then introduced into CW51+pOX-G::miniTn7lac by electroporation, and transformants were selected on MacConkey lactose plates containing Cm. The plates were incubated at 30° C. for 3–4 days, and screened for the emergence of Lac$^+$ papillae, indicating transposition of miniTn7lac.

λ hop transposition assay: Tn7 transposition was evaluated in NLC51 strains into which tns functions were introduced by transformation, and pOX-G was introduced by conjugation (for FIG. 5). The protocol of (47) was followed: Cells were grown in LB and 0.2% maltose at 37° C. to an $OD_{600}$ of 0.4–0.6 and then concentrated to $1.6 \times 10^9$ cells/ml by centrifugation and resuspension in 10 mM $MgSO_4$. 0.1 ml cells were combined with 0.1 ml λKK1 containing miniTn7-$Km^R$ at a multiplicity of infection of 0.1 phage per cell. The infection proceeded for 15 min at 37° C., and was terminated by the addition of 10 mM sodium citrate in 0.8 ml LB. Cells were allowed to recover with aeration for 60 minutes at 37° C., and then spread on plates containing Km and citrate. Transposition frequency is expressed as the number of $Km^R$ colonies/pfu of λKK1.

Mating-out transposition assay: Tn7 transposition was evaluated in the derivatives of BR293 used to monitor SOS induction (Table 3), or in NLC51 strains into which tns functions were introduced by transformation, and pOX-G or pOX-G::miniTn7-dhfr were introduced by conjugation. MiniTn7-$Km^R$ was present in the NLC51 strains either in the chromosomal attTn7 site (FIG. 4 and Table 1) or the high copy plasmid pEMΔ(Table 2). The protocol was adapted from (11): The donor strains described above and the recipient strain CW51 were grown at 37° to an $OD_{600}$ of 0.4–0.6 with gentle aeration. Donors and recipients were mixed at a ratio of 1:5, and growth was continued for another hour. Mating was disrupted by vigorous vortexing, and the cells were diluted and plated. The total number of exconjugants was determined by selection on GnNal plates. Tn 7-containing exconjugants were selected on TpNalplates, and miniTn7-$Km^R$ exconjugants were selected on KmNal plates. Transposition frequencies are expressed as the number of $Tp^R$- or $Km^R$- exconjugants/total number of exconjugants.

Results

Isolation of the TnsC gain-of-function mutants: To focus on the relationship of TnsC and the target DNA, the inventor isolated gain-of-function TnsC mutants that activated the TnsA+B transposase in the absence of TnsD or TnsE. Since overexpression of wild-type TnsC does not relieve the requirement for TnsD or TnsE (11), these gain-of-function mutations were predicted to affect the biochemical properties of TnsC, rather than its expression or stability.

A visual assay for Tn7 transposition (50) (51) was used to identify mutants. This assay uses a miniTn7lac element which carries promoterless lacZY genes between the cis-acting sequences at the transposon ends. The miniTn7lac element is located in a transciptionally silent position on a donor plasmid; cells containing this plasmid are phenotypically Lac$^-$. When Tns functions are provided in trans, miniTn7lac can transpose to new sites in the E. coli chromosome. Some of those transposition events place the element downstream from active promoters, resulting in increased lacZ expression. This is observed on MacConkey lactose color indicator plates as the emergence of red (Lac$^+$) papillae in an otherwise white (Lac$^-$) colony. Therefore, the number of papillae reflects the amount of transposition which occurred during the growth of that colony.

Cells containing miniTn7lac and various Tns functions were patched on color indicator plates (FIG. 1). Virtually no Lac$^+$ papillae were seen in cells containing only TnsABC$^{wt}$. Cells containing TnsABC$^{wt}$+E produced many Lac$^+$ papillae. Southern blotting demonstrated that TnsABC$^{wt}$+E papillae result from translocations of miniTn7lac to a variety of chromosomal locations rather than from intramolecular rearrangements of the donor plasmid (50). Most TnsABC$^{wt}$+D events are silent because there is no appropriately oriented promoter adjacent to attTn7 (50) (52).

This visual assay was used to screen for TnsC mutants that had acquired the ability to activate Tn7 transposition in the absence of TnsD or TnsE. Randomly mutagenized tnsC was cloned into a plasmid containing tnsAB. These tns genes were introduced into cells containing miniTn7lac. Six gain-of-function TnsC mutants were identified (FIG. 1).

Transposition activated by these TnsC mutants still required the TnsA+B transposase and intact transposon ends. The papillation phenotypes of the TnsC mutants varied considerably, suggesting that different mutants were activating different amounts of miniTn7lac transposition. Several TnsC mutants promoted more transposition than TnsABC$^{wt}$+E. TnsABC$^{S401YA402}$ achieved the highest level of transposition.

The amino acid changes responsible for the mutant phenotypes were determined by DNA subcloning and sequencing. tnsC encodes a protein of 555 amino acids, with Walker A and B motifs in the amino-terminal half of the protein (53). Walker A and B motifs have been implicated by structural and mutational analyses to be directly involved in nucleotide binding and/or hydrolysis in a variety of ATPases and GTPases (37) (55).

Figure 2:
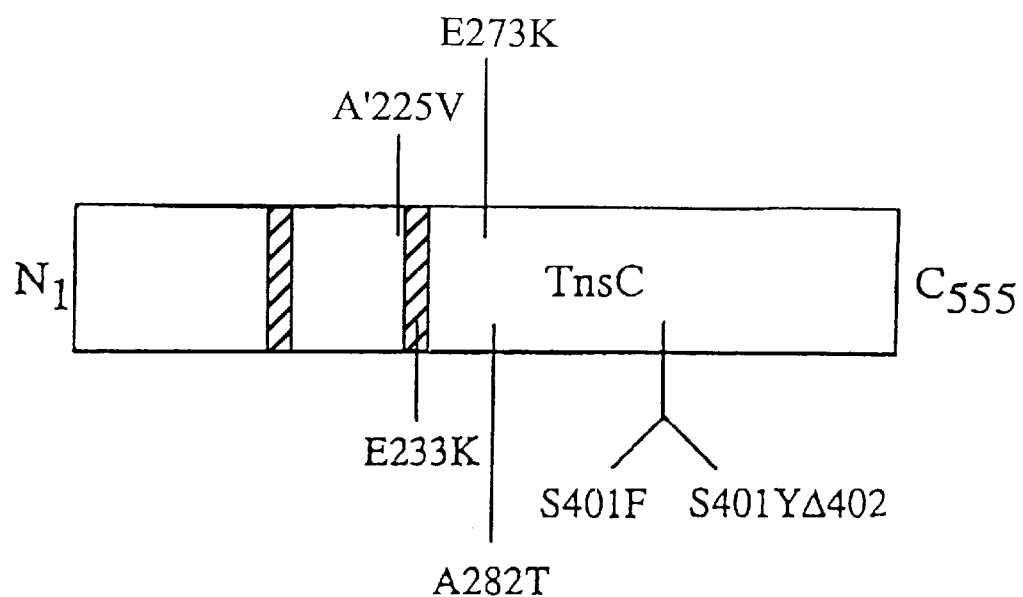
FIG. 2. Amino acid changes in the TnsC mutants. The TnsC protein sequence (SEQ ID NOS:1 and 2) is cartooned, with the residues altered in the Class I mutants indicated above the protein and the Class II mutants below the protein. Hatched boxes represent Walker A and Walker B motifs.

The tnsC mutations primarily result in single amino acid substitutions whose locations are scattered across the TnsC protein sequence (FIG. 2). TnsC mutants segregate into two phenotypic classes. Transposition reactions activated by Class I mutants are sensitive to immune targets and the target selection factors TnsD and TnsE. Transposition reactions activated by the Class II mutants are impaired in their responses to these signals. The residues affected in two of the mutants (TnsC$^{A225V}$ and TnsC$^{E233K}$) lie in or very close to the Walker B motif.

TnsC mutants promote intermolecular transposition: The papillation assay is a powerful screen for transposition activity, but it does not necessarily report intermolecular transposition events. Internal rearrangements of the miniTn7lac donor plasmid, which fortuitously place the miniTn7lac element downstream from a promoter, would also produce Lac⁺ papillae. Therefore, the inventor investigated whether the TnsC mutants facilitate the TnsA+B transposase to do intramolecular recombination, or whether the mutants promote intermolecular transposition.

Figure 3:
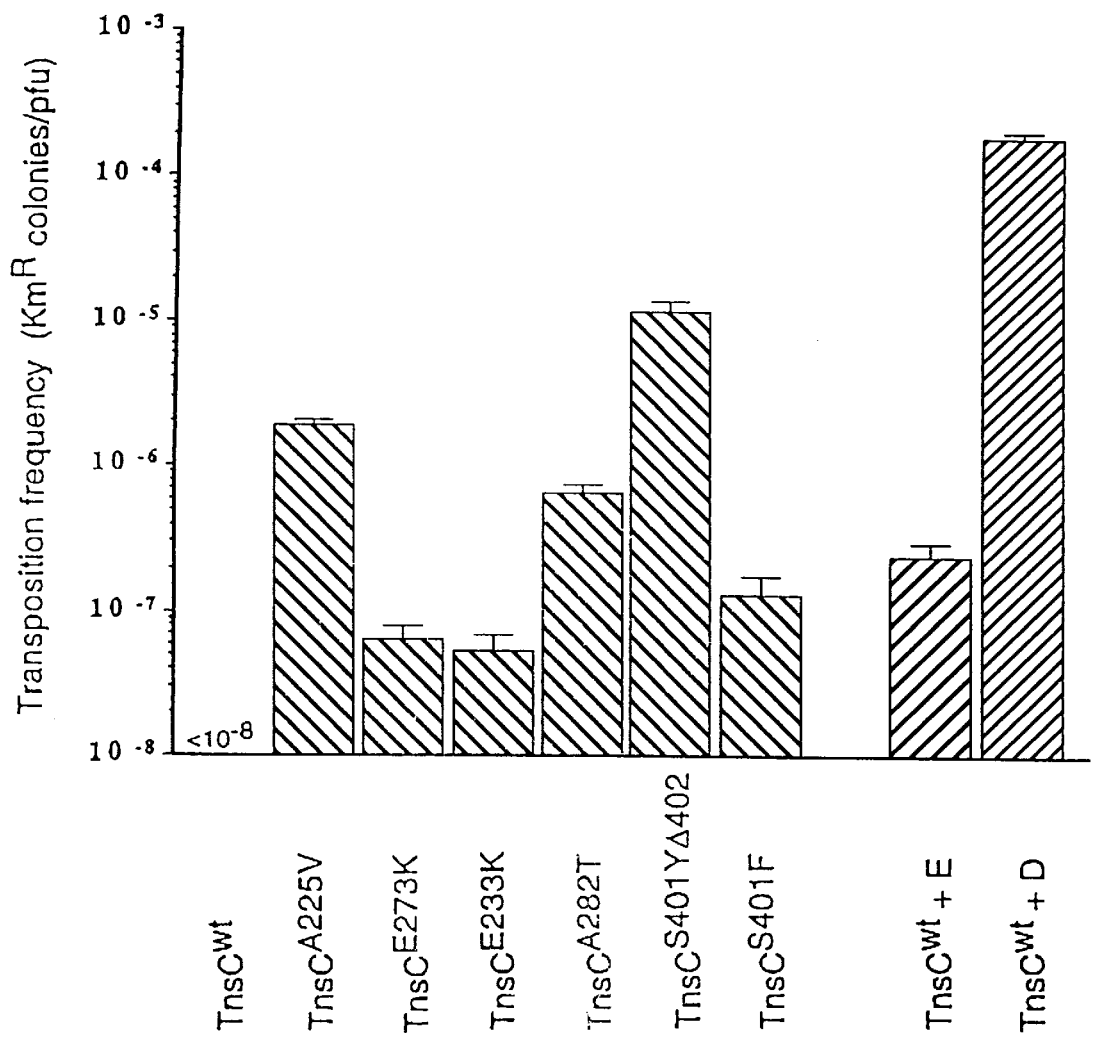
FIG. 3. TnsC mutants promote transposition to the chromosome. Frequencies of transposition of miniTn$\underline{7}$-Km$^R$ from a λ phage to the chromosome were measured by the λ hop assay. TnsA+B was present in each strain; the TnsC species present is indicated below each column.

The λ hop assay measures the translocation of a miniTn7-Km$^R$ element from a replication- and integration-defective λ phage to the bacterial chromosome during a transient infection. The miniTn7-Km$^R$ element carries a kanamycin resistance cassette with a constitutive promoter. Therefore, the λ hop assay reports the total number of transposition events occurring into the chromosome. TnsABC$^{wt}$ had no detectable transposition activity in the λ hop assay. TnsABC$^{wt}$+E generated $2.2 \times 10^{-7}$ Km$^R$ colonies/pfu (FIG. 3). Transposition promoted by TnsABC$^{wt}$+D generated $1.8 \times 10^{-4}$ Km$^R$ colonies/pfu. All of the TnsC mutants could promote the translocation of miniTn7-Km$^R$. TnsABC$^{A225V}$ and TnsABC$^{S404Y\Delta402}$ promoted 8- and 50-fold more transposition than TnsABC$^{wt}$+E. Other TnsC mutants promoted transposition, although not at such levels.

Figure 4:
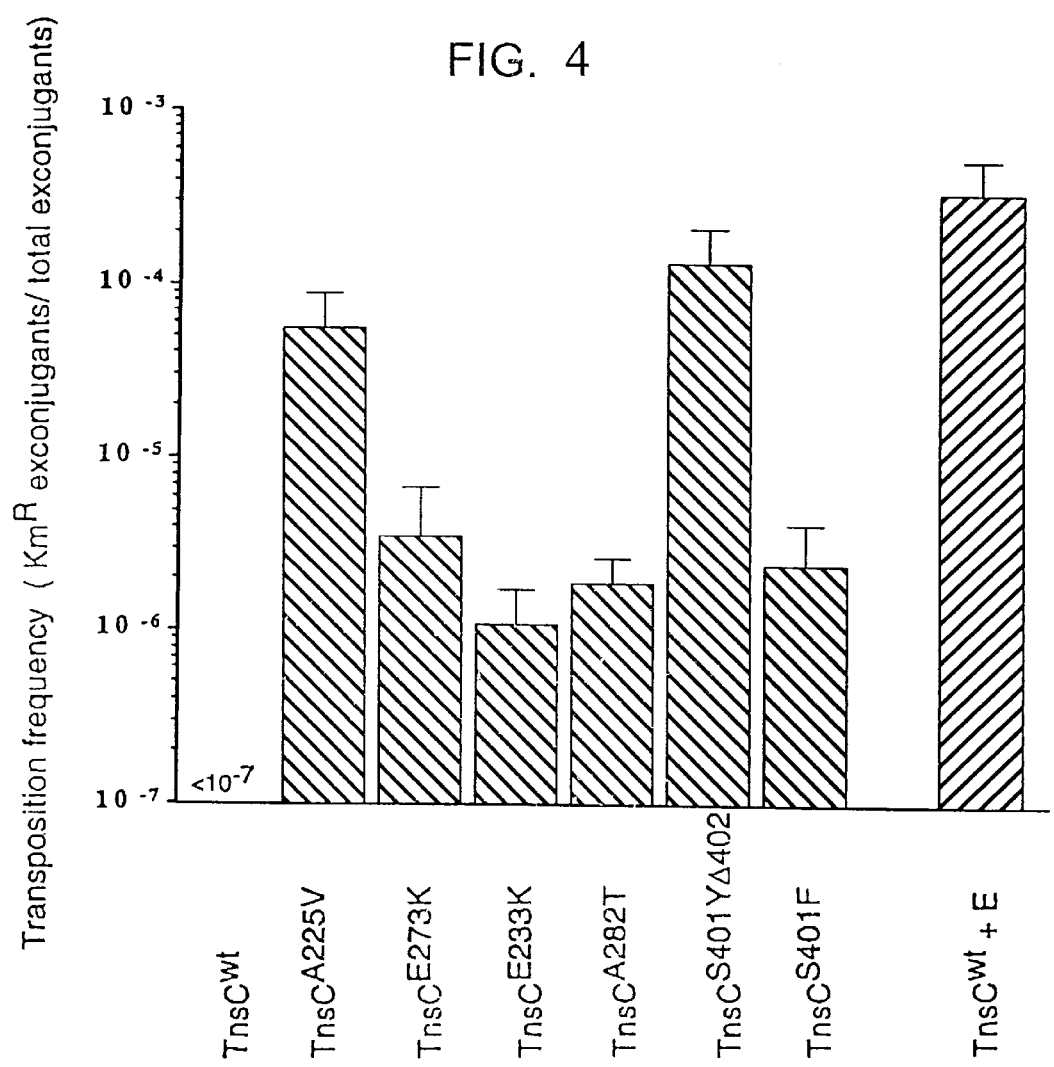
FIG. 4. TnsC mutants promote transposition to conjugable plasmids. Frequencies of transposition of miniTn$\underline{7}$-Km$^R$ from the chromosome to the conjugable target plasmid pOX-G were measured by the mating-out assay. TnsA+B was present in each strain; the TnsC species present is indicated below each column.

The mating-out assay was used to explore the ability of the TnsC mutants to promote translocations into a different type of target molecule. This assay measures the frequency of transposition of miniTn7-Km$^R$ from the chromosome to pOX-G, a conjugative derivative of the E. coli F factor. The TnsABC$^{wt}$+E machinery preferentially selects conjugable plasmids as targets for transposition, whereas the TnsABC$^{wt}$+D machinery does not recognize pOX-G unless it contains attTn7 sequences (ROGERS et al. 1986, WADDELL and CRAIG 1988, WOLKOW et al. 1996). The TnsC mutants could promote transposition to pOX-G (FIG. 4). Thus, the results demonstrate that the gain-of-function TnsC mutants can promote intermolecular transposition.

Effects of the target selection factors TnsD and TnsE: Frequencies of transposition of miniTn7-Km$^R$ from a lambda phage to the chromosome and/or pOX-G were measured in strains containing TnsA+B and the TnsC mutants, either alone or in combination with TnsD or TnsE. The preferred target for TnsE reactions, pOX-G, was introduced by conjugation into strains containing TnsC mutants or the TnsC mutants+TnsE. The distribution of miniTn7-Km$^R$ insertions between the chromosome and pOX-G was determined by mating the pOX-G plasmids from the Km$^R$ products of a lambda hop assay into the Km$^S$ strain CW51, and testing whether Km resistance was plasmid linked. No transposition was detected in strains containing TnsABC$^{wt}$ alone or TnsABC$^{E233K}$+TnsD.

Response to the target selectors TnsD and TnsE: TnsD and TnsE are required to activate the TnsABC$^{wt}$ machinery and to direct transposition into particular target DNAs (10) (11) (13) (14). The TnsABC$^{mutant}$ machineries, by definition, do not require the inputs of TnsD or TnsE. However, the inventor investigated whether TnsD or TnsE could influence the frequencies or distribution of transposition events promoted by the TnsC mutants.

The λ hop assay was used to evaluate the effects of TnsD and an available attTn7 site on transposition promoted by the TnsC mutants. All of the mutant reactions were responsive to TnsD+attTn7, but those responses varied widely. Reactions activated by TnsABC$^{A225V}$ and TnsABC$^{E273K}$ were strongly stimulated by TnsD+attTn7, promoting 500- and 5000-fold more transposition, respectively, in the presence of TnsD+attTn7 than with TnsABC$^{A225V}$ or TnsABC$^{E273K}$ alone. The remaining mutant reactions were less profoundly influenced by TnsD:TnsABC$^{S401F}$ reactions showed a moderate (50-fold) stimulation. Reactions activated by TnsC$^{E233K}$, TnsC$^{S401Y\Delta402}$ and TnsC$^{A282T}$ were somewhat inhibited in the presence of TnsD.

The effects of TnsE was also studied by the λ hop assay. In the absence of TnsE, the vast majority of the TnsABC-$^{mutant}$ transposition events were targeted to the chromosome. In the presence of TnsE, preferential insertion into pOX-G was observed with some of the TnsC mutants.

These differential responses suggest that the six TnsC mutants are not activating Tn7 transposition through a single mechanism. Instead, the mutants can be segregated into two classes, based on their ability to respond to TnsD and TnsE. Transposition activated by the Class I mutants—TnSC$^{A225V}$ and TnSC$^{E273K}$—can by stimulated by TnsD and targeted to pOX-G by TnsE. Transposition activated by the Class II mutants—TnsC$^{E233K}$, TnsC$^{A282T}$, TnsC$^{S401Y\Delta402}$ and TnsC$^{S401F}$—is not responsive to the positive effects of TnsD or TnsE or both. By these criteria, TnsCS$^{S401F}$ is proposed to be a member of Class II: although TnsC$^{S401F}$-activated reactions are somewhat stimulated by TnsD, the distribution of insertions in TnsCS$^{S401F}$-activated reactions is not affected by TnsE. The grouping of the TnsC mutants into these two classes is supported by the differential responses of the TnsABC$^{mutant}$ reactions to immune targets, as described below.

Discussion

Proteins involved in target evaluation: How is an appropriate target for Tn7 transposition identified? The inventor has hypothesized that TnsC may serve as a "connector" or "matchmaker", linking the transposase and the target DNA in a manner regulated by the ATP state of TnsC (23) (27). TnsC has the biochemical properties necessary for this connection: it can directly interact with target DNA (24) and with the TnsA+B transposase (A. STELLWAGEN and N. L. CRAIG, unpublished results). However, wild-type TnsC (SEQ ID NO:1) is not sufficient to activate transposition. Instead, Tn7 transposition is dependent on TnsD or TnsE to activate the TnsABC$^{wt}$ machinery and select a target site. TnsD is an attTn7 binding protein (23) which recruits TnsC to this target. The resulting TnsC-TnsD-attTn7 complex can then attract the transposase in vitro (23). The mechanism by which TnsE activates transposition is not yet known. TnsE might 3be 3preferentially localized to conjugating plasmids and subsequently recruit TnsC to those molecules, or TnsE might modify TnsC so that TnsC's binding activity is now directed to those targets. Alternatively, TnsE might modify the transposase directly, without proceeding through TnsC. The results suggest that TnsD and TnsE provide alternative inputs into TnsC, which in turn recruits the TnsA+B transposase to the target DNA.

The successful isolation of TnsC gain-of-function mutants reveals that the TnsABC machinery is capable of engaging target DNA and promoting insertions without TnsD or TnsE. However, the mutant reactions have not mimicked the abilities of TnsD or TnsE to direct transposition into particular targets: transposition activated by the TnsC mutants does not show the preferential insertion into conjugable plasmids seen with TnsE-activated reactions, nor the attTn7 specificity of TnsD-activated reactions. Therefore, TnsD and TnsE are essential to recognize these positive target signals.

TnsC appears to receive a variety of inputs—from TnsD, TnsE and from immune targets—which control its activity. The activity of TnsC can also be influenced by mutation. Six gain-of-function TnsC point mutants have been described in this work, which segregate into two classes. The fact that different classes of TnsC mutants with different transposition activities were recovered is consistent with the hypothesis that there are multiple routes to activating TnsC. The Class I mutants, TnsC$^{A225V}$ and TnsC$^{E273K}$, enable the TnsABC machinery to execute transposition without sacrificing its ability to respond to both positive and negative target signals. Both are substantial gain-of-function mutants, with TnsABC$^{A225V}$ promoting eight-fold more transposition to the chromosomes than TnsABC$^{wt}$+E (FIG. 3). Transposition activated by these Class I mutants can be profoundly stimulated by TnsD+attTn 7, or directed to conjugable plasmids by TnsE, as well as being able to discriminate between immune and non-immune targets. Thus, the gain-of-function phenotypes seen with the Class I mutants have been achieved while preserving the ability of these TnsCs to transduce information between the target DNA and the transposase.

The TnsC mutants which fall into the second class behave much more like constitutively activated versions of TnsC. Some of these mutants also promote considerable amounts of transposition: TnsABC$^{S401YA402}$ results in 50-fold more transposition to the chromosomes than TnsABC$^{wt}$+E (FIG. 3). However, the nature of the transposition reactions promoted by the Class II TnsC mutants is quite different than those seen with the Class I mutants. Immune and non-immune targets are used essentially equivalently in reactions with the Class II mutants, and TnsD and TnsE are not able to profoundly influence the frequency or distribution of these transposition events. A similar loss of responsiveness to target signals is seen when Tn7 transposition is activated by nonhydrolyzable ATP analogs in vitro. Transposition can still occur when TnsC's ATPase activity is blocked with AMP-PNP, but those transposition events no longer require TnsD and are no longer targeted to attTn7 (BAINTON et al. 1993). Instead, any DNA molecule, including immune targets, can serve as a target for Tn7 insertion. Thus, TnsABC transposition can be constitutively activated by AMP-PNP or by the Class II TnsC mutants. It is noteworthy that the amino acid affected in TnsC$^{E233K}$ lies in one of TnsC's ATP motifs.

Comparison to other elements: The use of an ATP-dependent protein such as TnsC to regulate target site selection is not unique to Tn7. Bacteriophage Mu transposition is also profoundly influenced by its ATP-utilizing protein MuB. MuB is an ATP-dependent DNA binding protein (57) (MAXWELL et al. 1987) which is required for efficient transposition in vivo (58) (59). In vitro, the MuA transposase preferentially directs insertions into targets that are bound by MuB (60) (61) (19). Although there is no particular sequence specificity to MuB binding, its distribution on DNA is not random: MuB binding to target molecules that already contain Mu sequences is specifically destabilized through an ATP-dependent mechanism (19). Therefore Mu, like Tn7, recognizes and avoids immune targets; moreover, MuB and TnsC$^{A225V}$ appear to play functionally similar roles in regulating transposition.

Mu and Tn7 belong to a family of transposons which encode proteins with ATP binding/hydrolysis motifs; other members include IS21 (35) (62), Tn552 (36), Tn5053 (33), and Tn5090 (34). Therefore, the strategy of using an ATP binding protein to regulate target site selection may extend to the entire family. Tn5053 is particularly interesting, since it encodes three proteins which are required for its transposition: a presumptive transposase containing a D, D(35)E motif characteristic of transposases and integrases, a potential regulatory protein containing Walker A and B motifs, and a third protein of unknown function (33). Tn5053 shows some degree of target site specificity, inserting predominantly into the par locus of the conjugable plasmid RP4. It is tantalizing to speculate that the third protein of Tn5053 is a target selector, like TnsD or TnsE, directing insertions into the par locus.

The inventor's work has illustrated the role of target DNA in controlling Tn7 transposition in vivo, and has strongly implicated TnsC as a central player in this regulation. Single amino acid changes in TnsC can disrupt the communication between the transposon and the target site, reducing the stringency of Tn7's target site selectivity. TnsD promotes Tn 7 insertion at high frequency into attTn7, a safe haven in the bacterial chromosome, whereas TnsE allows Tn7 access to conjugable plasmids, and thus a means to spread through bacterial populations. Avoidance of immune targets also promotes the spread of the element, rather than local hopping, and prevents one Tn7 element from inserting into another. TnsC may integrate all of these target signals, and communicate that information to the transposase.

TABLE 1

TnsC$^{A225V}$ promotes intermolecular transposition

| Tns functions | transposition frequency |
| --- | --- |
| TnsABC$^{wt}$ | <10$^{-7}$ |
| TnsABC$^{A225V}$ | 8.8 (±8.1) × 10$^{-6}$ |
| TnsABC$^{wt}$DE | 5.5 (±1.1) × 10$^{-4}$ |

Frequencies of transposition of miniTn7-Km$^R$ from a high copy plasmid to pOX-G were determined using the mating-out assay, and are expressed as the number of Km$^R$ exconjugants/total exconjugants. Each value is the average of three independent measurements.

Example 2

Materials and Methods

Media, Chemicals, and Enzymes

Luria broth (LB) and agar were prepared as described by (42). Carbenicillin and kanamycin selections were carried out at a concentration of 100 µg/ml. DNA modifying and restriction enzymes were purchased from commercial sources and used according to manufacturer's instructions. Taq polymerase was purchased from Boehringer Mannheim Biochemicals.

Bacterial Strains and Plasmids

Tn7 donor plasmids contain a miniTn7 element in which the minimal end sequences of Tn7 (Tn7L 1-166 and Tn7R 1-199) flank a selectable marker. A pBR plasmid containing a mTn7-kanamycin element with NotI and SpeI sites at the ends of the kanamycin cassette has been shown to be a an effective donor. When transposition products are to be recovered by transformation, it is useful to prevent transformation of unreacted donor. One strategy is to cut the donor backbone with a restriction enzyme that does not cut within the Tn7 element or within the target DNA. Another strategy is to use donor plasmids that will not replicate with the products recovered. One strategy is to make the replication of the donor depend on a protein that is not present in the transformation strain. For example, the mTn7 element can be placed on a plasmid which does not itself encode an initiator protein for replication. A particular example is to make the donor backbone an R6K plasmid that does not encode the replicator protein pir. The R6Kpir-miniTn7 plasmid can then be grown in a strain which contains pir (supplied for example by a heterologous plasmid) and the transposition mixture transformed into a strain lacking pir. With selection for the marker on the mTn7, only insertions into the target DNA will be recovered. Subcloning Efficiency DH5alpha competent cells were purchased from GIBCO BRL and used according to the manufacturer's instructions.

The target plasmid pRM2 (SEQ ID NO:6) contains bases −342 to +165 of attTn7 cloned into pUC18 [47]. The donor plasmid pEMA (SEQ ID NO:4) carries a miniTn7 element comprised of the 166 terminal bases of the left end of Tn7 and 199 bases of the right end flanking a gene conferring resistance to kanamycin [23].

Tns Proteins

The purification of TnsA and TnsB-His are described in (63). TnsA was stored in 25 mM Hepes (pH 8.0), 150 mM NaCl, 1 mM EDTA, 1 mM DTT, 5% glycerol at −80° C. TnsB was TnsB-His, a derivative containing a C-terminal polyhistidine tag, and was stored in 25 mM Hepes (pH 8.0), 500 mM KCl, 2 mM DTT, 1 mg/ml BSA, 25% glycerol at −80° C. The purification of TnsC and TnsC$^{A225V}$ is a modified procedure from (24) which is described in (25) (26). Both proteins were stored in 25 mM Hepes (pH 8.0), 1M NaCl, 2.5 mM DTT, 1 mM ATP, 10 mM MgCl$_2$, 0.1 mM EDTA, 10 mM CHAPS, 10% glycerol at −80° C. TnsD was TnsD-His (P. Sharpe and N. Craig, in preparation), a derivative containing a C-terminal polyhistidine tag, and was purified by Ni$^{+2}$ chromatography before being stored in 50 mM Tris (pH 7.5), 2 mM DTT, 500 mM KCl, 1 mM EDTA and 25% glycerol at −80° C.

Transposition Reactions in vitro

Transposition reactions are adapted from the standard in vitro reaction described in (23). Reaction mixtures, 100 µl in volume, contained (final concentration) 0.25 nM pEMA donor, 1.9 nM pRM2 target, 26 mM Hepes, 4.2 mM Tris (pH 7.6), 50 µg/ml BSA, 100 µg/ml yeast tRNA, 2 mM ATP (pH 7.0), 2.1 mM DTT, 0.05 mM EDTA, 0.2 mM MgCl$_2$, 0.2 mM CHAPS, 28 mM NaCl, 21 mM KCl, 1.35% glycerol, 60 ng TnsA, 25 ng TnsB, either 100 ng TnsC$^{wt}$, or 100 ng TnsC$^{A225V}$, and 40 ng TnsD, unless otherwise indicated, in a 30 minute preincubation at 30° C. (TnsA=19 nM, TnsB=3.1 nM, TnsC=16 nM, TnsD=6.5 nM). Magnesium acetate was added to a final concentration of 15 mM and the reactions were allowed to proceed for an additional 60 minutes at 30° C. Products were extracted with a 1:1 mixture of phenol/chloroform, ethanol-precipitated, and resuspended in water in preparation for subsequent analyses.

PCR Primers and Amplification

Oligonucleotides used for the various PCR amplifications to analyze the products of transposition are:

NLC95 (SEQ ID NO:7): (5')-ATAATCCTTAAAAACTCCATTTCCACCCCT-(3')

NLC209 (SEQ ID NO:8): (5')-GTGATTGCACCGATCTTCTACACCGTTCC-(3')

NLC429 (SEQ ID NO:9): (5')-TTTCACCGTCATCACCGAAACGCGCGAGAC-(3')

NLC430 (SEQ ID NO:10): (5')-AATGACTTGGTTGAGTACTCACCAGTCACA-(3')

NLC431 (SEQ ID NO:11): (5')-ATGAACGAAATAGACAGATCGCTGAGATAG-(3')

NLC432 (SEQ ID NO:12): (5')-CAAGACGATAGTTACCGGATAAGGCGCAGC-(3')

Two percent of the 100 µl transposition reaction was used as the template in a given PCR amplification. 100 pg of plasmid pMCB20 was used when amplifying a marker product for size comparison on the high resolution denaturing gels. 30 temperature cycles of 94° C. for 1.0 minute, 55° C. for 1.5 minutes, and 72° C. for 1.5 minutes were run for all amplifications, followed by a single 5 minute incubation at 72° C. The buffer composition and quantity of Taq polymerase recommended by the manufacturer (Boehringer Mannheim Biochemicals) were used for all reactions. PCR products were ethanol-precipitated, resuspended in water, and loaded on a high resolution denaturing gel.

Probe Labelling

Oligonucleotide probes were 5' end-labelled with [gamma-$^{32}$P] ATP substrate and bacteriophage T4 polynucleotide kinase for 45 minutes at 37° C. Labelled probes were separated from unincorporated label by size exclusion through a G50 Nick Spin Column (Pharmacia).

High Resolution Denaturing Gels

The resuspended PCR products were electrophoresed on either a 5% or 6% polyacrylamide denaturing gel and electrotransferred to Gene Screen Plus membrane (du Pont). The resulting blots were visualized by hybridization with an appropriate oligonucleotide probe at 50° C. and exposed overnight to phosphorimager screens (Molecular Dynamics), which were scanned the following day.

Results

TnsC$^{A225V}$ Supports Efficient Transposition in vitro

Figure 5:
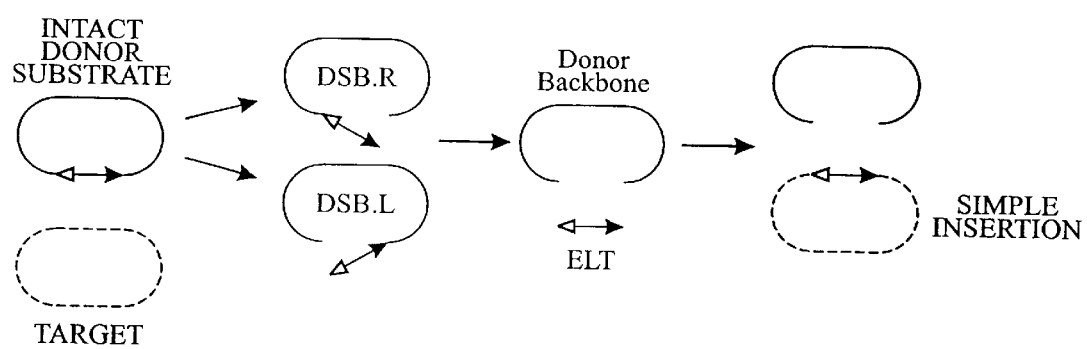
FIG. 5. The substrates, intermediates and products of Tn$\underline{7}$ transposition. One substrate is a donor plasmid containing a miniTn$\underline{7}$ element which contains the essential cis-acting sequences at each end for transposition. The other substrate is a target plasmid. Transposition initiates with a double strand break at either end of the element, followed by a second break at the other end to generate an excised linear transposon. This excised transposon is then joined to the target DNA to form a simple insertion.

A diagram of Tn7 transposition is shown in FIG. 5. Tn7 mobilizes via a cut-and-paste mechanism, whereby both ends of the element are first excised from the donor backbone by double-strand breaks, and join to the target DNA most likely via transesterification reactions to form simple insertions with short gaps at either end. Other possible intermediates of a transposition reaction are double-strand breaks (DSBs), where one end of the transposon has been excised but the other end remains attached to the donor backbone, excised linear transposons (ELTs), where both ends have been excised from the donor and neither end has joined to the target, and double-strand break, single-end joins (DSB-SEJs), where one transposon end has been broken in the donor and joined to the target molecule.

Figure 6:
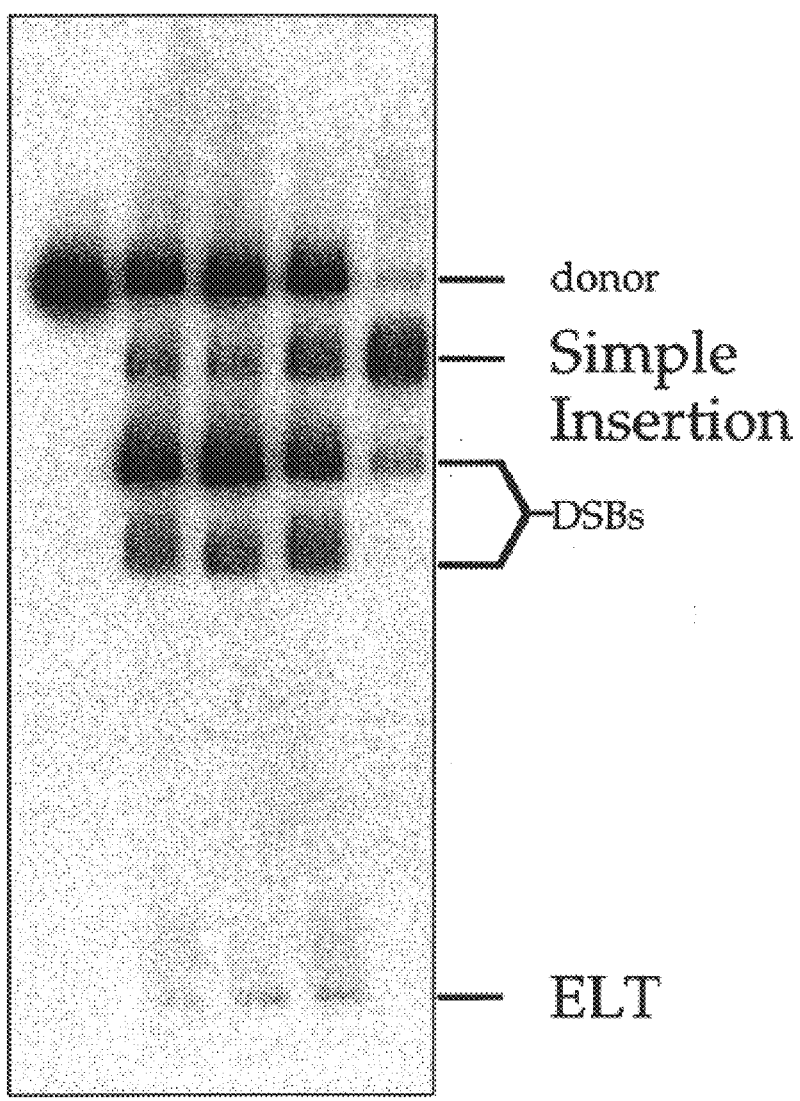
FIG. 6. Analysis of Tn$\underline{7}$ transposition reactions on a agarose gel. The donor plasmid, a pBR derivative, contained a miniTn$\underline{7}$ element containing a kanamycin gene and the target plasmid contained an attTn$\underline{7}$ site. Recombination reactions were carried out as described, the DNAs isolated from the reaction mixture by phenol extraction, digested with a restriction enzyme that cuts once in the donor backbones, displayed by electrophoresis on an agarose gel, transferred to a membrane by electrotransfer and hybridized with a probe specific for the miniTn$\underline{7}$ element. Lane 1: TnsA+B; Lane 2: TnsA+B+Cwt; Lane 3: TnsA+B+CE233K; Lane 4: TnsA+B+CS$^{401YA402}$, Lane 5: Tns(A+B)+C$^{A225V}$.

The Tn7 transposition reaction has been reconstituted in vitro, in which purified Tns proteins promote the transposition of a mini Tn7 element from a donor plasmid into an attTn7-containing target plasmid (Bainton 1993). TnsABC$^{wt}$+D supports this reaction with great efficiency. In the absence of TnsD, TnsABC$^{wt}$ does not generate a detectable level of insertion products (FIG. 6, lane 2) although double-strand break intermediates are seen upon prolonged incubation. By contrast, reactions containing TnsABC$^{A225V}$ show a dramatic accumulation of simple insertions, at efficiencies that approach TnsABC$^{wt}$+D reactions (FIG. 6, lane 5). Neither the TnsABC$^{A225V}$ nor the TnsABC$^{wt}$+D reactions generate visible levels of DSB-SEJ products, indicating that the vast majority of Tn7 transposition events result in the complete (i.e., two-ended) insertion of the transposon into the target DNA, rather than a single-ended insertion event.

TnsABC+D transposition is not only efficient, it is also very target site-specific. TnsABC+D insertions occur almost exclusively into the attTn7 site present on the target plasmid (Bainton, et al., 1993, data not shown). By contrast, the TnsABC$^{A225V}$ insertions are not limited to the attTn7 site. Alternative restriction analysis of the TnsABC$^{A225V}$ reaction yields a smear of products on an agarose gel (data not shown), suggestive of a population of insertions located at many different positions in the target plasmid. To investigate the distribution of these insertions, we subjected the TnsABC$^{A225V}$ reaction products to high-resolution analysis, as described below.

Distribution of TnsABC$^{A225V}$-Mediated Insertions is Highly Nonspecific

A PCR-based approach has been used to analyze insertional mutations in SV40 and yeast TRP1ARS1 minichromosomes [30, 31], and perform functional analyses of insertional mutations in yeast chromosome V and the *E. coli* supF gene [Smith, 1996 #427] and [32], respectively.

Figure 7:
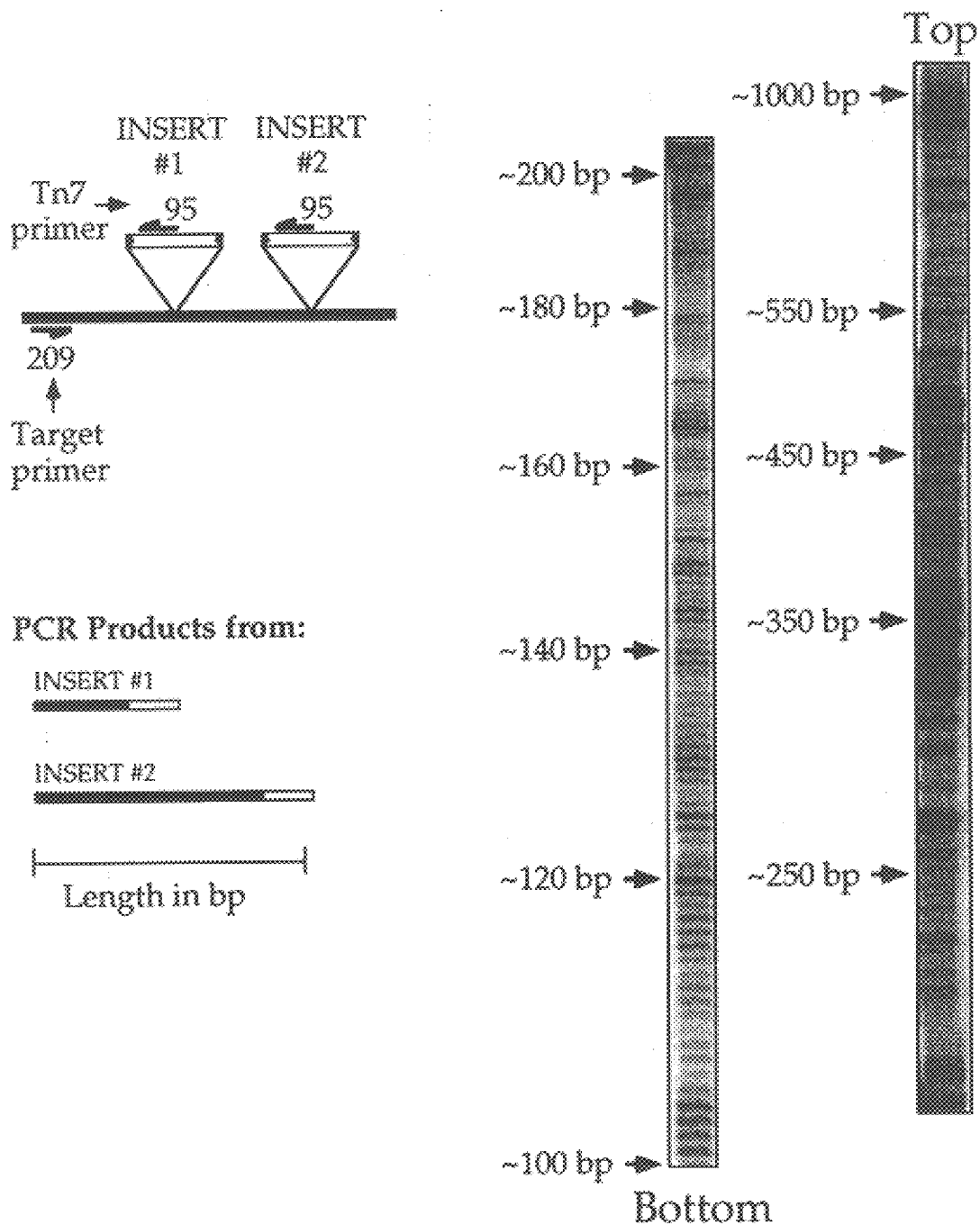
FIG. 7. Tn$\underline{7}$ insertion mediated by TnsA+B+C$^{A225V}$ occurs at many different sites in a target DNA. In vitro transposition reactions using TnsA+B+C$^{A225V}$ were carried out and the DNAs isolated by phenol extraction and ethanol precipitation. A PCR reaction using the transposition products as a template was then carried out in which one primer (NLC 209) (SEQ ID NO:8) complementary to a sequence on the target DNA and another primer NLC 95 (SEQ ID NO:7) complementary to the left end of Tn$\underline{7}$. The length of the PCR products will vary depending on the position of the Tn$\underline{7}$ insertion, for example, insertions being closer to the target primer will be short (insert 1) and those more distant will be longer (insert 2). The products of the in vitro reaction were then displayed on a denaturing acrylamide gel by electrophoresis, transferred from the gel to membranes and analyzed by hybridization to a radioactively labeled probe that hybridizes to Tn$\underline{7}$ sequences on one end of the transposon.

PCR was utilized to survey the distribution of TnsABC$^{A225V}$ insertions previously seen on the agarose gel at higher resolution. The diagram in FIG. 7 illustrates the PCR strategy used to amplify the population of insertion products present in a TnsABC$^{A225V}$ reaction, with two representative insertions being shown as examples. One PCR primer (NLC95)(SEQ ID NO:7) hybridizes within the cis-acting end sequence of the inserted element and the other (NLC209)(SEQ ID NO:8) hybridizes to an arbitrary position in the target molecule. Thus, the length of the PCR product reflects the positions of the insertions into the target molecule.

Amplification of a pool of insertions generated a smear of reaction products when displayed on an agarose gel, as expected (data not shown). The PCR products were run on a 6% polyacrylamide denaturing gel to achieve single nucleotide resolution and visualized by Southern blotting and hybridization with a Tn7-specific probe (FIG. 7). The striking result is that the distribution of products is remarkably nonspecific. Insertions have occurred at nearly every base within the highly resolved lower portion of the gel. PCR products of more than roughly 200 bp in length are resolved poorly. Some areas of dense signal are seen in this region, potentially indicating preferential points of insertion. However, compression of bands could also account for the apparently singular products; analysis of these insertion products with other primer pairs supports this latter possibility (see below).

This confirms the inventor's hypothesis that the TnsABC$^{A225V}$ machinery is capable of directing Tn7 transposition into the target plasmid with high efficiency and low specificity.

Surveillance of the Entire Target Plasmid

Figure 8:
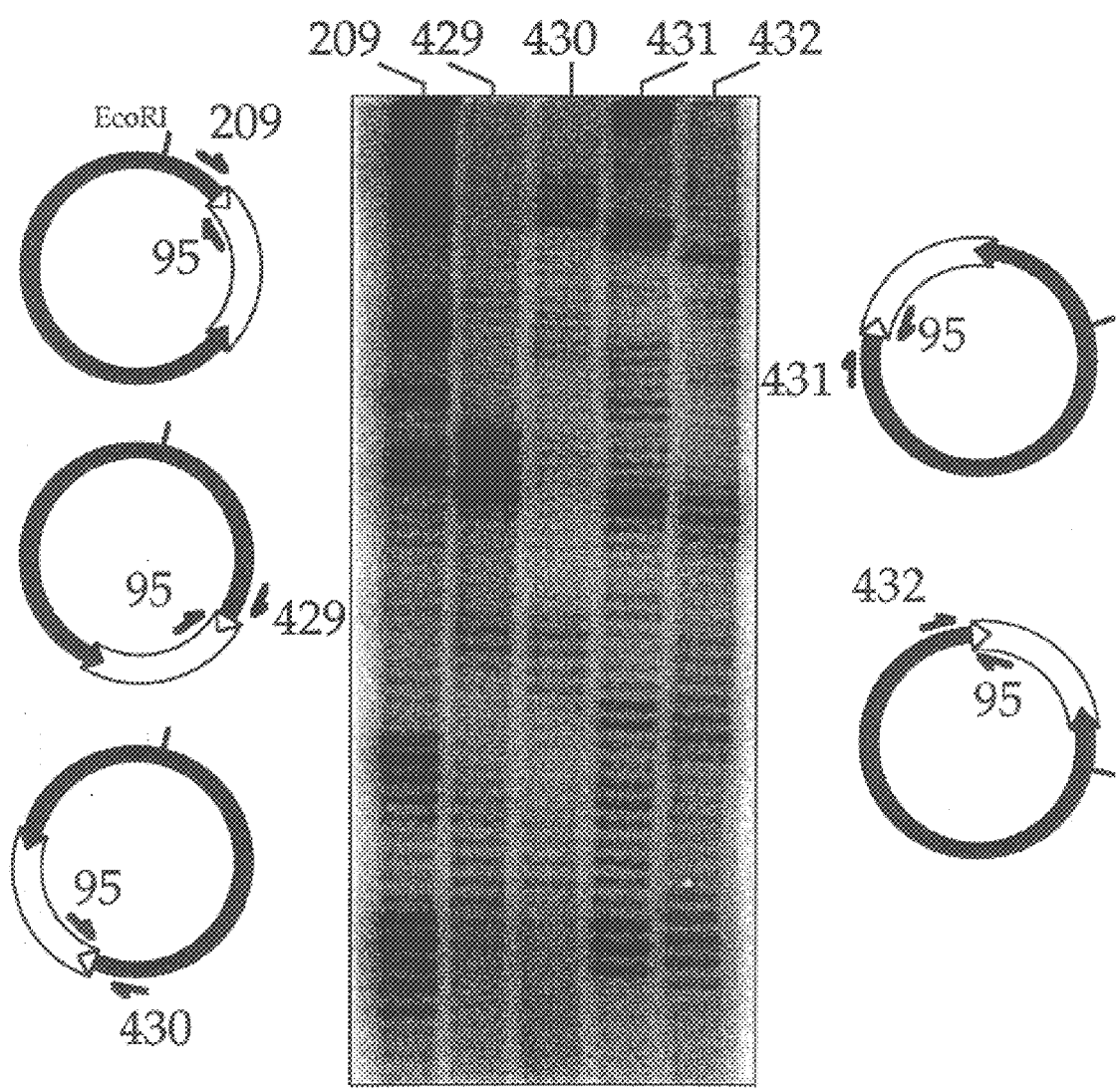
FIG. 8. Analysis of distribution of insertions in different regions of the plasmid. Tn$\underline{7}$ displays little target site selectivity at many regions of a target. In vitro transposition reactions were carried out and the products used as a template for PCR reactions as described above except for the target primer. In these experiments, one primer in the end of Tn$\underline{7}$ (NLC 95) (SEQ ID NO:7) was used and in separate reactions primers from several different positions in the target DNA were used.

In the experiments above, the focus was on a relatively short region of the target plasmid pRM2 (SEQ ID NO:6). It was demonstrated that TnsABC$^{A225V}$ can direct insertions into virtually every base pair of this region. To be certain that the phenomenon is not specific to the region of the plasmid, a family of primers was synthesized, each of which paired with a Tn7 end-specific primer to allow amplification of all regions of pRM2 (SEQ NO:6). These primers are spaced at approximately 500 bp intervals around the target plasmid and will amplify insertions in predominantly one orientation. FIG. 8 diagrams the amplicons for each primer pair and shows a denaturing gel Southern blot of the resulting PCR products. The results indicate that the C$^{A225V}$-mediated insertions do occur into positions all around the target plasmid. As was seen for the original amplicon analyzed, there is considerable variability in the strength of the signal for individual points of insertion, but insertions do occur at some level at every position. Thus, the TnsABC$^{A225V}$ machinery does not appear to have a specificity for any particular region of this target plasmid.

In another approach to investigating the possible sequence specificity of TnsABC$^{A225V}$ target site selection, 67 independent insertions into a 12 kb plasmid were collected and analyzed. TnsABC$^{A225V}$ transposition reactions using a target plasmid containing several *E. coli* genes were transformed into *E. coli* to select kanamycin-resistant colonies. The target plasmids were then recovered and sequenced to determine the position of each insertion. 62 out of the 63 insertions were located in different positions on the target plasmid. A comparison of the sequences of these insertions supported our previous observations that there is very little sequence specificity governing the selection of TnsABC$^{A225V}$ target sites. Attempts to derive a consensus sequence for the 5 bp target site duplication sequence revealed a faint preference for NYNRN (SEQ NO:14), but the bias is not very compelling.

Exploiting the TnsABC$^{A225V}$ Machinery for in vitro Mutagenesis

The high efficiency and low target specificity of the TnsABC$^{A225V}$ transposition reaction makes this a useful system for mutagenizing a variety of DNA targets. Insertional mutagenesis could be performed on cosmid libraries, cDNA libraries, PCR products, BACs, YACs, and genomic DNAs, among others. The inventor has mutagenized pUC-based plasmids, cosmids, BACs ranging in size from 5 to 120 Kb (data not shown), and *H. influenzae* genomic DNA (Gwinn et al., 1997). In fact, the inventor has not encountered DNA that cannot serve as a target for TnsABC$^{A225V}$ transposition.

Once DNA targets have been successfully mutagenized in vitro, the simple insertions will be recovered. For a simple insertion product to become a stable replicon, the 5' nonhomologous overhangs trailing off both ends of the inserted transposon must be removed, the gaps filled in, and the strands ligated. A simple method to perform such processing functions is to transform the pool of transposition products into a host and rely on the host's repair machinery, selecting for a transposon-borne marker. In *E. coli*, the 5' single-stranded overhangs and gaps on either end of the transposon after a simple insertion are readily repaired by the host (see below). The donor plasmid for other hosts could be customized in a number of ways to best facilitate the recovery of the desired insertional mutants.

The inventor recovered simple insertions into pRM2 in *E. coli*, since Tn7 insertions can be easily repaired in this host.

Simply transforming transposition reactions into host cells as a method to recover simple insertion isolates presents a background contributed by donor molecules that have not undergone transposition and thus continue to carry the selectable marker on a stable replicon. In order to eliminate the background false positives that can complicate a screen for insertional mutants, the ability of the unreacted donor to transform cells can be reduced. Two methods have been provided: 1) destruction of the donor plasmid's ability to replicate by restriction digestion prior to the transposition reaction, and 2) use of a conditional replicon origin in the donor backbone which renders the donor incapable of replication in the cells being ultimately transformed with the transposition pool.

For the first method, 5 identical TnsABC$^{A225V}$ reactions were carried out on linearized pMCB31 donor DNA paired with cosmid clone ES#3 target DNA, an approximately 50 kb replicon which contains an insert of genomic DNA from *E. tarda*. Linearizing the plasmid will prevent the donor plasmid from replicating once transformed into the host. The products were pooled for the extraction and precipitation steps, and then a portion of the resultant sample was transformed into BRL Subcloning Efficiency DH5-alpha competent cells. Assuming a 10% loss in the recovery of the DNA after the transposition reaction, the efficiency of transformation relative to $\mu$g of input donor DNA was approximately $3.8 \times 10^4$ colonies/$\mu$g/ml of cells. One-tenth of a microgram of donor DNA is typically used in a reaction, so by extension, if all of the product DNA from a single transposition reaction is transformed, 3800 colonies could be isolated, an efficient mutagenesis. The DH5$^{alpha}$ cells are advertised to have a transformation efficiency of equal to or greater than 1×10$^7$ colonies/μg supercoiled pUC19/ml of cells. Simply using higher efficiency cells or electroporation cells should yield considerably higher numbers of isolates from a single transposition reaction, and probably aid in picking up rarer events.

Another method employs a heterologous origin of replication on the donor plasmid, for example, R6K. Replicons relying on this origin must be maintained in a host carrying a resident copy of the pir gene, which codes for the π protein, a necessary component for initiation of replication at R6K$_{gamma}$ origins. Thus, it is simple to eliminate false positives stemming from unreacted donor molecules simply by transforming the transposition products into pir$^-$ cells, and relying on the competent origin of replication in the target molecule for recovery of simple insertion isolates. Transposition reactions employing this donor were prepared for transformation as described above.

It is conceivable that the larger plasmid (~50 kb) would be more difficult to transform after receiving an insertion because it would be a large open circular molecule approximately 10 times the size of the pRM2 (3.2 Kb) open circle with an insertion. To gain insight into the possibility of target size limitations using the transformation method of simple insertion recovery, transpositions of the miniTn7 element from pMCB40 into the two target plasmids were directly compared. The transformation efficiencies of the two reactions were very similar. The different targets were included at comparable concentrations in the transposition reactions, but were not equimolor. The results suggest that ES#3 simple insertions can transform the cells at nearly the same efficiency as the smaller pRM2 simple insertions. It is difficult to test reaction conditions under which the cosmid target is available at the same molarity as the pRM2 target because elevated levels of total DNA in the reactions can compromise the reproducibility with which DNA is recovered after transposition.

The high transformation efficiencies demonstrate the utility of this reaction for a mutagenesis in which the simple insertion products can be stably replicated in an *E. coli* host. This same type of protocol could be used in other bacterial species and strains with development of the appropriate DNA substrates.

Discussion

TnsC$^{A225V}$ circumvents the requirement for a targeting protein.

Tn7 demonstrates considerable diversity when it comes to target site selection. It has a sophisticated system for choosing either a highly conserved "safe haven" in the *E. coli* chromosome (attTn7) or somewhat random sites throughout a cell's genome or resident conjugable plasmid, mediating these different selections via alternative targeting proteins encoded by the element. In this way, Tn7 is significantly different than all other well-characterized transposable elements, whose target site selections are mediated predominantly by either the transposable alone (e.g., IS10/Tn10) or in conjunction with one other accessory protein (bacteriophage Mu). IS10/Tn10 selects a target site via a direct interaction of the Tn10 transposase with the target DNA. It has been demonstrated that particular mutations in the Tn10 transposase are capable of altering target recognition features while leaving other functions of the transposase unaffected (65). The bacteriophage Mu, however, encodes a transposase, MuA, and an ATP-dependent activator of MuA, MuB. MuB functions as an accessory protein that, when complexed with target DNA, attracts the MuA transposase to the site of insertion. It is likely that having more proteins involved has allowed Tn7 to be more adaptive to environmental changes when choosing its new sites of residence, and ensured its survival by enabling it to employ a more tailored approach to disseminating itself amongst various cell populations.

This example has focused on the role of TnsC in the selection of a target site. As discussed, TnsC has been implicated as the major communicator between the TnsAB transposase bound to donor DNA, and the TnsD or TnsE targeting proteins, complexed with target DNA. Experiments have shown that TnsC does have the capacity to bind DNA nonspecifically in the absence of TnsD and TnsE (ref) but attempts to isolate simple insertions in vivo and in vitro in the absence of the targeting proteins proved unsuccessful with wild-type TnsC (23). Isolation of the TnsC$^{A225V}$ mutant, however, has permitted the inventor to circumvent this requirement and isolate simple insertions from reactions lacking TnsD and TnsE. Not only does the mutant facilitate the recovery of simple insertions, it does so very efficiently.

Ability of TnSC$^{A225V}$ to Insert Nonspecifically

It is clear that TnsC$^{A225V}$ has a considerable gain of function over wildtype TnsC, as evidenced by the increased yield of simple insertions in a standard in vitro reaction (25) (26) (this example). A more detailed evaluation was necessary to determine the actual sites of insertion because restriction digests of the product pools indicated that there is extensive variability in site selection relative to TnsD-mediated insertions, which are targeted almost exclusively to the attachment site. PCR amplification of pools of transposition products followed by high resolution denaturing gel analysis of several independent reactions has revealed that the insertions into the pRM2 target plasmid are detectable at every base visible within the well-resolved portions of the gels. Although the target site selection is not completely random (there are differences in band intensities), one possibility is that the nonspecific DNA binding activity of TnsC has been enhanced in the TnsC$^{A225V}$ mutant, giving the protein the capacity to direct the TnsAB transposase to the wide variety of insertion sites observed.

It is possible that the TnsC$^{A225V}$ mutation has altered TnsC in such a way that it simulates a TnsC-TnsE complex, capable of insertions at more random sites. Perhaps the role of TnsE is to strengthen TnsC's noonspecific interaction with the target DNA, thereby promoting insertions into sites where TnsC and TnsE happen to complex. The ability of TnsE to preferentially direct transposition to conjugating plasmids (14) holds true when TnsC$^{A225V}$ is substituted for wild-type TnsC (SEQ ID NOS:1 and 2) (25) (26). This suggests that this mutation in TnsC does not compensate for all specific activities of a targeting protein. The TnsABC$^{A225V}$ reaction is also sensitive to the presence of the target site specific protein TnsD, as evidenced by a detectable increase in the frequency of insertions when TnsD is present.

These observations may explain why Tn7 has chosen to preserve a more complicated target site selection mechanism. In a cell containing only wildtype proteins, an extra layer of regulation can be exercised when two proteins complex to direct insertions, and the result may be less deleterious to cell populations than the somewhat rampant levels of insertions observed in reactions with the TnsC$^{A225V}$ in the absence of targeting proteins. Occurrence of a mutation like TnsC$^{A225V}$ in nature would decrease the specificity and increase the frequency of insertions, the consequence of which could quite possibly be more insertions into essential genes.

It is conceivable that TnsC has always played the primary role in directing the TnsAB transposase to insert, and the targeting proteins are more accessory. The inventor has envisioned TnsD binding DNA near the attachment site, and TnsC acting as an activation bridge to the transposase, but an alternative view is that the ability of TnsC to bind DNA plays a more central role in directing the donor complex to an insertion site, and TnsD has the role of "steering" a TnsAB+TnsC complex to a particular point of insertion. The A225V point mutation could confer the ability for TnsC to "steer" the donor complex to insert without the aid of a target-binding protein.

There is No Apparent Sequence Preference at the Point of Insertion

Two main approaches have been taken herein to analyze the TnsC$^{A225V}$-mediated insertions at nucleotide resolution. The first involves scanning along a short segment of DNA using PCR and high resolution denaturing gel analysis, quantitating specific signals at each base in a processive manner, and attempting to flush out a sequence motif common to those with the highest signals or lowest signals. The second method focuses on the recovery of the more frequent insertions only, those that can be recovered by simply transforming the transposition products, and relying on the host to conduct a successful repair of the replicons. These two methods provide different views of a common process. Since recovery of specific insertions is reliant of the process of transformation, rare insertion events that can be visualized by the PCR/denaturing gel method will most likely be severely underrepresented in a population of recovered transformants, if we assume that a higher concentration of a specific template will give rise to a diagnostic PCR product of higher intensity. This should bias the representative data accumulated from transposition product transformations to overlap with the subset of PCR products analyzed by denaturing gel analysis with the highest band intensities. In this way, both types of data are valid for attempting to determine a preferred insertion site.

The inventor's search for a common insertion site motif failed to uncover any preferred single nucleotides or groups of nucleotides that showed a higher incidence amongst the most intense signals on a denaturing gel or amongst the insertions isolated by transformation. Similarly, there were no apparent motifs common amongst the least preferred sites analyzed in the denaturing gel analysis. The lack of a sequence preference for insertions with this reaction is a very desirable result if it is to be employed as a highly nonspecific method for mutagenizing DNAs.

TnsC$^{A225V}$: A Tool for in vitro Mutagenesis

The impressive efficiency and low specificity of the TnsABC$^{A225V}$ in vitro reaction makes the reaction an excellent tool for in vitro mutagenesis. The high efficiency of the reaction (i.e., the high percentage conversion of donor substrate to double-ended simple insertions) is critical when considering how the recombinant DNAs will be recovered. The observation that the majority of the molecules resulting from a reaction that contain a junction between the donor DNA and the target DNA are double-ended simple insertions provides an advantage over alternative transposon-based insertional mutagenesis systems because large portions of the junctions seen in these reactions can be single-end joins (Rowland, S. J. et al. *EMBOJ* 14:196–205 (1995)). This study has demonstrated that standard commercially available *E. coli* competent cells are capable of repairing the characteristic gapped molecules formed as a result of a Tn7 simple insertion, provided the target DNA contains an origin capable of replicating in *E. coli*. Thousands of isolates can be recovered from a single transposition reaction starting with sub-microgram quantities of donor and target DNA. High efficiency cells should yield even greater numbers of isolates. Tn7 insertional mutants could be recovered from many different organisms as long as the target DNA carries information required to replicate in its respective host, the gaps can be repaired by the host, and DNAs can be reintroduced into the host with reasonable efficiency.

Cosmid clones have been successfully mutagenized and recovered by the method just described. Pilot reactions were done using purified cosmid clones. But it would be very simple to mutagenize an entire cosmid library and select for mutants by the same process. Replicons as large as 125 kb (a BAC, data not shown) have been successfully targeted and recovered. An earlier study of the inventor demonstrated that the ability of transposition machinery to recognize whether or not a potential target molecule already contains an insertion breaks down as the distance between two insertion sites increases (52). It has been shown that the degree to which a target molecule is "immune" to a second insertion has an inverse relationship to the length of separation of the sites of insertion. TnsC$^{A225V}$ has demonstrated a sensitivity to immunity signals. To date, the inventor has seen very few examples of double insertions into plasmids in the 40–50 kb range, suggesting that this tool will be highly effective for mutagenizing cosmids or plasmids in the 1–50 kb range.

Example 3

A Kit for Making Transposon Insertions

The kit provides transposon insertions into DNA in vitro. These insertions can be used to provide priming sites for DNA sequence determination, or to provide mutations suitable for genetic analysis, or both.

Section A: Reaction Constituents

A1) PROTEINS

TnsA 30 µg/ml in 10% glycerol
TnsB 20 µg/ml in 25% glycerol
TnsC$_{127}$100 µg/ml in 10% glycerol
Proteins were kept at −70° C.

A2) BUFFER CONSTITUENTS

| HEPES | 0.25 M pH 8.1 |
|---|---|
| Tris[Cl] | 0.25 M pH 7.6 [can be omitted] |
| BSA | 10 mg/ml |
| tRNA | 50 µg/ml [can be omitted] |
| DTT | 1 M |
| ATP | 100 mM |
| MgAcetate | 375 mM |

A3) TRANSPOSON DONOR PLASMID

100 µg/ml

The essential features of the plasmid are described above as containing the R6K conditional replicon.

A4) CONTROL TARGET PLASMID pLITMUS28 400 µg/ml

Figure 10B:
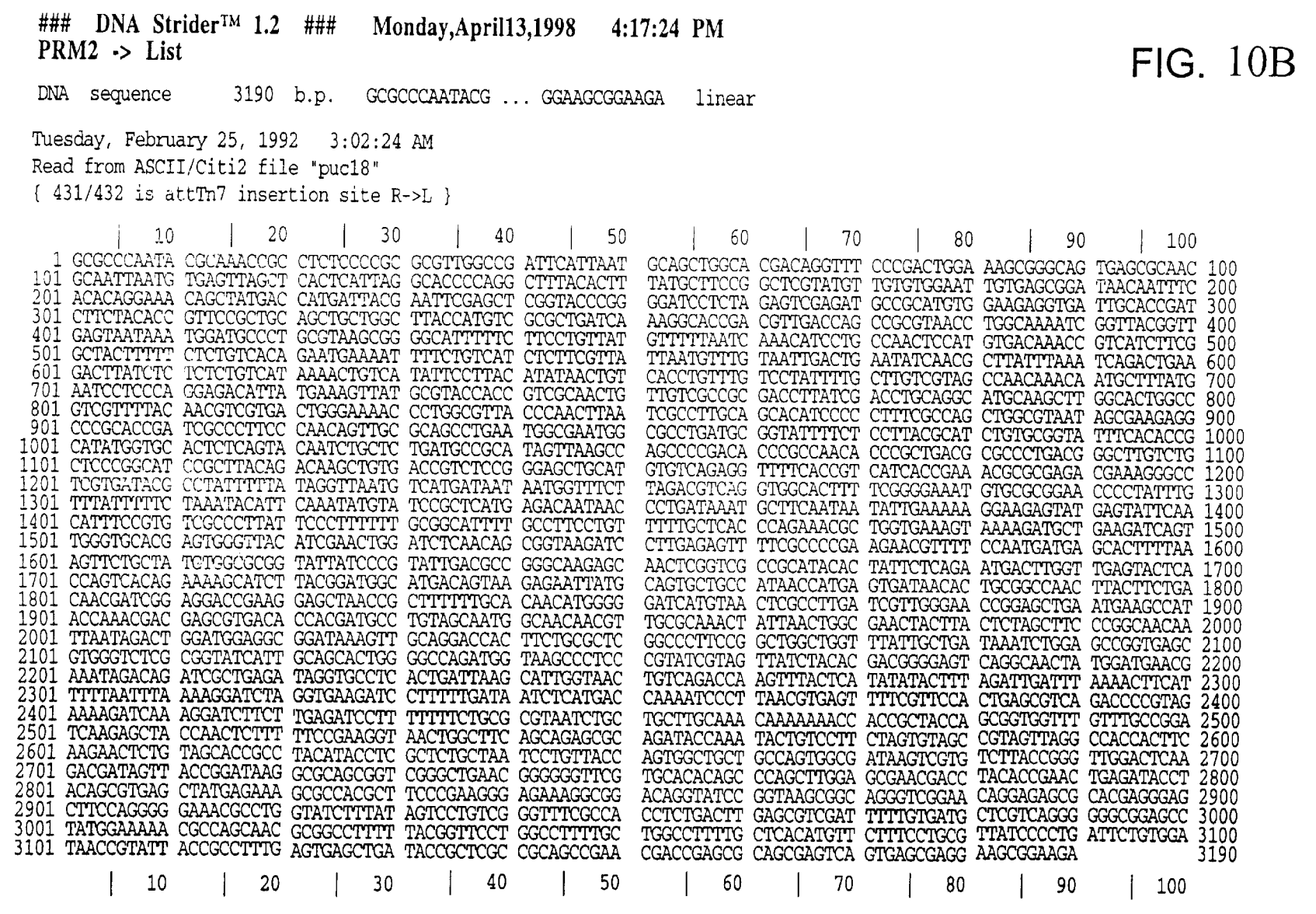

This plasmid contains both pUc and Mi3 origins, a lacZ' MCS and amp. See the Figure legend for FIG. 10B.

(New England BioLabs, 32 Tozer Road, Beverly, Mass., 01915)

A5) SEQUENCING PRIMERS

| | |
|---|---|
| NLC94 (SEQ ID NO: 13) | 3 pmol/µl |
| NLC95 (SEQ ID NO: 7) | 3 pmol/µl |

Section B: (Can be supplied by user)
B 1) FOR THE REACTION in vitro
  water; Millicue or equivalent recommended
  Target DNA not carrying Kanamycin resistance (0.4–0.5 µg per reaction)
  Water bath or heat block, 30° C.
  1.5 ml microtubes or other vessel; one per reaction.
B2) FOR STOPPING THE REACTION
  when using chemically competent cells
  Water bath or heat block, 75° C. Note: not 65° C.
when using electocompetent cells
  Distilled phenol equilibrated with TE or Tris pH 8.0
  Chloroform equilibrated with TE or Tris pH 8.0
  EtOH for precipitation
  NaAcetate 3 M
  Water or 1 mM Tris pH 8 or TE
B3) FOR RECOVERING INSERTIONS:
  B3a) Transformable cells:
    Any standard E. coli strain can be used; we have used ER1821, ER2502 and MC1061 (New England BioLabs, 32 Tozer Road, Beverly, Mass., 01915).
  Any kanamycin-sensitive organism in which npt can be expressed can also be used with the KanR donor, including but not limited to, Salmonella, other enteric organisms, Haemophilus, Rhizobium, and Bacillus. With a suitably altered selectable marker on the transposon donor plasmid, any prokaryotic or eukaryotic organism into which exogenous DNA can be introduced, may be used to recover insertions.
  In this example,
    B3ai) Chemically competent ER1821 New England BioLabs, 32 Tozer Road, Beverly, Mass., 01915 ($2 \times 10^7$ transformants/µg of LITMUS or similar plasmid) was used. A sample protocol for preparing these is provided below, section D1
    In example 2 we show the use of
    B3aii) Electrocompetent MC1061 (ATCC# 53338) ($7 \times 10^9$ transformants/µg of pLITMUS-28 or similar plasmid). A sample protocol for preparing these is provided below, section D2
    Commercially available competent or electrocompetent cells may also be used. The method of determining competence of these preparations is provided below, section D3.
  B3b) Outgrowth media:
    Rich Broth (D4a below) or mSOC (D4d) without drug, or equivalent.
      0.4 ml per reaction; we recommend three reactions as a standard pilot experiment (see Section C below).
  B3c) Selective media:
    Rich Agar with drug (D4b), or equivalent
      at least 1 plate per reaction; the standard pilot experiment described in section C require 6 plates, three with two drugs and three with one drug.
      Kanamycin is REQUIRED to select for the transposon of the present example
      Ampicillin is used for the RECOMMENDED positive control.
      Carbenicillin can be substituted
    For the example of Section C, below, RB Kan Amp (3 plates) and RB Amp only (3 plates) are used. If the target plasmid carries some other drug resistance, the experimental reaction in the pilot experiment should be plated on Kanamycin plus that drug.
B4) FOR DNA PREPARATION FOR SEQUENCING (see example 2):
  Any standard procedure that ordinarily gives sequencing grade DNA. We have tested Qiagen spin columns and gravity flow plasmid preparations.

Section C. Tn7 in vitro transposition reaction protocol

C1. REACTION VOLUME=100 µl
C2. RECOMMENDED PILOT EXPERIMENT 3 samples to be carried through.

| | |
|---|---|
| Tube 1 | Experimental (Target DNA, protein and donor plasmid added) |
| Tube 2 | Reaction positive control (pLITMUS28, protein and donor plasmid added) |
| Tube 3 | Reaction negative control (Target DNA added, no protein, donor added) |
| Tube 2 | is also used as a transformation positive control |

In this example, all tubes have pLITMUS28 as target (tubes 1 and 2 are duplicates). Tube 2 need not necessarily be included in every experiment.
C3. MAKE UP a mix using reagents of Section A:
  per reaction:
  (73.9 µl $H_2O$)–(volume of target DNA); in this example, target DNA is 1 µl

| | |
|---|---|
| 10 µl | Hepes (250 mM pH 8.1) |
| 1 µl | Tris (250 mM pH 7.6) |
| 0.5 µl | BSA (10 mg/ml) |
| 2.1 µl | tRNA (50 µg/ml) |
| 0.2 µl | DTT(1M) |
| 2 µl | ATP(100 mM) |

C4. DISPENSE mix of step 3 to each tube (89.7 µl)–(volume of target DNA)/reaction; in this example, this is 88.71 µl.
C5. ADD target DNA of section B (0.4 µg) to tubes 1–3. In this example, this is pLITMUS28, 1 µl. This works well for plasmid targets. For cosmids, 0.5 µg worked well when the cosmid was around 10 times the size of the donor (5.2 kb) i.e. a molar ratio of around 2:1 (donor to target). Increasing the ratio to 4:1 decreased the efficiency slightly.
C6. ADD to each tube

| | Tube 1 | Tube 2 | Tube 3 |
|---|---|---|---|
| TnsA | 1.3 µl | 1.3 µl (40 ng) | 0 |
| TnsB | 3 µl | 3 µl (20 ng) | 0 |
| TnsC$_{127}$ | 1 µl | 1 µl (100 ng) | 0 |
| dH2O | 0 | 0 | 5.3 µl |

C7. ADD 1 µl donor DNA (0.1 µg pMCB40). Mix well by pipetting up and down a few times.

|  | Tube 1 | Tube 2 | Tube 3 |
|---|---|---|---|
| Donor pMCB40 | 1 µl | 1 µl | 1 µl |

C8. INCUBATE 10 minutes at 30° C. (assembly reaction)

C9. ADD 4 µl MgAc (375 mM) to each tube. Mix well by pipetting up and down a few times

|  | Tube 1 | Tube 2 | Tube 3 |
|---|---|---|---|
| MgAc | 4 µl | 4 µl | 4 µl |

C10. INCUBATE 1 hour 30° C. (transposition reaction)

C11. HEAT INACTIVATE 75° C. 10 minutes. Note: 65° C. is not adequate.

C12. TRANSFORM using chemically competent cells (see procedure of section D1):
   a. Add 10 µl of the reaction mix to 100 µl competent cells thawed on ice.
   b. Incubate 1 h on ice.
   c. Heat at 37° C. for 45 sec.
   d. Chill on ice 2 min.
   e. Dilute the transformation mix into 0.4 ml RB (total volume 0.5 ml).
   f. incubate 40 min at 37° C.
   g. plate 100 µl tubes 1–3 on Kanamycin-containing selective media.
   h. plate dilutions of tube 2 on medium selective for the target plasmid only: dilute 100 fold (10 µl/1 ml) and 1000-fold (1 µl/1 ml) and plate 100 µl of undiluted and of each dilution (3 plates)

In this example, selective medium was RB Kan (20 µg/ml) Amp (100 µg/ml) (tubes 1–3) and RB Amp (100 µg/ml, tube 2). Competent cells were ER1821, chemically competent (Section D1).

C13. Transformation result:

On Kan Amp:

Tube 1 285 colonies

Tube 2 600 colonies

Tube 3 0 colonies

On Amp only:

Tube 2 confluent (undiluted)

Section D: Recipes and Auxiliary Procedures

D1) Chemically competent cells (*E. coli*):
   a. Inoculate a single colony from an RB agar plate (see D4b) into 2 ml of RB (D4a) in a plating tube. Shake overnight at 37° C.
   b. Subculture the overnight 1:100 in 1 Volume Unit of RB+20 mM $MgSO_4$ (typically 250 ml). Grow to $OD_{590}$=0.4–0.6 or Klett=60 (~2–3 h).
   c. Centrifuge 5,000 rpm 5 min at 4° C.
   d. Gently resuspend pellet in 1/2.5 Volume Unit ice cold TFB1 (see below, D4f). Keep all steps on ice and chill all pipets, tubes, flasks, etc. from this point on.
   e. Incubate on ice for 5 min.
   f. Centrifuge 5,000 rpm 5 min 4° C.
   g. Gently resuspend pellet in 1/25 original volume cold TFB2 (D4g). For 250 ml of original subculture, use 10 ml TFB2.
   h. Incubate on ice 15–60 min. before aliquoting 100 µl/tube for storage at −70° C. Quick-freeze the tubes.
   i. To transform, thaw an aliquot on ice; add DNA; incubate 1 h on ice; heat shock 45 seconds at 37° C.; incubate on ice 2 min; dilute 5-fold into RB with no drug (for phenotypic expression); grow with vigorous aeration at 37° C. for 20 min.; plate on selective medium.

This procedure works with most strains and should routinely give >$10^7$cfu/µg of pLITMUS28 (using 0.1 ng/transformation). Frozen cells last at least a year.

D2) Electrocompetent cells (*E. coli*)

D2a. Rationale and comments

This procedure prepares cells for use in gene transfer employing an electroporator device such as that supplied by BioRad. DNA is introduced into cells by means of an electric field.

Successful electroporation requires a low electrolyte concentration, to avoid arcing (and cell killing) in the device. Cells are grown to midexponential phase, washed extensively in distilled water and sterile 10% glycerol, concentrated 500-fold in glycerol, aliquoted and stored at −70° C.

Any strain can be used for this purpose, although some strains are said to give larger numbers of transformants. Resuspended cells should be well-dispersed for best results. Some strains resuspend more evenly in the low electrolyte solutions; some lyse under these conditions with rough treatment.

The electroporation procedure itself involves transfer of the thawed cells to an electroporation cuvette (which has leads that contact the device appropriately), addition of DNA, imposition of the electric field, recovery from this treatment (by incubation in broth), and plating selectively.

Efficiency of transformation with this method is 100–500 fold greater than with standard transformation. It is therefore especially suitable when low transformation efficiency is expected or large numbers of transformants are desired. The method is said to be especially suitable for introduction of large DNA molecules.

D2b. Preparation of electrocompetent *E. coli* cells (from BioRad recommended procedure)
   i. Materials for 2 ml of electrocompetent cells (20 aliquots, 100 µl):
   overnight culture of desired strain 1 ml
   (in Rich Broth (D4a) or Luria Broth (D4c))

| Luria Broth (D4c) | 1 L |
|---|---|
| dH$_2$O, sterile, 4° C. or 0° C. | 1.5 L |
| 10% (w/v) glycerol, sterile (D4h) | 22 ml |
| 1 L sidearm flasks | 2 |
| 250 ml centrifuge bottles | 6 |
| 50 ml Oak Ridge centrifuge tubes | 2 |
| 1.5 ml microtubes, polypropylene | 20 |
| Pipet tips (sterile) for P200 or equivalent | 20 |
| Sterile glass or plastic pipets, 25 ml | 3 |

Klett-Summerson colorimeter

High speed centrifuge (e.g. Beckman J21)

Micropipetter, e.g. Gilson Pipetman P200

Water bath rack that can be used to immerse tubes in liquid nitrogen.

Liquid nitrogen bath for quick freezing ii. Procedure for making electrocompetent cells Be sure the sterile dH$_2$O and 10% glycerol is cold.

If necessary, distribute the Luria Broth to sidearm flasks, 500 ml/flask

Inoculate each flask with 0.5 ml of the overnight culture
Incubate with shaking until Klett=90 (5×10$^8$ cfu/ml).
  Quick conversion if Klett is not available: 1 OD=150
  Klett Units; 10$^9$ cells/1.1 OD)
Chill on ice with swirling, until cold. It is very important to keep everything cold from this point on.
Transfer to centrifuge bottles, 167 ml/bottle or as desired.
Centrifuge 4,000 rpm 15 min 5° C. in JA14 rotor in Beckman. Decant supernatant.
Resuspend gently in equal volume (1 L total) cold sterile distilled water. Keep in an ice bath while resuspending. Repeated pipetting will help; chill pipets for this use. MC1061 cells (ER1709) can be kept on ice at this stage for at least an hour Centrifuge 4,000 rpm 15 min 5° C. in JA14 rotor in Beckman; decant supernatant.
Resuspend gently in 1/2 volume cold sterile distilled water (0.5 L total). Keep in an ice bath while resuspending. Cells can now be combined into three bottles if desired.
Centrifuge 4,000 rpm 15 min 5° C. in JA14 rotor in Beckman. Decant supernatant. Resuspend in 1/50th volume cold sterile 10% glycerol (20 ml total). Keep cold while resuspending.
Transfer entire amount to a 50 ml Oak Ridge tube (35 ml capacity).
Centrifuige 4,000 rpm 15 min 5° C. in JA17 rotor in Beckman, with balance tube.
Decant supernatant
Resuspend in 1/500th volume (2 ml total) cold 10% glycerol. Keep cold.
Distribute 100 $\mu$l/tube to microtubes in ice water bath rack; immerse rack in liquid N$_2$; transfer to box; store at −70° C.

D2c. Procedure for electroporation of poratable *E. coli* cells (from BioRad recommended procedure)
D2ci. Materials (per electroporation reaction)

| | |
|---|---|
| Electrocompetent cells | 100 $\mu$l |
| 18 × 150 mm culture tubes | 1 |
| Electroporation cuvettes (BioRad cat #1652086 or equivalent) | 1 |
| mSOC (see D4d) | 1 ml |
| Pasteur pipets, sterile | 1 |

DNA to be transformed; in low ionic strength medium, e.g. dH$_2$O or TE (see D4i).
Electroporator (BioRad Gene Pulser or equivalent)
Ice bath trays for cuvettes and outgrowth tubes
Rollordrum in 37° C. incubator or other means of incubating culture tubes
Selective agar plates and plating materials
37° C. or suitable temperature incubator
D2cii. Procedure
Be sure all materials are set up ready to go before getting cells out of the freezer.
The DNA must be added and the electorporation done as soon as the cells are thawed; cells will lyse after a short time, resulting in arcing as the medium becomes more conductive.
Chill cuvettes and hold on ice (>5 min). Transformation efficiency declines at least 100-fold if cuvettes are at room temperature
Set BioRad Gene Pulser to 25 $\mu$F capacitance, 2.5 kV, and the pulse controller to 200 Ω (maximum voltage)
Thaw electrocompetent cells at room temperature and transfer to ice.
In a cuvette mix 40 $\mu$l cells with 0.4 pg-0.3 g DNA. Shake the suspension to the bottom of the cuvette, rap on table to shake loose air bubbles.
Place the cuvette in the holder
Apply one pulse by pushing both red buttons until a beep is heard. This will result in a pulse of 125 kV/cm with a time constant of 4–5 sec.
Immediately add 1 ml mSOC to the cuvette and gently but quickly resuspend the cells. A P1000 with sterile blue tips or sterile pasteur pipets can be used for this. A 1 min delay in adding the medium results in 3 fold decrease in transformation efficiency.
Transfer cells to culture tube.
Incubate 37° C. 1 hour
Plate on selective media.

D3) Standardization of transformation or electroporation
D3a. Rationale and comments
To ensure that gene transfer is successful, we recommend that the cells prepared above (D1 or D2) or purchased commercially be transformed with a standard DNA dilution series before experimental use. Below is an example of such a standardization for electrocompetent cells (D2). Chemically competent cells will yield 100–500 fold fewer transformants, so dilutions given below should be appropriately adjusted.

D3b. Materials for a standardization experiment
Dilutions of standard DNA, usually a high-copy small plasmid (e.g. LITMUS28), in TE:

| | |
|---|---|
| A | 1 ng/$\mu$l |
| B | 10 pg/$\mu$l |
| C | 1 pg/$\mu$l |
| D | 100 fg/$\mu$l |
| Selective agar plates; RB 1.5% Amp 100 $\mu$g/ml for pLITMUS28 | 12 |
| Dilution medium, usually 0.85% saline | 7 ml |
| Dilution tubes, usually 13 × 100 mm | 7 |
| Sterile plastic or glass pipets, 0.1 ml | 10 |
| Sterile plastic or glass pipets, 0.2 ml | 1 |
| Sterile plastic or glass pipets, 1 ml | 1 |

Micropipetters, e.g. P200 and P20 or P10, for DNA transfer and dilution series
Pipet tips for P200 and P20 or P10
Spreader
Ethanol or isopropanol for flaming the spreader
37° C. incubator
D3c. Procedure for standardization experiment
  D3ci. Set up dilution tubes below and label plates beforehand or while cultures are growing out.
  D3cii. Carry out electroporation as above (D2) with DNA dilutions A–D
  D3ciii. Place cultures on ice to prevent further growth while making dilutions and plating as below.
  D3civ. Dilute in saline:

| | |
|---|---|
| Sample A | 10$^{-1}$, 10$^{-2}$, 10$^{-3}$, 10$^{-4}$ |
| Sample B | 10$^{-1}$, 10$^{-2}$ |
| Sample C | 10$^{-1}$ |
| Sample D | no dilutions |

This can be carried out as:
10$^{-1}$ dilution: 100 $\mu$l sample+900 $\mu$l saline $10^{-2}$ dilution: 10 μl sample+1 ml saline $10^{-3}$ dilution: 10 μl $10^{-1}$ dilution+1 ml saline $10^{-4}$ dilution: 10 μl $10^{-2}$ dilution+1 ml saline.

D3cv. Plate on selective media by spreading; flame the spreader after each plate:

| Samples: | undiluted | Dilutions: | | | |
|---|---|---|---|---|---|
| | | $10^{-1}$ | $10^{-2}$ | $10^{-3}$ | $10^{-4}$ |
| A | | | 0.1 ml | 0.1 ml | 0.1 ml | 0.1 ml |
| B | 0.1 ml | 0.1 ml | 0.1 ml | | |
| C | 0.1 ml | 0.1 ml | | | |
| D | 0.1 ml | | | | |
| | 0.2 ml | | | | |
| | 0.5 ml | | | | |

D3vi. Example of result:

| Sample | DNA added | Dilution/vol plated | Colonies | Transformants per ml | per μg |
|---|---|---|---|---|---|
| A | 1 ng | 1/0.1 | Confluent | | |
| | | 2/0.1 | very numerous | | |
| | | 3/0.1 | ~1000 | | |
| | | 4/0.1 | 71 | $7 \times 10^6$ | $7 \times 10^9$ |
| B | 10 pg | 0/0.1 | very numerous | | |
| | | 1/0.1 | 405 | | |
| | | 2/0.1 | 49 | $4 \times 10^4$ | $4 \times 10^9$ |
| C | 1 pg | 0/0.1 | very numerous | | |
| | | 1/0.1 | 106 | $1 \times 10^4$ | $1.1 \times 10^{10}$ |
| D | 100 fg | 0/0.1 | ~500 | | |
| | | 0/0.2 | 173 | | |
| | | 0/0.5 | 75 | $8 \times 10^2$ | $8 \times 10^9$ |

Average transformants/μg $7.6 \times 10^9$

D4) Recipes

Bacteriological

D4a) RB, per liter

| Tryptone (Difco) | 10 g |
|---|---|
| Yeast Extract (Difco) | 5 g |
| NaCl | 5 g |
| NaOH (1 N) | 2 ml |

Autoclave

D4b) RB Agar with drug, per liter

| Tryptone (Difco) | 10 g |
|---|---|
| Yeast Extract (Difco) | 5 g |
| NaCl (Baker) | 5 g |
| NaOH (1 N) | 2 ml |
| Agar (Difco) | 15 g |

Autoclave

Drugs: add after autoclaving and cooling to 55° C., per liter:

Kanamycin (REQUIRED) 20 mg

Other drugs that MAY be added, per liter; choice depends on target plasmid:

| Ampicillin or carbenicillin | 100 mg |
|---|---|
| Chloramphenicol | 15 mg |
| Tetracycline | 15 mg |

Others drugs not tested but presumably usable in an appropriate host strain:

Spectinomycin

Streptomycin

Gentamycin

Erythromycin

Rifampicin (recessive marker)

Bleomycin

Other antibacterial small molecules

D4c) Luria Broth, per liter

| Tryptone | 10 g |
|---|---|
| Yeast extract | 5 g |
| NaCl | 10 g |
| $MgCl_2.6H_2O$ | 1 g |
| glucose | 1 g |

Aliquot and autoclave. For preparing electrocompetent cells (C2) it is convenient to aliquot 500 ml/flask in 1 L sidearm flasks before autoclaving.

D4d) mSOC, per liter (modified from BioRad recipe)

| Luria Broth | 1 L |
|---|---|
| $MgSO_4$, 1 M sterile | 10 ml |
| 40% glucose, sterile | 6.5 ml |

Add $MgSO_4$ and glucose sterilely to sterile Luria Broth

D4e) 0.85% saline, per liter

NaCl 8.5 g

Distribute in suitable aliquots, autoclave.

Buffers and storage media

D4f). TFBI 30 mM KOAc (potassium acetate)

100 mM RbCl 10 mM $CaCl_2$ 50 mM $MnCl_2$

15% glycerol

Adjust to pH 5.8 with acetic acid and filter to sterilize. It is convenient to make this as:

5 g RbCl (Alfa)

| 12.3 ml KOAc | 1 M |
|---|---|
| 4.1 ml $CaCl_2$ | 1 M |
| 20.5 ml $MnCl_2$ | 1 M (this is pink) |

61.5 g glycerol; pH to 5.8 with $\leq 8$ ml HOAc 0.1 M make up to 410 ml; distribute in 100 ml sterile aliquots; and use 1 aliquot/250 ml culture.

D4g). TFBII 10 mM MOPS 75 mM $CaCl_2$ 10 mM RbCl

15% glycerol

Adjust pH to 6.5 with KOH and filter to sterilize
Make up as 1.5 ml MOPS 1 M pH 6.5 (this is yellow)
11.25 ml CaCl$_2$ 1 M
1.5 ml RbCl 1 M
22.5 g glycerol
pH with 1 N KOH; make to 150 ml, filter; use 10 ml per original 250 ml culture.

D4h) 10% glycerol, per liter

| Glycerol | 100 g |
|---|---|
| dH$_2$O | 1 L |

Aliquot and autoclave

D4i) TE, per liter

| 1 M Tris pH 8.0 | 10 ml |
|---|---|
| 0.5 M EDTA pH 8.0 | 2 ml |

Example 4

Random Insertion of Primers for Sequencing

Section A: Components Used for Transposition Reaction

A1) PROTEINS

TnsA 40 µg/ml in 10% glycerol
TnsB 20 µg/ml in 50% glycerol
TnsC$_{127}$ 100 µg/ml in 50% glycerol
Stored at −70° C.

A2) BUFFER CONSTITUENTS

| HEPES | 0.25 M pH 8.1 |
|---|---|
| Tris[Cl] | 0.25 M pH 7.6 [can be omitted] |
| BSA | 10 mg/ml |
| tRNA | 50 µg/ml |
| DTT | 1 M |
| ATP pH7 | 100 mM |
| MgAcetate | 375 mM |
| TnsD storage buffer | TnsD is stored in the following buffer: 3.3 µl 500 mM KCl, 50 mM Tris-HCl (pH 8.0), 1 mM EDTA, 2 mM DTT and 25% glycerol |

Figure 9A:
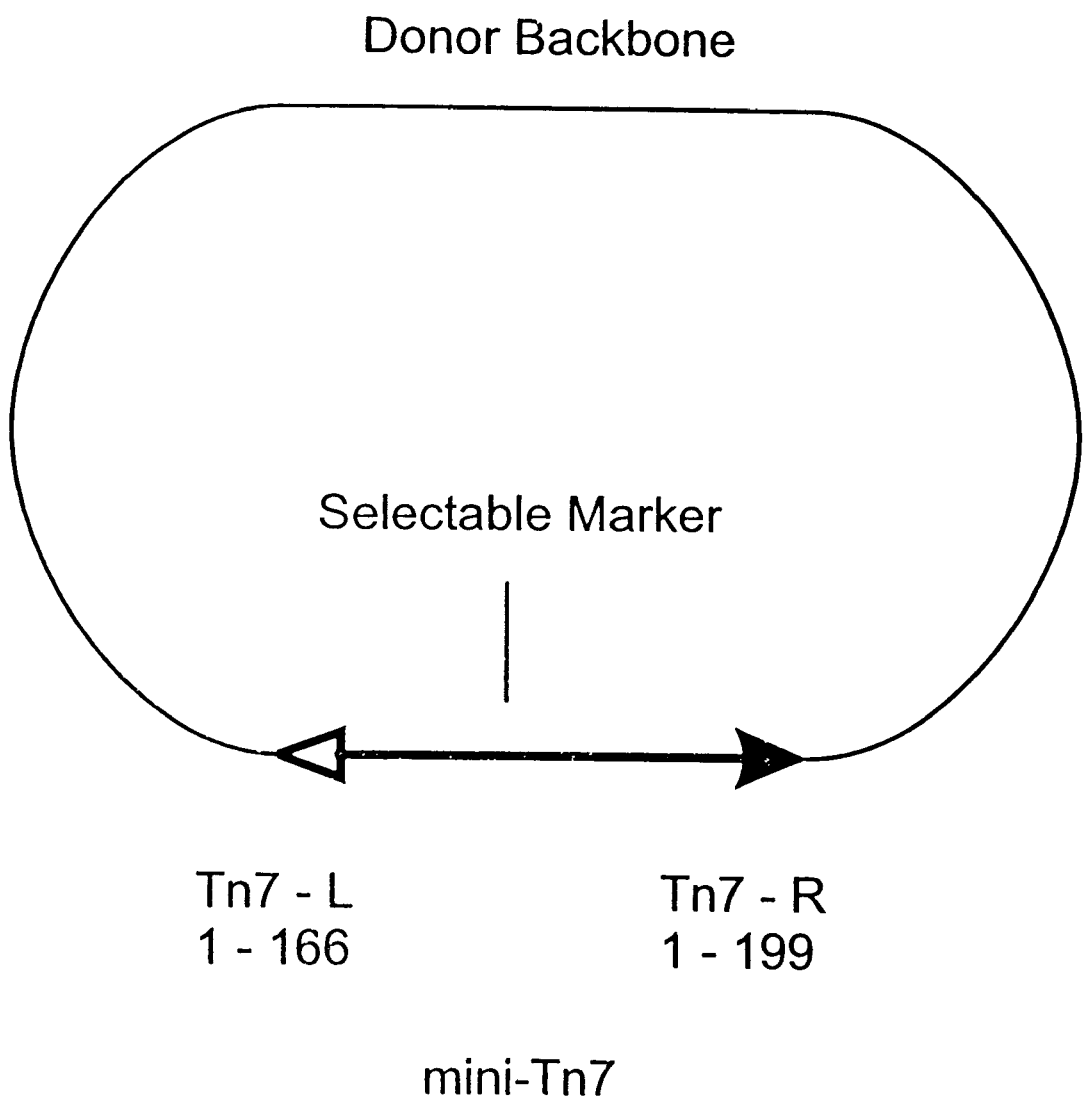

A3) TRANSPOSON DONOR PLASMID pEM delta R.adj to 1 50 µg/ml (Sequence appears in FIG. 9B and SEQ ID NO:3)

A4) TARGET PLASMID

| 1) pER183 mini-cleared lysate | 200 µg/ml |
|---|---|
| 2) pER183 CsCl preparation | 400 µg/ml |
| 3) pRM2 | 400 µg/ml |

(Sequence of pER183 appears in FIG. 10A and SEQ ID NO: 5)

Section B: Components Used for Processing Reaction

Phenol/chloroform equilibrated with TE
Phenol equilibrated with Tris pH 8.0
NaAcetate 3 M
Ethanol (EtOH)
BstEII New England BioLabs, 32 Tozer Road, Beverly, Mass., 01915
DNA Polymerase I Holoenzyme New England BioLabs, 32 Tozer Road, Beverly, Mass., 01915
T4 DNA Ligase New England BioLabs, 32 Tozer Road, Beverly, Mass., 01915
10×Fi/L buffer (section I3)
10×Buffer 3 (NEB#007-3) New England BioLabs, 32 Tozer Road, Beverly, Mass., 01915
tRNA 1 mg/ml
DNA buffer (section I2)
TE (section I4)

Section C: Components Used for Recovery of Insertions

MC1061 electrocompetent cells (made and used as in Example 3, D2 and D3)
Selective media (made and used as in Example 3, D3 and D4)

Section D: Components Used for Sequence Determination

D1) SEQUENCING PRIMERS

NLC94 3.2 pmol/µl.
Sequence of this primer (SEQ ID NO:13): 5' AAAGTC-CAGTATGCTTTTTCACAGCATAAC
NLC95 3.2 pmol/µl
Sequence of this primer (SEQ ID NO:7) 5' ATAATCCT-TAAAAACTCCATTTCCACCCCT D2) QIAPREP SPIN MINIPREP KIT (Qiagen Cat#27106)

D3) ABI Sequencer (info) and reagents

Section E: In Vitro Transposition Protocol

E1) MAKE UP Mix:

| 208.2 µl | dH$_2$O |
|---|---|
| 30 µl | Hepes (250 mM pH 8.1) |
| 3 µl | Tris (250 mM pH 7.6) |
| 1.5 µl | BSA (10 mg/ml) |
| 6.3 µl | tRNA (50 µg/ml) |
| 0.6 µl | DTT (1 M) |
| 6 µl | ATP (100 mM) |

E2) DISPENSE 85.2 µl to three tubes
E3) ADD target DNA of A4, 2 µl
E4) ADD to each tube

| | Tube 1 | Tube 2 | Tube 3 |
|---|---|---|---|
| TnsA | 1.3 µl | 1.3 1µl | 1.3 µl |
| TnsB | 1 µl | 1 µl | 1 µl |
| TnsC$_{127}$ | 1 µl | 1 µl | 1 µl |
| D buffer | 3.3 | 3.3 | 3.3 µl |
| Donor | 2 | 2 | 2 µl |

E5) INCUBATE 30 minutes at 30° C. (assembly reaction)
E6) ADD 4 µl MgAc (375 mM) to each tube.
E7) INCUBATE 1 hour at 30° C. (insertion)

Section F: Reaction Processing

In this example, the transposon donor was capable of replicating in the host used for recovery of insertions. Tranformation of the reaction mixture on plates selecting for the transposon and the target markers might well result in many colonies with two different plasmids, rather than with a single plasmid containing both markers. For this reason, we digested the reaction with a restriction endonuclease cleaving in the donor replicon but not within the transposon or in the target DNA. In addition, we examined the consequences of repairing the strands not ligated by the transposition reaction, using DNA polymerase I holoenzyme and ligase.

Per reaction (100 μl):
PC extract:
  Add 100 μl phenol/chloroform, vortex
  Centrifuge 5' in microfuge
Backextract
  Remove organic phase to a new tube with 100 μl TE; vortex
  Centrifuge 5' in microfuge
  Combine aqueous phases (185 μl total)
EtOH precipitate

| 20 μl | 3 M NaAc |
| 500 μl | EtOH | chill on dry ice
Centrifuge 5 min in microfuge
Drain supernatant, air dry
Resuspend in 100 μl DNA buffer
Divide each reaction for further treatment (all volumes are μl)

| Treatment: | Repair Digestion A | Digest B |
|---|---|---|
| 1) Repair/ligation | | |
| DNA | 40 | 40 |
| 10X Fi/L | 5 | — |
| dH$_2$O | 2 | — |
| Pol I (10,000 μ/ml) | 2 | — |
| a) Incubate 15 min room temperature | | |
| Ligase (400,000 u/ml) | 1 | |
| b) Incubate 4 h 16° C. | | |
| 2) Digestion | | |
| 1 M NaCl | 6.0 | — |
| 10 X buffer 3 | — | 6.0 |
| BstEII (10,000 u/ml) | 1 | 1 |
| Incubate 60° C. 1 h | | |
| 3) Protein removal, buffer exchange 1 | | |
| Phenol, equilibrated | 50 | 50 |
| a) Mix, centrifuge 5' in microfuge | | |
| b) Back extract organic phase with DNA buffer | | |
| c) Combine aqueous phase | | |

| Treatment: | Repair Digestion A | Digest B |
|---|---|---|
| Total volume, step 3c | 100 | 100 |
| 3 M NaAc | 10 | 10 |
| tRNA 1 mg/ml | 1 | 1 |
| EtOH | 120 | 120 |
| a) Incubate 5 min room temperature | | |
| b) Centrifuge, discard supernatant | | |
| c) Wash twice with cold 70% EtOH (100 μl) | | |
| DNAbuffer | 50 | 50 |
| d) Resuspend | | |
| Final volume, step 3d | 50 | 50 |
| 4) Buffer exchange 2 | | |
| Re-precipitation | | |
| DNA from step 3d | 35 | 35 |
| 3 M NaAc | 5 | 5 |
| EtOH | 137.5 | 137.5 |
| a) Incubate −70° C. overnight | | |
| b) Centrifuge, discard supernatant | | |
| c) wash twice 200 μl 70% EtOH | | |
| TE | 50 | 50 |
| d) Resuspend | | |

Section G: Recovery of Insertions

Electroporated 10 μl of samples into MC1061 following procedure of Example 3, section D3

TABLE 2

Sample codes, treatments, and target concentrations corrected for losses during manipulation

| | Target name | Treatment | Target Selection | [Target DNA] (fmol/μl) |
|---|---|---|---|---|
| 1A | pER183 | Fi/L, Dig | Cam | 0.015 |
| 1B | pER183 | Digested | Cam | 0.05 |
| 2A | pER183 | Fi/L, Dig | Cam | 0.98 |
| 2B | pER183 | Digested | Cam | 0.42 |
| 3A | pRM2 | Fi/L, Dig | Amp | 0.66 |
| 3B | pRM2 | Digested | Amp | 0.56 |

TABLE 3

Colony forming units per ml on appropriate selective plates

| Sample | 1A | 1B | 2A | 2B | 3A | 3B |
|---|---|---|---|---|---|---|
| Donor (or recomb) Kan Only | | | | | | |
| Recipient | 130 | $1.8 \times 10^5$ | $5 \times 10^3$ | $7 \times 10^3$ | $3.7 \times 10^4$ | $4 \times 10^4$ |
| Cam only | $1 \times 10^4$ | $8 \times 10^5$ | $4 \times 10^4$ | $6 \times 10^6$ | | |
| Amp only | | | | | $3 \times 10^7$ | $4 \times 10^7$ |
| Colonies/fmol Recombinant | $6 \times 10^4$ | $1.6 \times 10^6$ | $4 \times 10^3$ | $1.4 \times 10^6$ | $4.5 \times 10^6$ | $7 \times 10^6$ |
| KanCam | 16 | $2.7 \times 10^3$ | 880 | $1 \times 10^4$ | | |
| Kan Amp | | | | | $1.1 \times 10^5$ | $4 \times 10^4$ |
| Recomb/recip | $1 \times 10^{-3}$ | $3 \times 10^{-3}$ | $2 \times 10^{-2}$ | $1 \times 10^{-3}$ | $4 \times 10^{-3}$ | $1 \times 10^{-3}$ |

75 recombinant colonies were chosen, 31 from samples 2A, 44 from samples 2B, for further characterization H. Determination of Sequence Location 1. Procedure Summary 75 recombinant colonies were picked into 0.5 ml RB in racked array for storage. Subcultures of these storage cultures were grown with selection (RB Cam Kan), and minipreps made according to the directions of the manufacturer for large plasmids of low copy number.

DNA concentration of the plasmid preps was determined by comparison with a dilution series of linearized pLIT-MUS28 on agarose gels. Plasmid preps were linearized for this purpose with an enzyme that cleaves once in the target plasmid and not in the transposon (SacII).

Primers NLC94 and NLC95 (SEQ ID NOS: 13 and 7, respectively) were used for sequence determination, using flourescently-labeled dideoxynucleotide sequencing reagents from Applied Biosystems.

Sequences were run on an ABI sequencer, and sequence acquisition, editing and assembly was carried out with the supplied programs (SEQED, FACTURA and AUTOASSEMBLE).

Figure 11:
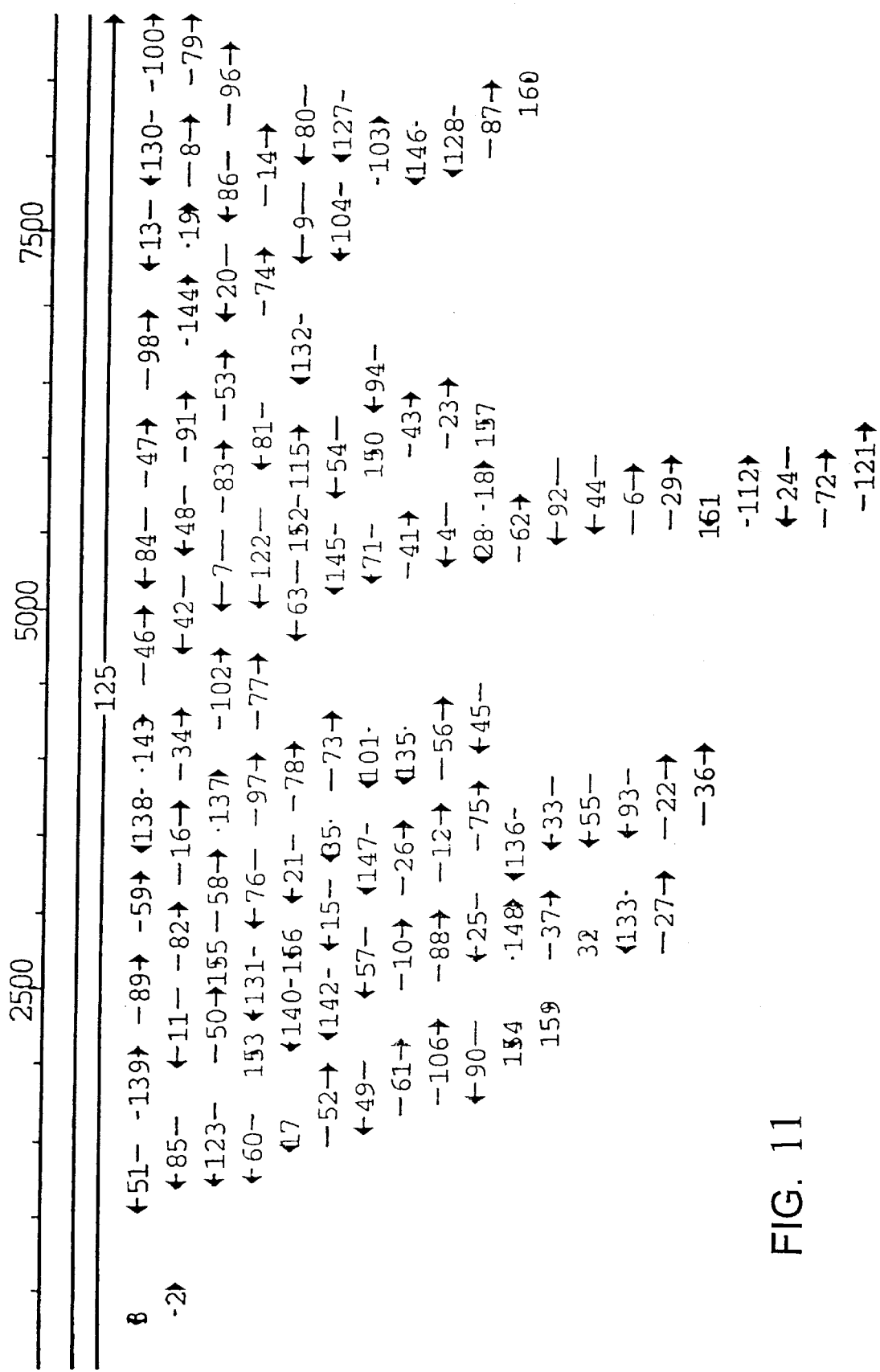
FIG. 11. Diagram of sequencing runs used to ascertain the positions of 63 insertions of mini-Tn7 into pER183 (SEQ ID NO:5). Numbers at the top refer to coordinates on the sequence of pER183 (SEQ ID NO:5) displayed in FIG. 11B. Arrows indicate the direction of primer extension; arrow stems cover the sequence obtained from the run. Arbitrary numbers attached to the arrows assigned by the sequence assembly program AUTOASSEMBLE.

Output is FIG. 11

2. Results

TABLE 4 a. Summary result of 75 recombinants (CamR KanR colonies), potential Tn7 insertions into pER183.

| | |
|---|---|
| Total DNA preps | 75 |
| DNA concentration too low to attempt sequence: | 7 |
| Transformant contained two plasmids, not sequenced: | 1 |
| Total not sequenced | 8 |
| DNA preps sequence attempted | 67 |
| Sequence unreadable (miscellaneous reasons) | 2 |
| Sequence unreadable because 2 insertions in one plasmid | 1 |
| Total sequence unreadable | 3 |
| DNA preps sequence obtained | 64 |
| Sequence rejected (cross contamination of adjacent wells) | 1 |
| Total insertions rejected | 1 |
| Independent insertions for which location was obtained | 63 |
| Number of insertion locations | 62 |
| Number inserted clockwise | 33 |
| Number inserted counterclockwise | 30 |
| Aberrant insertions | |
| Number of insertion plasmids with structural aberrations | 1 |
| This was a deletion far from the insertion | |
| Number of structural aberrations associated with insertion site | 0 |
| Number of insertions with disagreement in 5 bp duplication | 2 |

These were:
G–>A transition mutation in one copy with respect to target plasmid sequence
G–>T transversion mutation in one copy with respect to target plasmid sequence.

b. Analysis of the distribution of insertions among sequences and intervals.

For the purpose of obtaining maximum sequence from an unknown target, it is desirable that the insertions be distributed as randomly as possible with respect to regions of sequence and with respect to specific sequences. The summary of Table 4 already suggests a very random process, since 63 independent insertions hit 62 different locations, i.e. no hotspots for insertion were identified. For comparison, relaxed-specificity derivative of Tn10 (ATS2, examined with in vivo insertions into the lac operon) hit 23 sites with 50 insertions.

Primary data for further analysis below is found in Table 5, which gives the location of all the insertions, their orientation with respect to the target plasmid, and the sequence immediately adjacent to the insertion (the five bp sequence duplicated by the insertion mechanism) in a uniform frame of reference.

TABLE 5

Insertion locations and associated 5 bp duplication

| Isolate | direction sequence obtained | Insert location | Insert name | \multicolumn{5}{c}{Sequence at position relative to Tn7R} | orientation (Tn7 R clockwise = +) |
|---|---|---|---|---|---|---|---|---|---|
| | | | | 1 | 2 | 3 | 4 | 5 | |
| 1 | 1 | 6464 | A5 | A | G | C | T | C | − |
| 2 | 2 | 8428 | A6 | C | T | G | G | T | − |
| 3 | 1 | 8349 | A7 | C | C | T | G | A | + |
| 4 | 2 | 5515 | A8 | T | A | A | C | T | + |
| 5 | 2 | 7822 | A9 | C | C | C | G | C | + |
| 6 | 2 | 365 | A10 | T | C | A | A | C | + |
| 7 | 2 | 5695 | A11 | T | C | A | C | G | − |
| 9 | 2 | 2500 | B1 | G | G | A | T | G | + |
| 10 | 1 | 8286 | B2 | C | T | T | C | C | + |
| 11 | 1 | 2764 | B3 | C | T | T | T | A | + |
| 12 | 2 | 6953 | B4 | C | G | A | G | G | + |
| 13 | 2 | 3414 | B5 | C | T | T | T | G | + |
| 14 | 1 | 3139 | B6 | T | C | G | T | T | − |
| 15 | 1 | 3208 | B7 | G | C | A | C | T | − |
| 16 | 2 | 4208 | B8 | A | G | A | G | C | − |
| 17 | 2 | 3671 | B9 | G | T | T | T | A | + |
| 18 | 2 | 5563 | B10 | C | C | A | A | C | − |
| 19 | 1 | 3539 | B11 | G | C | T | T | C | + |
| 20 | 2 | 3803 | B12 | A | T | T | C | C | − |
| 21 | 2 | 8474 | C1 | C | C | G | C | C | + |
| 22 | 2 | 5661 | C2 | A | T | G | A | T | + |
| 23 | 2 | 7693 | C3 | C | G | C | G | T | − |
| 24 | 2 | 3205 | C4 | T | C | T | T | C | − |
| 25 | 2 | 1650 | C5 | C | C | T | A | T | − |
| 26 | 2 | 8020 | C6 | G | C | C | G | G | − |
| 27 | 2 | 2566 | C7 | A | T | T | T | T | + |
| 29 | 2 | 2275 | C9 | G | C | C | C | A | + |
| 30 | 1 | 6368 | C10 | G | C | T | A | T | − |
| 32 | 2 | 2629 | C12 | T | A | T | A | C | + |
| 33 | 2 | 5988 | D1 | G | G | C | G | A | + |
| 34 | 2 | 3499 | D2 | A | T | G | T | A | − |
| 35 | 2 | 3933 | D3 | T | T | G | A | T | − |
| 36 | 2 | 6077 | D4 | G | T | T | G | T | + |
| 37 | 2 | 6756 | D5 | T | T | G | A | G | − |
| 38 | 2 | 5563 | D6 | G | T | T | G | G | + |
| 38 | 2 | 8224 | D7 | G | G | A | G | G | − |
| 40 | 2 | 3123 | D8 | C | A | A | A | T | − |
| 41 | 1 | 2746 | D9 | A | A | A | A | C | − |
| 42 | 1 | 1646 | D10 | C | G | A | G | A | + |
| 43 | 1 | 5678 | D11 | A | T | G | T | G | + |
| 44 | 2 | 7406 | D12 | T | G | C | A | T | + |
| 45 | 2 | 1744 | E1 | G | C | C | A | T | − |
| 46 | 2 | 3584 | E2 | T | A | G | G | T | + |
| 47 | 2 | 2112 | E3 | C | C | T | A | C | + |
| 48 | 2 | 4205 | E4 | G | C | A | G | C | − |
| 49 | 1 | 2708 | E5 | G | C | G | 0 | T | + |
| 50 | 2 | 7828 | E6 | A | C | A | G | A | + |
| 52 | 2 | 3873 | E8 | A | G | T | C | T | − |
| 53 | 2 | 3591 | E9 | C | A | T | G | C | − |
| 56 | 2 | 5550 | E12 | A | T | C | G | C | − |
| 57 | 2 | 2702 | F1 | T | T | C | A | C | + |
| 61 | 2 | 4490 | F5 | G | T | T | A | A | − |
| 62 | 2 | 5811 | F6 | A | C | G | C | G | + |
| 63 | 2 | 2024 | F7 | A | C | T | G | T | − |
| 64 | 2 | 1479 | F8 | A | T | C | G | T | − |
| 66 | 2 | 5675 | F10 | T | T | T | A | T | + |
| 67 | 2 | 5208 | F11 | A | T | A | A | A | + |
| 68 | 2 | 6020 | F12 | G | G | T | A | A | + |
| 69 | 2 | 6264 | G1 | G | A | G | T | A | + |
| 70 | 2 | 3881 | G2 | A | T | T | T | G | − |
| 72 | 2 | 2891 | G4 | A | T | T | C | G | − |
| 74 | 2 | 1681 | G6 | A | C | T | C | T | − |
| 76 | 2 | 5315 | G7 | A | A | T | A | C | + |

Table 5 legend:

Isolate: Number of the colony

Directions sequenced: 1=only one direction from the insertion; 2=both directions Position: coordinate on pER183 (SEQ ID NO:5) top strand of the first base of the 5 bp duplication Insert name: accession number in notebook Sequence at position #: position 1 is the base immediately adjacent to Tn7R top strand
(i.e. it can be either the top or the bottom strand of pER183 (SEQ ID NO:5)); position #2 is the next but one to Tn7R; and so forth.

Orientation: of the insertion relative to the top strand of pER183 (SEQ ID NO:5). +, Tn7R is to the right of Tn7L when displayed on the top strand of pER183 (SEQ ID NO:5). −, Tn7R is to the left of Tn7L.

i. Distribution of insertions fits the Poisson distribution a. These insertions are randomly distributed as judged by the fit of the interval distribution to the distribution predicted by a Poisson process.

The Poisson distribution gives the probability of observing exactly $X_i$ events (insertions) in a unit (interval) when the average number of events per unit is $\mu$ (from Zar, J. H. *Biostatistical Analysis* Prentice-Hall, Englewood Cliffs, N.J. 1974 p.301).

$$P(X_1) = \frac{\mu^{X_i} e^{-\mu}}{X_i!} \qquad \text{eq 1}$$

Where $X_i$=exactly $X_i$ insertions per interval $\mu$=average number of insertions per interval Let $X_i$=number of insertions in a 100 bp interval $f_i$=Observed number of 100 bp intervals with $X_i$ insertions/interval n=number of 100 bp intervals in the set (=73)

$\mu = \Sigma f_i X_i / \Sigma f_i = 63/73$ $P_{(xi)}$=probability of finding $X_i$ insertions in a 100 bp interval (from the Poisson distribution,. eq 1)

$F_i = P_{(xi)} n$=expected number of intervals with i insertions.

From the data in Table 5 and eq 1 we can construct the following comparison of expected and observed data:

TABLE 6

Observed and expected distribution of insertions in 100 bp intervals

| Insertions per interval $X_i$ | Observed intervals with $X_i$ insertions $f_i$ | Probability of $X_i$ insertions per interval $P(X_i)$ | Expected number of intervals with $X_i$ insertions $F_i$ |
|---|---|---|---|
| 0 | 34 | 0.42189 | 30.80 |
| 1 | 24 | 0.36410 | 26.58 |
| 2 | 9 | 0.15711 | 11.47 |
| 3 | 3 | 0.04520 | 3.299 |
| 4 | 3 | 0.00975 | 0.712 |

Figure 12:
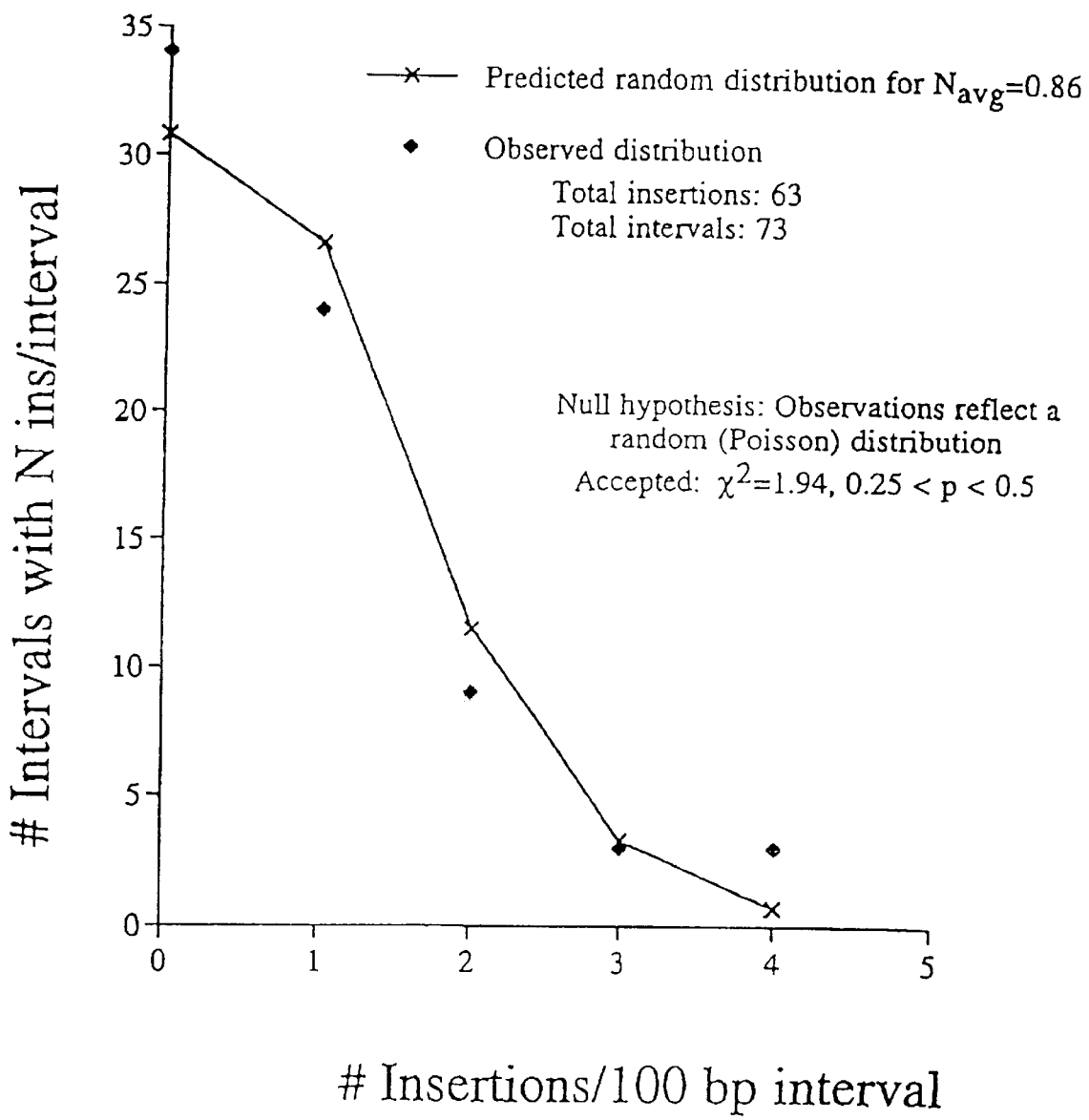
FIG. 12. Graph of the observed distribution of insertions in 100-bp intervals of pER183 (SEQ ID NO:5), and the distribution expected if the distribution were random. On the abcissa is the number of insertions per interval; on the ordinate is the number of intervals that exhibit that number of insertions. Crosses show the expected values for a random (Poisson) distribution of insertions along the sequence; diamonds show the observed values.

These distributions are illustrated in FIG. 12, where fi=observed distribution, Fi=expected distribution. The fit looks good to the eye.

b. Statistical test of fit between observed and expected distributions

To test whether the observed and expected distribution are statistically indistinguishable, we used a Chi-square test for goodness of fit (from Zar, J. H. *Biostatistical Analysis* Prentice-Hall, Englewood Cliffs, N.J. 1974 p.303). For this purpose we pool the tail of the distribution so that no expected number is less than 4. Rewriting Table 6, we obtain

TABLE 7

Chi-square test of goodness of fit to a random distribution

| Insertions per interval $X_i$ | | Observed intervals with $X_i$ insertions | |
|---|---|---|---|
| | 0 | | 34 |
| | 1 | | 24 |
| | 2 | | 9 |
| | ≧3 | $f_i$ | 6 |
| Expected number of intervals with $X_i$ insertions $F_i$ | $(f_i - F_i)^2$ / $F_i$ Chi-square | | |
| 30.80 | 0.3329 | | |
| 26.58 | 0.2504 | | |
| 11.47 | 0.5315 | | |
| 4.1541 | 0.8209 | | |
| Sum | 1.944 | | |

The null hypothesis is that the observed distribution was drawn from a Poisson distributed population. For two degrees of freedom this sum of chi-square values gives a probability that this is the case of 0.25<p<0.5. The null hypothesis is not rejected.

In sum, the eye (part a, FIG. 12) and a statistical test (Table 7 and following) agree that the distribution of insertions in intervals along the DNA is random.

ii. Analysis of the base composition of insertion sites.

Site Preference of TnsABC$_{127}$ for Insertion of miniTn7 into pER183

Certain bases are preferred at some positions in the five-base insertion site duplication, as shown in a histogram of base incidence versus position in the site (FIG. 13), taken from the data in Table 5. In collating the data for this histogram, the five duplicated bases were assigned position numbers relative to Tn7R; position one is the base immediately adjacent to Tn7R when the sequence is displayed with Tn7R on the right and Tn7L on the left. The orientation of the transposon relative to the target sequence during target choice is thus controlled for: the target is displayed in the same way relative to the transposon for all insertion sites.

A model for a preferred site was formulated: NYTRN. The elements of this site were tested for statistical significance individually and collectively by chi-square analysis (Table 8). The null hypothesis was that sites were drawn randomly from the universe of sequence defined by the sequence of pER183 (SEQ ID NO:5) after deleting sequence subject to selection (bp 1–250 and 2481–2509, CamR; and 581–1400, replication origin). Expected frequencies of the four bases, of purines and pyrimidines, and of trinucleotides were derived from frequencies obtained for pER183 (SEQ ID NO:5)-condensed by the GCG program COMPOSITION.

TABLE 8

Chi-square tests (tests that differ from random expectation (p < 0.05) in bold)

Four bases individually, all sites collectively (315 bp experimental, 7410 bp control)

| Base | Expected | Observed | Chisquare probability |
|---|---|---|---|
| A | 78.4 | 73 | .372 |
| C | 74.3 | 77 | .981 |
| G | 76.2 | 72 | .232 |

TABLE 8-continued

Chi-square tests (tests that differ from random expectation (p < 0.05) in bold)

| | | | | |
|---|---|---|---|---|
| T | 85.7 | 93 | .622 | |
| | | | 2.21 | 0.5 < p < 0.75 |

Four bases individually, each position individually (63 bp experimental, 7810 bp control)

Position 1

| | | | | |
|---|---|---|---|---|
| A | 15.7 | 19 | 0.694 | |
| C | 14.9 | 15 | 0.00066 | |
| G | 15.2 | 17 | 0.213 | |
| T | 17.1 | 12 | 1.12 | |
| | | | 2.43 | 0.25 < p < 0.5 |

Position 2

| | | | | |
|---|---|---|---|---|
| A | 15.7 | 8 | 3.8 | |
| C | 14.9 | 22 | 3.38 | |
| G | 15.2 | 11 | 1.16 | |
| T | 17.1 | 22 | 1.4 | |
| | | | 9.74 | 0.01 < p < 0.925 |

Position 3

| | | | | |
|---|---|---|---|---|
| A | 15.7 | 15 | 0.031 | |
| C | 14.9 | 11 | 1.02 | |
| G | 15.2 | 12 | 0.674 | |
| T | 17.1 | 25 | 3.65 | |
| | | | 5.37 | 0.1 < p < 0.25 |

Position 4

| | | | | |
|---|---|---|---|---|
| A | 15.7 | 19 | 0.693 | |
| C | 14.9 | 11 | 1.02 | |
| G | 15.2 | 20 | 1.52 | |
| T | 17.1 | 13 | 0.983 | |
| | | | 4.21 | 0.1 < p < 0.25 |

Position 5

| | | | | |
|---|---|---|---|---|
| A | 15.7 | 12 | 0.872 | |
| C | 14.9 | 18 | 0.645 | |
| G | 15.2 | 12 | 0.674 | |
| T | 17.1 | 21 | 0.889 | |
| | | | 3.08 | 0.25 < p < 0.5 |

Purines and Pyrimidines, each position individually (63 bp experimental, 7410 bp control)

| Base | Expected | Observed | Chisquare | probability |
|---|---|---|---|---|

Position 1

| | | | | |
|---|---|---|---|---|
| R | 30.9 | 36 | 0.842 | |
| Y | 32.1 | 27 | 0.810 | |
| | | | 1.65 | 0.1 < p < 0.25 |

Position 2

| | | | | |
|---|---|---|---|---|
| R | 30.9 | 19 | 4.58 | |
| Y | 32.1 | 44 | 4.41 | |
| | | | 8.99 | 0.001 < p < 0.005 |

Position 3

| | | | | |
|---|---|---|---|---|
| R | 30.9 | 27 | 0.49 | |
| Y | 32.1 | 36 | 0.422 | |
| | | | 0.914 | 0.25 < p < 0.5 |

Position 4

| | | | | |
|---|---|---|---|---|
| R | 30.9 | 39 | 2.12 | |
| Y | 32.1 | 24 | 2.04 | |
| | | | 4.17 | 0.025 < p < 0.05 |

Position 5

| | | | | |
|---|---|---|---|---|
| R | 30.9 | 24 | 1.54 | |
| Y | 32.1 | 39 | 1.48 | |
| | | | 3.10 | 0.05 < p < 0.1 |

T or not-T, position 3

| | | | | |
|---|---|---|---|---|
| T | 17.16 | 25 | 3.58 | |
| not-T | 45.84 | 38 | 1.34 | |
| | | | 4.92 | 0.025 < p < 0.05 |

Triplets, positions 234 (63 experimental triplets, 7408 control triplets to determine expectation)

All triplets

| Triplet | Expected | Observed | Chisquare | probability |
|---|---|---|---|---|
| YNR | 15.96 | 25 | 7.54 | |
| RNY | 15.97 | 5 | 5.12 | |
| RNR | 14.98 | 14 | 0.064 | |
| YNY | 16.07 | 19 | 0.534 | |
| | | | 13.25 | 0.001 < p < 0.005 |

Specific triplets, positions 234

| | | | | |
|---|---|---|---|---|
| YNR | 16 | 25 | 5.06 | |
| Not YNR | 47 | 38 | 1.7 | |
| | | | 6.78 | 0.005 < p < 0.01 |
| RNY | 16 | 5 | 7.56 | |
| Not RNY | 47 | 59 | 3.06 | |
| | | | 10.62 | 0.001 < p < 0.005 |
| YTR | 3.93 | 10 | 9.38 | |
| not YTR | 59.07 | 53 | 0.623 | |
| | | | 10.0 | 0.001 < p < 0.005 |

Pairing between position 2 and 4 (GNC, CNG, ANT, TNA)

| | | | | |
|---|---|---|---|---|
| Paired | 16.95 | 16 | 0.053 | |
| Not paired | 46.05 | 47 | 0.0196 | |
| | | | 0.073 | 0.75 < p < 0.9 |

Preference for this site was statistically significant (p<0.005), and preference for each of its parts was also significant (p<0.05). However, the preference is not particularly strong, in that representation of the site was only 2.5-fold more frequent in insertion sites than expected from the composition of the plasmid; and 53 out of 63 sites do not fit the consensus. Each preferred position contributes independently to the overall preference, since multiplying together the overrepresentation of each position yields the overrrepresentation of the site as a whole (Table 9).

TABLE 9 overrepresentation of preferred bases in Tn7 insertion sites

| Position | preference | expected | observed | Fold overrepresentation (Obs/Exp) |
|---|---|---|---|---|
| 2 | Y | 32.1 | 44 | 1.37 |
| 3 | T | 17.6 | 25 | 1.42 |
| 4 | R | 30.9 | 39 | 1.26 |
| product | ((O/E)2 × (O/E)3 × (O/E)4) | | | 2.46 |
| triplet | YTR | 3.93 | 10 | 2.54 |

We conclude that insertion mediated by $TnsABC_{127}$ is extremely random, with only a slight preference for sites of the form NYTRN (SEQ ID NO:15).

| I. Recipes. | | |
|---|---|---|
| 1. | 100 X DNA buffer per liter | |
| | Tris Base | 121.1 g |
| | Dissolve in 700 ml | |
| | 4M HCl | ~90 ml |
| | Bring pH to 7.4 | |
| | $Na_2EDTA$ | 37.2 |
| | NaCl | 29.22 g |
| | Make up to ~950 ml | |
| | adjust pH | |
| | Make up to 1 L | |
| | Aliquot, autoclave | |
| 2. | 1 X DNA buffer | |
| | 100 × DNA buffer | 1 ml |
| | $dH_2O$, sterile | 100 ml |
| 3. | 10 X Fi/L (Fill-in, ligation) buffer | |
| | 10 X ligase buffer | 1.500 µl |
| | New England BioLabs, 32 Tozer Road, Beverly, Massachusetts, 01915 | |
| | 100 mM dATP | 3.75 µl |
| | New England BioLabs, 32 Tozer Road, Beverly, Massachusetts, 01915 | |
| | 100 mM dCTP | 3.75 µl |
| | New England BioLabs, 32 Tozer Road, Beverly, Massachusetts, 01915 | |
| | 100 mM dGTP | 3.75 µl |
| | New England BioLabs, 32 Tozer Road, Beverly, Massachusetts, 01915 | |
| | 100 mM dTTP | 3.75 µl |
| | New England BioLabs, 32 Tozer Road, Beverly, Massachusetts, 01915 | |
| 4. | TE | |
| | 1M Tris pH 8.0 | 1 ml |
| | 0.5 M EDTA pH 8.0 | 0.2 ml |
| | $dH_2O$ | to 100 ml |
| | Filter sterilise | |

Example 5

A Convenient Method for Stopping a Transposon Insertion Reaction

In order to use DNA molecules with transposon insertions, they must be recovered in vivo. It is most convenient to be able to do this without the labor and losses associated with extraction with organic solvents and alcohol precipitation. Prior art has suggested, however, that transposition reaction products formed during in vitro insertion experiments are DNA: protein complexes that are extremely stable; evidence suggests that a chaperone-like activity is required for disruption of these products. Accordingly, organic extraction was deemed required for satisfactory disruption of the complexes.

This example demonstrates that heat inactivation at 75° C. is adequate for disrupting these complexes or at least for putting them into a form that can be introduced into the cell by chemical transformation.

Section A. Materials

A1) PROTEINS

TnsA 30 µg/ml in 10% glycerol

TnsB 20 µg/ml in 25% glycerol $TnsC_{127}$ 100 µg/ml in 10% glycerol

Keep stored at −70° C. Sufficient protein for 10 reactions is provided. At the time of use, keep frozen on dry ice until ready to add to the reaction, and keep on dry ice until returned to the freezer.

A2) BUFFER CONSTITUENTS

| HEPES | 0.25 M pH 8.1 |
|---|---|
| Tris[Cl] | 0.25 M pH 7.6 |
| BSA | 10 mg/ml |
| tRNA | 50 µg/ml |
| DTT | 1 M |
| ATP | 100 mM |
| MgAcetate | 375 mM |

Figure 14:
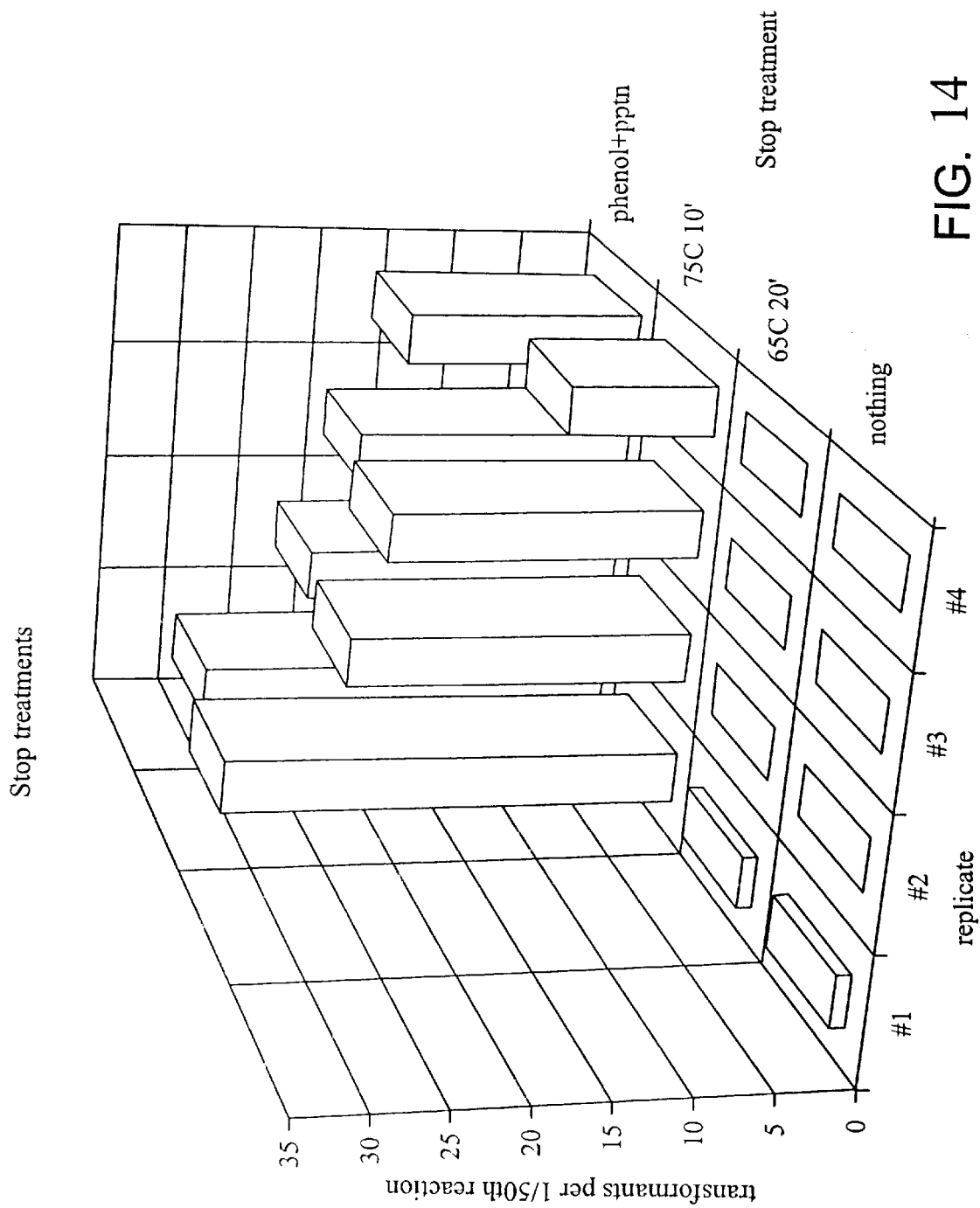
FIG. 14. Effect of four methods of stopping the transposition reaction in preparation for introduction into cells. Results for four replicates (abcissa) of each of four stop methods (z axis), reported as number of transformants per 1/50th of the total reaction (ordinate). Treatments were: no treatment; heat treatment at 65° C. for 20 min; heat treatment at 75° C. for 10 min; and phenol extraction followed by ethanol precipitation. Heat treatment at 75° C. but not 65° C. allows effective recovery.

A3) TRANSPOSON DONOR PLASMID 100 µg/ml
  This is as described for Example 3.
A4) TARGET PLASMID
  pLITMUS28 400 µg/ml
A5) OTHER
  Millicue water
  Heat block, 30° C.
  1.5 ml microtubes.
A6) FOR STOPPING THE REACTION
  when using chemically competent cells
    Water bath or heat block, 75° C.
    Water bath or heat block, 65° C.
    Distilled phenol equilibrated with TE
    Chloroform equilibrated with TE
    EtOH for precipitation
    NaCl 3 M
    Water or 1 mM Tris pH 8
CHEMICALLY COMPETENT TRANSFORMABLE CELLS:
  In this example, we show the use of
    Chemically competent ER 1821 ($2×10^7$ transformants/µg of LITMUS
    Chemically competent ER2502 ($6×10^6$ transformants/µg of LITMUS
    prepared as in Example 3
A8) MEDIA
  Rich Broth and Rich Agar (Kan, Amp) prepared as in Example 3.
Section B. Tn7 in vitro Transposition Reaction Protocol
1. Experiment 1. Four stop treatments
  Reactions were carried out as in Example 3, using quadruplicate samples for each of four treatments. At step 12, one of these treatments was substituted. For transformation, ER2502 was used.
Treatment 1: No treatment.
Treatment 2: Heat treatment at 65° C. for 20 min.
Treatment 3: Heat treatment at 75° C. for 10 min.
Treatment 4: Phenol extraction once, chloroform extraction once, ethanol precipitation once, resuspension in original volume of TE.
  The results of this experiment are given in Table 9 below and illustrated in FIG. 14.

TABLE 10

Transformants obtained per 1/50th volume of transposition reaction

| | Replicate | | | |
|---|---|---|---|---|
| | #1 | #2 | #3 | #4 |
| nothing | 1 | 0 | 0 | 0 |
| 65° C. 20' | 1 | 0 | 0 | 0 |
| 75° C. 10' | 32 | 24 | 22 | 10 |
| phenol + pptn | 30 | 23 | 20 | 17 |

2. Experiment 2. Three stop treatments

Reactions were carried out as in Example 3, using duplicate samples for each of three stop treatments, for two aliquots of TnsB, and for three volumes of TnsB. At step 12, one of the stop treatments was substituted. For transformation, ER 1821 was used.

Treatment 1: Heat treatment at 75° C. for 10 min.

Treatment 2: Ethanol precipitation only, resuspension in original volume of TE

Treatment 3: Heat treatment at 65° C. for 20 min

Figure 15:
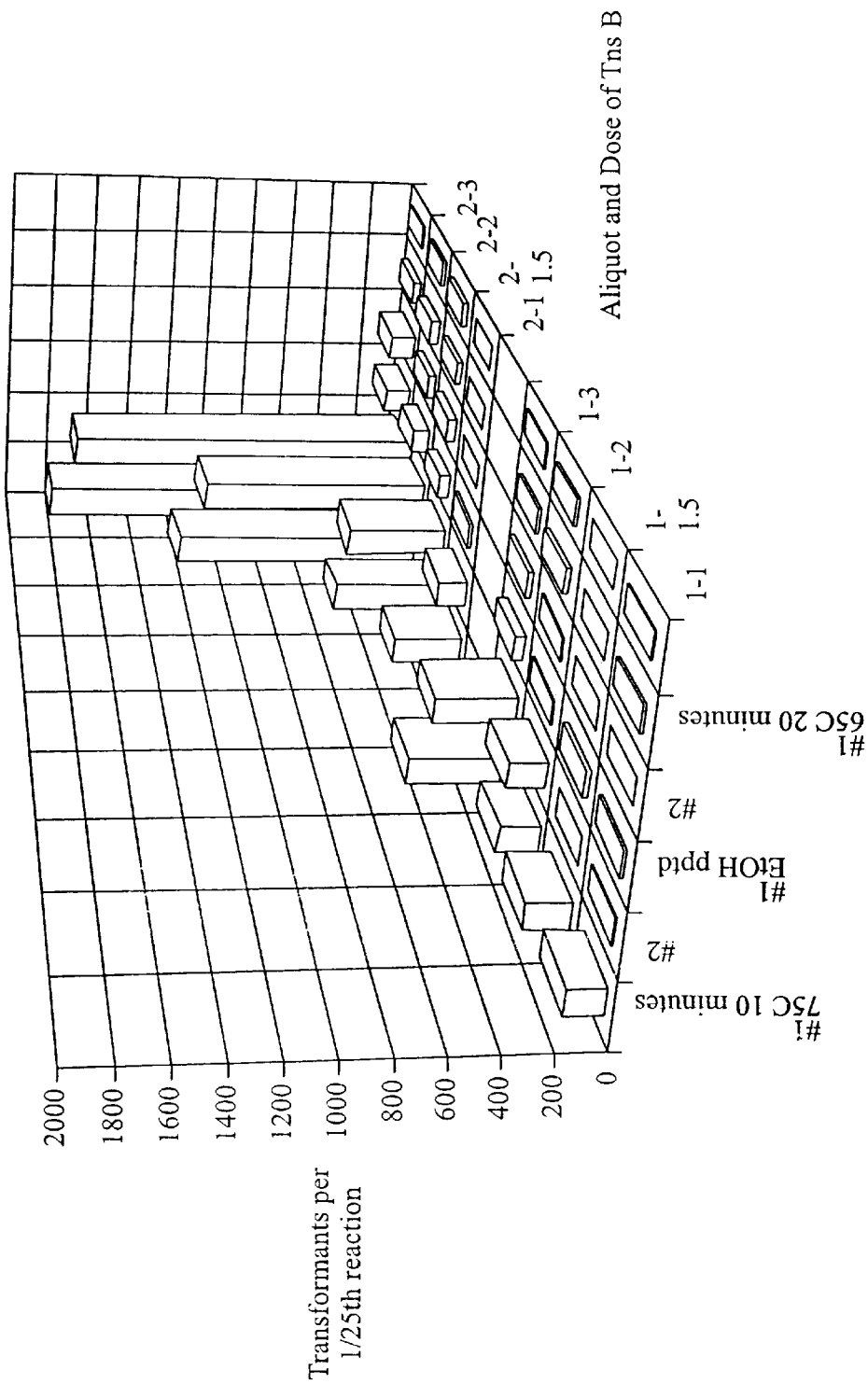
FIG. 15. A second experiment displaying the effect of three methods of stopping the transposition reaction in preparation for introduction into cells. Results are shown for two replicates of each of three stop methods (abcissa) for four doses of two different aliquots of TnsB (z axis), reported as number of transformants per 1/25th reaction. Treatments were: heat treatment at 75° C. for 10 min; ethanol precipitation alone; or heat treatment at 65° C. for 20 min. On the z axis, two aliquots (1- or 2-) of TnsB were used, in four different doses, 1 $\mu$l, 1.5 $\mu$l, 2 $\mu$l or 3 $\mu$l. The row labeled 1–2, for example, employed aliquot 1 and used 2 $\mu$l of it. Heat treatment at 75° C. but not 65° C. allows effective recovery. This experiment also illustrates the dose-response to TnsB.

The results of this experiment are given in Table 9 below and illustrated in FIG. 15.

TABLE 9

Transformants obtained per 1/50th volume of transposition reaction, three stop treatments.

| TnsB | | 75° C. 10 min | | EtOH pptd | | 65° C. 20 min. | |
|---|---|---|---|---|---|---|---|
| Aliquot | Volume ($\mu$l) | #1 | #2 | #1 | #2 | #1 | #2 |
| 1 | 1 | 158 | 8 | 13 | 3 | 15 | 10 |
| 1 | 1.5 | 186 | 0 | 16 | 0 | 3 | 0 |
| 1 | 2 | 178 | 170 | 13 | 13 | 30 | 16 |
| 1 | 3 | 454 | 366 | 47 | 21 | 11 | 8 |
| 2 | 1 | 324 | 140 | 21 | 3 | 9 | 2 |
| 2 | 1.5 | 506 | 462 | 58 | 44 | 25 | 25 |
| 2 | 2 | 1220 | 1102 | 88 | 37 | 54 | 18 |
| 2 | 3 | 1802 | 1690 | 129 | 126 | 37 | 14 |

These two experiments demonstrate that heat treatment at 75° C. for 10 min is an adequate method of stopping the transposition reaction and gives as many transformants as treatment with phenol, chloroform and ethanol precipitation; whereas no treatment, ethanol precipitation alone, and heat treatment at 65° C. for 20 min is inadequate, giving no transformants or a greatly reduced number of transformants.

Example 6

Storing Three Components of Tn 7 Transposase Together

Convenient routine use of in vitro transposition as a method in molecular biology would be facilitated if the protein components of the reaction could be stored in a single tube. In this way, variability in volume measurement from one experiment to another would be minimized, time and labor would be saved, and reproducibility enhanced. The TnsABC$_{127}$ transposition reaction described in the foregoing examples involves the addition of three different protein components.

This example demonstrates that these three protein components of the reaction can be mixed and stored together without interfering with the efficiency of the transposition reaction.

Section A. Materials

A1) INDIVIDUAL PROTEINS

TnsA 30 $\mu$g/ml in 10% glycerol

TnsB 20 $\mu$g/ml in 50% glycerol

TnsC$_{127}$ 100 $\mu$g/ml in 50% glycerol

Keep stored at −70° C.

A2) MIXED PROTEINS, COMPRISING

TnsA 7.36 $\mu$g/ml

TnsB 11.3 $\mu$g/ml

TnsC$_{127}$ 18.9 $\mu$g/ml in 40% glycerol

A2a) Keep stored at −70° C., or

A2b) Keep stored at −20° C.

A3) OTHER COMPONENTS

These are as in example 1, parts A and B; including chemically competent ER2502 (6×10$^6$ transformants/$\mu$g of LITMUS) prepared as in example 1.

Section B. Tn7 In Vitro Transposition Reaction Protocol

B1. Reaction volume=100 $\mu$l

B2. Experimental variations (2 experiments are shown, reactions were carried out in quadruplicate).

Tube 1 Proteins of A1 added individually at step 6 below in a total volume of 5.3 $\mu$l Tube 2 Mixture of A2a added together at step 6 below in a total volume of 5.3 $\mu$l Tube 3 Mixture of A2b added together at step 6 below in a total volume of 5.3 $\mu$l (Experiment 2 only)

B3. Make up a mix as in Example 1, section C

B4. Dispense mix of step 3 as in Example 1, section C

B5. Add target DNA as in Example 1, section C. In this example, this is pLITMUS28, 1 $\mu$l B6. Add to each tube

| | Tube 1 | Tube 2 | Tube 3 |
|---|---|---|---|
| TnsA | 1.3 $\mu$l (40 ng) | | |
| TnsB | 3 $\mu$l (20 ng) | | |
| TnsC$_{127}$ | 1 $\mu$l (100 ng) | | |
| TnsABC$_{127}$ | 0 | 5.3 $\mu$l (39 ng A, 59.9 ng B 100.2 ng C$_{127}$) | 5.3 $\mu$l (39 ng A, 59.9 ng B 100.2 ng C$_{127}$) |

B7. Add 1 $\mu$l donor DNA (0.1 $\mu$g pMCB40) as in example 1C

B8. Incubate 10 minutes at 30° C. (assembly reaction) as in example 1C

B9. Add 4 $\mu$l MgAc (375 mM) to each tube as in example 1C

B10. Incubate 1 hour 30° C. (transposition reaction) as in example 1C

B11. Heat Inactivate 75° C. 10 minutes

B12. Transform using chemically competent cells, as in example 1.

In this example, selective medium was RB Kan (20 $\mu$g/ml) Amp (100 $\mu$g/ml). Competent cells were ER2502, chemically competent (Example 1, Section D1).

C. Transformation Result

Experiment 1: Proteins were stored individually at −70° C. or as a mixture at −70° C. (A2a). In this experiment, the proteins in both treatments had suffered the same number of freeze-thaw cycles. 10 $\mu$l of each 100 $\mu$l reaction was transformed, and 100 $\mu$l of the 500 $\mu$l outgrowth culture was plated.

TABLE 10

Figure 16:
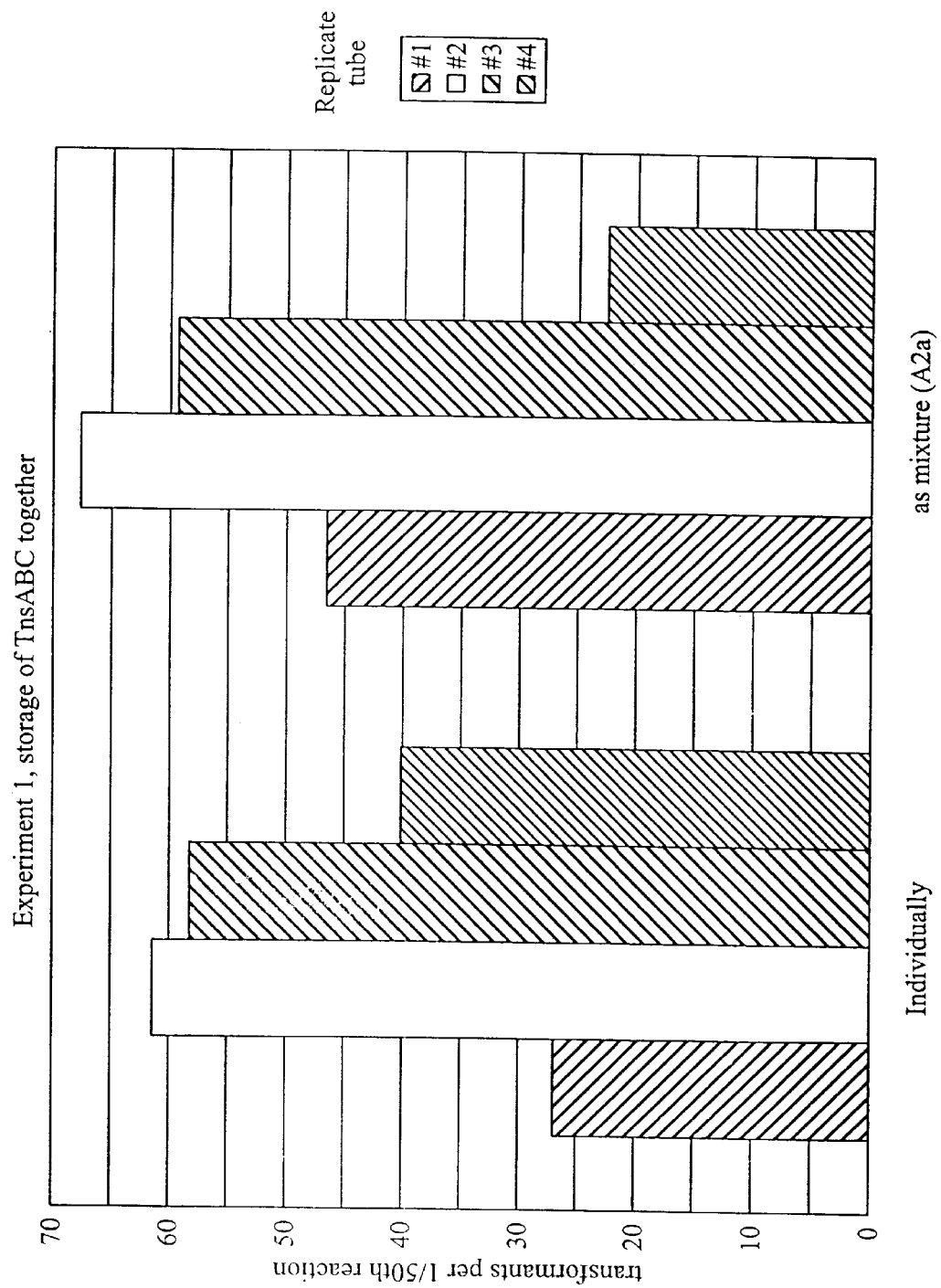
FIG. 16. Effect of two methods of storing proteins on the efficiency of the transposition reaction. Abcissa displays the storage conditions tested: "individually", TnsA, TnsB and TnsC proteins stored individually in separate tubes at −70° C.; "as a mixture (A2a)", TnsA, TnsB and TnsC proteins stored together as a mixture at −70° C. Ordinate displays the number of transformants per 1/50th of the total reaction. Each treatment was tested in quadruplicate.

Transformants obtained per 1/50th volume of transposition reaction, transposition proteins added as a mixture or individually. Result is displayed in FIG. 16

| | Replicate | | | | | |
|---|---|---|---|---|---|---|
| Storage | #1 | #2 | #3 | #4 | average | avg per reaction |
| Individually | 27 | 62 | 59 | 41 | 47 | 2350 |
| As a mixture | 47 | 68 | 60 | 23 | 49 | 2450 |

Experiment 2: Proteins were stored individually at −70° C., as a mixture at −70° C. (A2a material) or as a mixture at −20° C. (A2b material). In this experiment, the proteins stored individually had suffered more freeze-thaw cycles than those stored together. 10 μl of each 100 μl reaction was transformed, and 100 μl of the 500 μl outgrowth culture was plated.

TABLE 11

Figure 17:
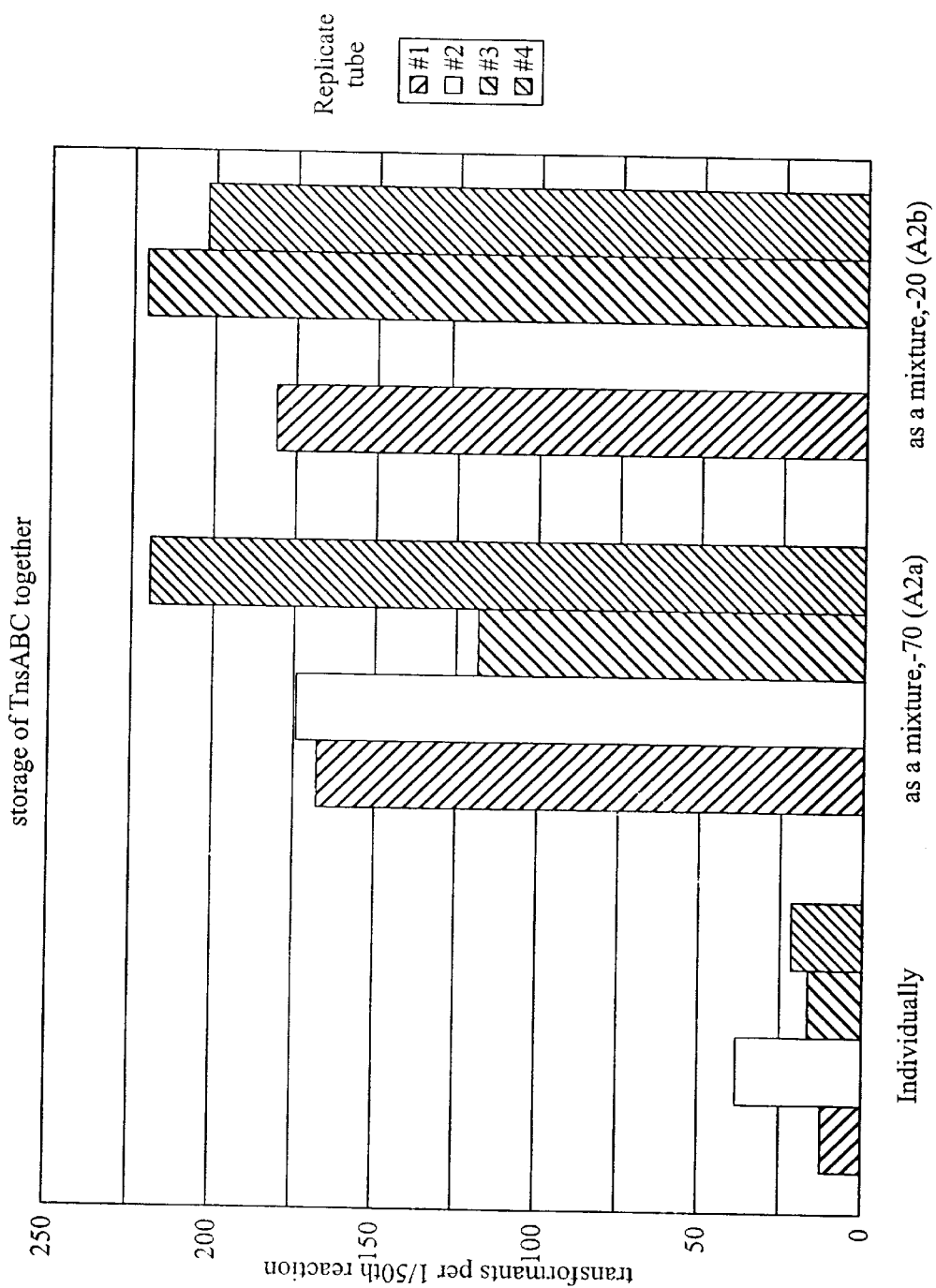
FIG. 17. Effect of three methods of storing proteins on the efficiency of the transposition reaction. Abcissa displays the storage conditions tested: "individually", TnsA, TnsB and TnsC proteins stored individually in separate tubes at −70° C.; "as a mixture, −70 (A2a)", TnsA, TnsB, and TnsC proteins stored together as a mixture at −70° C. "as a mixture, −20 (A2b)", TnsA, TnsB and TnsC proteins stored together as a mixture at −20° C. Ordinate displays the number of transformants per 1/50th of the total reaction. Each treatment was tested in quadruplicate.

Transformants obtained per 1/50th volume of transposition reaction, transposition proteins added as a mixture or individually following storage at −20° C. or −70° C. Result is displayed in FIG. 17.

| Storage | Replicate | | | | average | avg per reaction |
|---|---|---|---|---|---|---|
| | #1 | #2 | #3 | #4 | | |
| Individually | 13 | 38 | 17 | 22 | 22 | 1100 |
| As a mixture, −70° C., (A2a) | 167 | 173 | 117 | 218 | 168 | 8400 |
| As a mixture, −20° C., (A2b) | 179 | 125 | 219 | 199 | 180 | 9000 |

These two experiments demonstrate that the three Tns proteins can be stored together. The difference in experiment 2 between individual storage and storage together may be attributed to the number of freeze-thaw cycles.

BIBLIOGRAPHY

1. Craig N L. 1997. In Ann Rev Biochem. ed. pp. 437–74. Palo Alto: *Annual Reviews Inc.*
2. Kleckner N. 1989. In Mobile DNA. ed. Berg D and Howe M, pp. 227–68. Washington, D.C.: *American Society for Microbiology*.
3. van Luenen H G A M, et al. 1994. *Nucleic Acids Res.* 22:262–94. Rosenzweig B, et al. 1983. *Nucleic Acids Res.* 11:4201–10.
5. Mori I, et al. 1988. *Proc Natl Acad Sci USA.* 85:861–4
6. Eide D, et al. 1988. *Mol Cell Biol.* 8:737–46
7. Mizuuchi M, et al. 1993. *Cold Spring Harbor Symp. Quant. Biol.* 58:515–23
8. Berg D E. 1989. In Mobile DNA. ed. Berg D and Howe M, pp. 185–210. Washington, D.C.: *American Society for Microbiology*.
9. Kirchner J, et al. 1995. *Science.* 267:1443–4
10. Rogers M, et al. 1986. *Mol. Gen. Genet.* 205:550–6
11. Waddell C S, et al. 1988. *Genes Dev.* 2:137–49
12. Sarnovsky R, et al. 1996. *EMBO J.* 15:6348–61
13. Kubo K M, et al. 1990. *J. Bacteriol.* 172:2774–8
14. Wolkow C A, et al. 1996. *Genes Dev.* 10:2145–57
15. Hauer B, et al. 1984. *Mol Gen Genet.* 194:149–58
16. Arciszewska L K, et al. 1989. *J. Mol. Biol.* 207:35–52
17. Lee C-H, et al. 1983. *Proc Natl Acad Sci USA.* 80:6765–9
18. Reyes I, et al. 1987. *Plasmid.* 18:183–92
19. Adzuma K, et al. 1988. *Cell.* 53:257–66
20. Sakai J, et al. 1995. *EMBO J.* 14:4374–83
21. Kleckner N, et al. 1996. *Curr Top Microbiol Immunol.* 204:49–82
22. Bainton R, et al. 1991. *Cell.* 65:805–16
23. Bainton R J, et al. 1993. *Cell.* 72:931–43
24. Gamas P, et al. 1992. *Nuc. Acids Res.* 20:2525–32
25. Stellwagen A, et al. 1997. *Genetics.* 145:573–85
26. Stellwagen A, et al. 1997. *EMBO J.* (in press):
27. Sankar P, et al. 1993. *J.Bacteriol.* 1 75:5145–52
28. Devine S E, et al. 1994. *Nucleic Acids Res.* 22:3765–72
29. Pryciak P M, et al. 1992. *Proc Natl Acad Sci USA.* 89:9237–41
30. Pryciak P M, et al. 1992. *Cell.* 69:769–80
31. Pryciak P M, et al. 1992. *Embo J.* 11:291–303
32. Singh I R, et al. 1997. *Proc Natl Acad Sci USA.* 94:1304–09
33. Kholodii G, et al. 1995. *Mol. Microbiol.* 17:1189–200
34. Radstrom P, et al. 1994. *J. Bacteriol.* 1 76:3257–68
35. Reimmann C, et al. 1989. *Mol Gen Genet.* 215:416–24
36. Rowland S-J, et al. 1990. *Mol. Microbiol.* 4:961–75
37. Walker, et al., eds. 1983. *Techniques in Molecular Biology.* New York: MacMillan Publishing Company
38. Kunkel. 1985. *Proc Natl Acad Sci USA.* 82:488–92
39. Kunkel, et al. 1987. *Methods Enzymol.* 154:367–82
40. Sambrook J, et al., eds. 1989. *Molecular Cloning: A Laboratory Manual.* Cold Spring Harbor, N.Y.: Cold Spring Harbor Press
41. Dayhoff, et al., eds. 1978. Washington, D.C.: *Natl. Biomed. Res. Found.*
42. Miller J H. 1972. In *Experiments in Molecular Genetics.* ed. pp. Cold Spring Harbor, N.Y.: Cold Spring Harbor Laboratory.
43. Elespuru R K, et al. 1979. *Environ Mutagen.* 1:65–78
44. Yarmolinsky M B, etal. 1983. *Mol Gen Genet.* 192:140–8
45. Haniford D B, et al. 1989. *Cell.* 59:385–94
46. McKown R L, et al. 1987. *Proc.Natl.Acad.Sci. USA.* 84:7807–11
47. McKown R L, et al. 1988. *J. Bacteriol.* 170:352–8
48. Johnson R C, et al. 1984. *Genetics.* 9–18
49. Rose M D, et al., eds. 1990. *Methods in Yeast Genetics: A Laboratory Course Manual.* Cold Spring Harbor: Cold Spring Harbor Laboratory
50. Hughes O. 1993. *Host Components of Tn7 Transposition.*
51. Huisman O, et al. 1987. *Genetics.* 116:185–9
52. DeBoy R, et al. 1996. *J. Bacteriol.* 178:6184–91
53. Flores C, et al. 1990. *Nucl. Acids Res.* 18:901–11
54. Walker J E, et al. 1984. *Biochem J.* 224:799–815
55. Saraste M, et al. 1990. *Trends Biochem Sci.* 15:430–4
56. Sancar A, et al. 1993. *Science.* 259:1415–20
57. Chaconas G, et al. 1985. *J Biol Chem.* 260:2662–9
58. Faelen M, et al. 1978. *Nature.* 271:580–2
59. O'Day K J, et al. 1978. In *Microbiology.* ed. Schlessinger D, pp. 48–51. Washington, D.C.: American Society of Microbiology.
60. Surette M G, et al. 1987. *Cell.* 49:254–62
61. Craigie R, et al. 1987. *Cell.* 51:493–501
62. Koonin E V. 1992. *Nucleic Acids Res.* 20:1997
63. Gary P A, et al. 1996. *J. Mol. Biol.* 257:301–16
64. Gwinn M L, et al. 1997. *J. Bacteriology.* 179:7315–20
65. Bender J, et al. 1992. *EMBO J.* 11:741–50
66. Lichtenstein C, et al. 1982. Unique insertion site of Tn7 in *E coli* chromosome. 297:601 −3 #001 #

What is claimed is:

1. A mutant TnsC transposition regulatory protein comprising an alanine to valine substitution at residue 225 of SEQ ID NO:2 (TnsC$^{A225V}$) wherein the mutant protein activates TnsA+B transposase in the absence of TnsD or TnsE.

2. A Tn7 transposon comprising a DNA segment encoding a TnsA protein, a TnsB protein, and a mutant TnsC transposition regulatory protein comprising an alanine to valine substitution at residue 225 of SEQ ID NO:2 (TnsC$^{A225V}$) wherein the mutant TnsC protein activates TnsA+B transposase in the absence of TnsD or TnsE.

3. A composition comprising a mutant TnsC transposition regulatory protein, a transposable element and a transposase wherein the mutant TnsC protein comprises an alanine to valine substitution at residue 225 of SEQ ID NO:2 (TnSC$^{A225V}$) and activates the transposase in the absence of TnsD or TnsE thereby directing intermolecular transposition of the transposable element in a manner which is characterized by reduced target site selectivity.

4. The composition of claim 3 further comprising TnsD or TnsE.

5. The composition of claim 3 further comprising target DNA into which the transposable element inserts.

6. The composition of claim 3 in which the transposable element contains at least one primer binding site that is native to said transposon or heterologous.

7. The composition of claim 6 further comprising primers that hybridize to said primer binding site on the transposable element.

8. The composition of claim 3 in which the transposable element contains a heterologous DNA sequence.

9. A Tn7 transposable system comprising a transposon which encodes a TnsA protein, a TnsB protein, a transposable element and a mutant TnsC transposition regulatory protein wherein the mutant TnsC protein comprises an alanine to valine substitution at residue 225 of SEQ ID NO:2 (TnSC$^{A225V}$) and directs intermolecular transposition in a manner which discriminates between immune and nonimmune targets and is characterized by reduced target site selectivity.

10. The Tn7 transposable system of claim 9 further comprising a target sequence into which the transposable element inserts.

11. The Tn7 transposable system of claim 9 in which said transposon contains at least one primer binding site that is native to said transposon or heterologous.

12. The Tn7 transposable system of claim 11 further comprising primers that hybridize to the primer binding site on said transposon.

13. The Tn7 transposable system of claim 9 in which the transposable element comprises a heterologous DNA sequence.

14. A kit containing the composition according to claim 9.

* * * * *

UNITED STATES PATENT AND TRADEMARK OFFICE
CERTIFICATE OF CORRECTION

PATENT NO.    : 6,420,524 B1
DATED         : July 16, 2002
INVENTOR(S)   : Craig It is certified that error appears in the above-identified patent and that said Letters Patent is hereby corrected as shown below:

<u>Column 1,</u>
Line 7, insert -- This invention was made with Government support under Grant No. GM53824, between the National Institute of Health and Johns Hopkins University School of Medicine. The Government has certain rights in the invention. --

Signed and Sealed this

Twenty-eighth Day of October, 2003

JAMES E. ROGAN
*Director of the United States Patent and Trademark Office*